(12) United States Patent
Ruoslahti et al.

(10) Patent No.: US 7,560,242 B2
(45) Date of Patent: Jul. 14, 2009

(54) METADHERIN POLYPEPTIDES, ENCODING NUCLEIC ACIDS AND METHODS OF USE

(75) Inventors: Erkki Ruoslahti, Rancho Santa Fe, CA (US); Darren M. Brown, Carlsbad, CA (US)

(73) Assignee: The Burnham Institute, La Jolla, CA (US)

( * ) Notice: Subject to any disclaimer, the term of this patent is extended or adjusted under 35 U.S.C. 154(b) by 481 days.

(21) Appl. No.: 10/986,466

(22) Filed: Nov. 10, 2004

(65) Prior Publication Data

US 2005/0208057 A1   Sep. 22, 2005

Related U.S. Application Data

(60) Provisional application No. 60/519,675, filed on Nov. 13, 2003.

(51) Int. Cl.
| | |
|---|---|
| G01N 33/574 | (2006.01) |
| G01N 33/53 | (2006.01) |
| G01N 33/566 | (2006.01) |
| G01N 33/48 | (2006.01) |
| G01N 33/00 | (2006.01) |
| C12Q 1/70 | (2006.01) |
| C07K 1/00 | (2006.01) |

(52) U.S. Cl. ............... 435/7.23; 435/4; 435/7.1; 435/7.21; 436/501; 436/64; 436/86; 530/350; 530/380; 530/385; 530/386; 530/387.1; 530/387.7; 530/387.9; 530/388.1; 530/388.15; 530/388.2

(58) Field of Classification Search ............... 435/4, 435/7.1, 7.21, 7.23; 436/501, 64, 86; 530/350, 530/380, 385, 386, 387.1, 387.7, 387.9, 388.1, 530/388.15, 388.2
See application file for complete search history.

(56) References Cited

U.S. PATENT DOCUMENTS

2006/0205934 A1 * 9/2006 Macina et al. ............. 536/23.5

FOREIGN PATENT DOCUMENTS

| WO | WO 00/56765 | 9/2000 |
|---|---|---|
| WO | WO 03/077875 A2 | 9/2003 |
| WO | WO 2004/016732 A2 | 2/2004 |
| WO | WO 2004/053075 A2 | 6/2004 |

OTHER PUBLICATIONS

GenCore amino acid databases. Sequence alignment between Applicant' Seq Id No. 13 and 17 and U.S. Patent Application Publication 20060205934 A1 (effective filing date Dec. 5, 2002), 2 sheets.*

(Continued)

*Primary Examiner*—Alana M. Harris
(74) *Attorney, Agent, or Firm*—Knobbe Martens Olson & Bear LLP

(57) ABSTRACT

Metadherin, a protein that controls metastasis, and variants of metadherin are described. DNA sequences encoding the same and methods of production are described. Therapies involving the application of metadherin, binding agents that bind to metadherin, such as antibodies, and expression modulating agents, such as siRNA, are described. The use of metadherin or metadherin variants for delivering desired substances to particular lung tissue is described. A method of diagnosing metastatic cells based on the presence of metadherin is described.

15 Claims, 11 Drawing Sheets

Lung-homing domain of Metadherin

GLNGL SSADP SSDWN APAEE WGNWV DEDRA SLLKS QEPIS
NDQKV SDDDK EKGEG ALPTG KSK$_{63}$

OTHER PUBLICATIONS

Abdel-Ghany, M. et al., *J Biol Chem* 276: 25438-25446 (2001).
Altschul, S.F., et al., *Nucleic Acids Res* 25: 3389-3402 (1997).
Amer, M.H., *J Surg Oncol* 19: 101-105 (1982).
Aslakson, C.J. and Miller, F.R., *Cancer Res* 52: 1399-1405 (1992).
Berlin et al. Development of a novel spontaneous metastasis model of human osteosarcoma transplanted orthotopically into bone of athymic mice. Cancer Res 53, 4890-4895 (1993).
Boogerd, W., *Radiother Oncol* 40, 5-22(1996).
Brown, D. et al. Metadherin, a cell surface protein in breast tumors that mediates lung metastasis. Cancer Cell 5, 365-374 (2004).
Chambers, A.F. et al., *Nat Rev Cancer* 2: 563-572 (2002).
Cheng, H.C. et al., *J Biol Chem* 273: 24207-24215 (1998).
Dexter, D.L. et al., *Cancer Res* 38: 3174-3181 (1978).
Elble, R.C., et al., *J Biol Chem* 272: 27853-27861 (1997).
Fidler, I. J., *Surg Oncol Clin N Am* 10: 257-269, vii-viiii. (2001).
GenBank databases, Accession No. AK029915, Sequence 13, Apr. 3, 2004.
Glasgow, J. (1998), Proceedings, Sixth International Conference on Intelligent Systems for Molecular Biology : Jun. 28-Jul. 1, 1998, Montreal, Quebec (Menlo Park, Calif., AAAI Press); pp. 193-202.
Harris, J. et al., Cancer of the breast. In *Cancer, principles and practice of oncology* (Philadelphia, Lippincott Co.), pp. 1602-1616 (1982) and p. 1119-1171.
Johnson, R.C. et al., *J Cell Biol* 121: 1423-1432 (1993).
Kamby, C. et al., *Cancer* 59: 1524-1529 (1987).
Krogh, A., et al, *J Mol Biol* 305: 567-580 (2001).
Kyte, J. and Doolittle, R.F., *J Mol Biol* 157, 105-132 (1982)).
Laakkonen, P. et al., *Nat Med* 8: 751-755 (2002)).
Lal, A., et al., *Cancer Res* 59: 5403-5407 (1999).
Lash, A.E., et al., *Genome Res* 10: 1051-1060 (2000)).
McIntosh, D.P., et al., *Proc Natl Acad Sci U S A* 99: 1996-2001 (2002).
Miller et al., Characterization of metastatic heterogeneity among subpopulations of a single mouse mammary tumor: hetereogeneity in phenotypic stability. Invasion Metastasis 3, 22-31 (1983).
Muller, A., et al., *Nature* 410: 50-56 (2001).
Orr, F.W. and Wang, H.H., *Surg Oncol Clin N Am* 10: 357-381, ix-x (2001).
Price et al. Tumorigenicity and metastasis of human breast carcinoma cell lines in nude mice. Cancer Res 50, 717-721 (1990).
Pulaski, B.A. and Ostrand-Rosenberg, S., *Cancer Res* 58: 1486-1493 (1998)).
Radinsky, R., *Cancer Metastasis Rev* 14: 323-338 (1995).
Rajotte, D. and Ruoslahti, E., *J Biol Chem* 274: 11593-11598 (1999).
Ruoslahti, E., *Nat Rev Cancer* 2: 83-90 (2002).
Rutgers, E.J. et al., *Br J Surg* 76: 187-190 (1989).
Sackett et al., Clinical Epidemiology: A Basic Science for Clinical Medicine, Little Brown and Co., 1985, p. 106-7.
Tomin, R. and Donegan, W.L., *J Clin Oncol* 5: 62-67 (1987).
Van't Veer, et al., *Nature* 415: 530-536 (2002).
Weiss, L., *Clin Exp Metastasis* 10: 191-199 (1992).
Arap, W., Haedicke, W., Bernasconi, M., Kain, R., Rajotte, D., Krajewski, S., Ellerby, H. M., Bredesen, D. E., Pasqualini, R., and Ruoslahti, E. (2002). Targeting the prostate for destruction through a vascular address, Proc Natl Acad Sci U S A 99, 1527-1537.
Arap, W., Pasqualini, R., and Ruoslahti, E. (1998). Cancer treatment by targeted drug delivery to tumor vasculature in a mouse model. Science 279, 377-380.
Hoffman, J. A., Laakkonen, P., Porkka, K., Bernasconi, M., and Ruoslahti, E. (in press). in vivo and ex vivo selections using phage-displayed libraries. In Phage Display: A Practical Approach, H. Lowman, ed. (Oxford, UK, Oxford University Press).
Laemmli, U. K. (1970). Cleavage of structural proteins during the assembly of the head of bacteriophage T4. Nature 227, 680-685.
Mechler, B. M. (1987). Isolation of messenger RNA from membrane-bound polysomes. Methods Enzymol 152, 241-248.
Pasqualini, R., and Ruoslahti, E. (1996). Organ targeting in vivo using phage display peptide libraries. Nature 380, 364-366.
Porkka, K., Laakkonen, P., Hoffman, J. A., Bernasconi, M., and Ruoslahti, E. (2002). A fragment of the HMGN2 protein homes to the nuclei of tumor cells and tumor endothelial cells in vivo. Proc Natl Acad Sci U S A 99, 7444-7449.
Rajotte, D., Arap, W., Hagedorn, M., Koivunen, E., Pasqualini, R., Ruoslahti, E. (1998). Molecular heterogeneity of the vascular endothelium revealed by in vivo phage display, J. Clin Invest 102, 430-437.
International Search Report (International Application No. PCT/US04/37471), Apr. 22, 2005.
Supplementary Partial European Search Report (Application No. 04816947.8 PCT/US2004037471), May 24, 2007.
GenBank accession No. AK000745, version AK000745.1, Sep. 12, 2006.
GenBank accession No. NP_848927, version NP_848927.1, available at http://www.ncbi.nlm.nih.gov/entrez/viewer.fcgi?db=protein&id=30520310, Sep. 3, 2007.
GenBank accession No. NM_178812, version NM_178812.2; available at http://www.ncbi.nlm.nih.gov/entrez/viewer.fcgi?db=nuccore&id=31343604, Sep. 3, 2007.
GenBank accession No. AY082966, version AY082966.1, Sep. 9, 2004.
Britt et al. "Identification of a novel protein, LYRIC, localized to tight junctions of polarized epithelial cells" Exp. Cell Res. 300(1): 134-148 (2004).

* cited by examiner

FIG. 1A
Lung-homing domain of Metadherin
GLNGL SSADP SSDWN APAEE WGNWV DEDRA SLLKS QEPIS
NDQKV SDDDK EKGEG ALPTG $KSK_{63}$
FIG. 1B
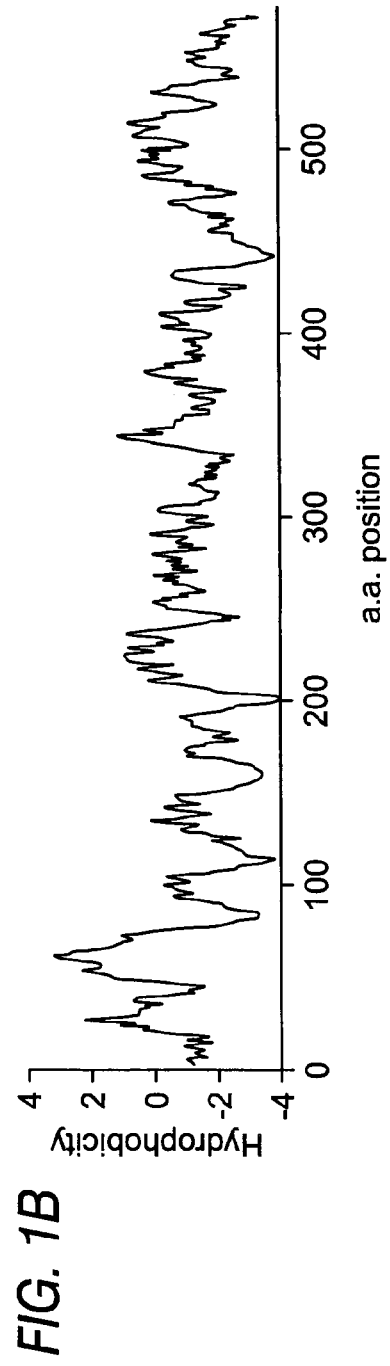
FIG. 1C
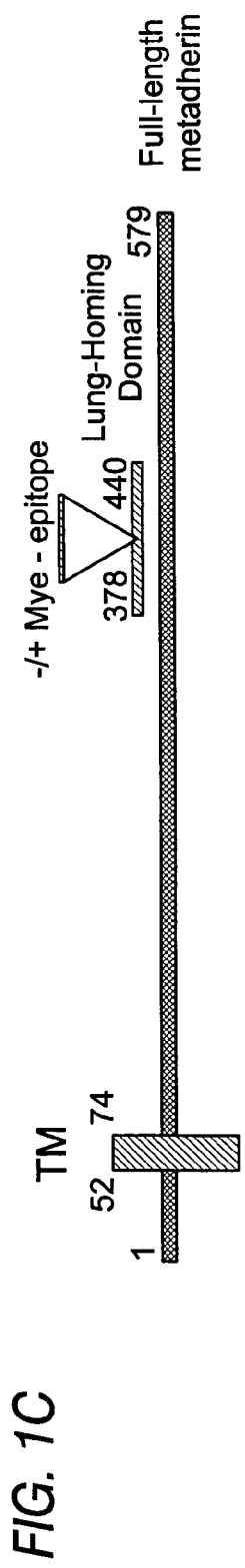

FIG. 2

```
                              1                                                              50
XP_043070  (human)      MAARSW...Q DELAQQAEEG SARLREMLSV GLGFLRTELG LDLGLEPKRY
NP_596889  (rat)        MAARSW...Q DELAQQAEEG SARLRELLSV GLGFLRTELG LDLGLEPKRY
XP_145357  (rat)        M......... .......... .......... .......... ..........
BAC26673   (mouse)      MAARSW...Q DELAQQAEEG SARLRELLSV GLGFLRTELG LDLGLEPKRY
XP_234949  (mouse)      MFTRKHLMPK DLILKHLTFA NS..LSIISR GIPRAMSDCG FKYFLDDIGC
XP_285992  (mouse)      MLAQKQRNNA C......... ......FKCG SLGHFKNDCP KNRGAEESGQ
CAD87805   (zebrafish)  M.DQDW...Q ALATQRAEYV SDRIRGLLSS GLDFLRAELG VDLGIKPEKC 51                                                             100
XP_043070  (human)      PGWVILVG.T GALGLLLLFL LGYGWAAACA GARKKRRSP. ...PRKREEA
NP_596889  (rat)        PSWVILVG.T GALGLLLLFL LGYGWAAACA GARKKRRSP. ...PRKREEV
XP_145357  (rat)        .......... .AIGYIS... .......... ....EKRS.. ..KARAGLLI
BAC26673   (mouse)      PGWVILVG.T GALGLLLLFL LGYGWAAACA GARKKRRSP. ...PRKREEA
XP_234949  (mouse)      KLIVYICRIT RGMSLYAMCL LSCFQAITIN QSNSKCLTLK HRTTKYIGSC
XP_285992  (mouse)      ASHA..PGGL WAVGVCSFQK ILSASDTSSM IFQVKARSLS VWMARAGLLI
CAD87805   (zebrafish)  PSWLIL.S.A ALIGLLLLVV L......AAC. GRRKRRAAPV TASPRSIAAA 101                                                            150
XP_043070  (human)      AAVPAAAPDD LALLKNLR.. SE..EQKKKN R.KKLSEKPK ..PNGRTVEV
NP_596889  (rat)        TP.PTPAPED PAQLKNLR.. SE..EQKKKN R.KKLPEKPK ..PNGRTVEI
XP_145357  (rat)        VPAQARGK.G AAVVQGLRHI GEYQKPRAKE QPKRLPEKPK Q..NRLLVEL
BAC26673   (mouse)      AP.PTPAPDD LAQLKNLR.. SE..EQKKKN R.KKLPEKPK ..PNGRTVEV
XP_234949  (mouse)      CSVSWLVQLF LNILTPTR.V SGPIYNKNVT N.MMSYGYCS WIASGNMATA
XP_285992  (mouse)      VPAQARGK.G AAVVQGLRHI GEYQKPRAKE QPKRLPEKPK Q..NRLLVEL
CAD87805   (zebrafish)  APVKTSAPP. ....KTVK.. TEPSEPKKKN K.KKAADKQK AQANGQTVAE 151                                                            200
XP_043070  (human)      AEGEA..... .......... .......... ...VRTPQSV TAKQP...PE
NP_596889  (rat)        PEDEV..... .......... .......... ...VRTPRSI TAKQP...PE
XP_145357  (rat)        PEDEVVS... .......... .......... .......RSI PAKQP...PK
BAC26673   (mouse)      PEDEV..... .......... .......... ...VRNPRSI TAKQA...PE
XP_234949  (mouse)      VY..VLLLCF SDAVCLGLMA CSSVSMVSIL YRHKRQVKHI HSAQHLIKDS
XP_285992  (mouse)      PEDEVVS... .......... .......... .......RSI PAKQP...PK
CAD87805   (zebrafish)  PQEEIKVTGE KKKAPAPTPT RAPAPAPTRA PAPAPTPASA PAPVPVPAPK 201                                                            250
XP_043070  (human)      IDKK...... ....NEKSKK NKKKSKSDAK AVQNSSRHDG KEVDE.GAWE
NP_596889  (rat)        TDKK...... ....NEKSKK NKKKSKSDAK AVQNSSRHDG KEVDE.GAWE
XP_145357  (rat)        RDTE...... ....NKKSKK NKKSSKSDAK AVPNSLCH.. ..........
BAC26673   (mouse)      TDKK...... ....NEKSKK NKKKSKSDAK AVQNSSRHDG KEVDE.GAWE
XP_234949  (mouse)      PEDRATQTIL ILMCTFVL.. ....SYSFSS IVVIFTTY.S KYPMLWGV..
XP_285992  (mouse)      RDTE...... ....NKKSKK NKKSSKSDAK AVPNSLCH.. ..........
CAD87805   (zebrafish)  PKQKPAPTPA QPPADTKTKK NKKKAKPELK TAQDVSSTDG KEPDEAGAWE 251                                                            300
XP_043070  (human)      TKISHREKRQ QRKRDKVLTD SGSLDSTIPG IENTITVTTE Q.LTTASFPV
NP_596889  (rat)        TKISHREKRQ QRKRDKVLTD SGSLDSTIPG IENTITVTTE Q.LTTASFPV
XP_145357  (rat)        TK........ .......... .......... ..NTITVTTS Q.LTTASFPV
BAC26673   (mouse)      TKISHREKRQ QRKRDKVLTD SGSLDSTIPG IENIITVTTE Q.LTTASFPV
XP_234949  (mouse)      TKARNSDEMW R......... .......... .....ILAII SNVTMVSIPI
XP_285992  (mouse)      TK........ .......... .......... .......... ..........
CAD87805   (zebrafish)  TKVSNREKRQ QRKKEKGPGE S....SGSPE SGDRASMKVE QPVVTAT..A
```

FIG. 2 Continued.

```
                         301                                                                    350
XP_043070  (human)       GSKKNKGDSH  LNVQVSNFKS  GKGDSTL.QV  SSGLNENLTV  NGGGWNEKSV
NP_596889  (rat)         GSKKNKGDSH  LNVQVSNFKS  GKGDSTL.QV  SSGLNENITV  NGGGWSEKSV
XP_145357  (rat)         DSKKNKGVSR  LNVQIS.ILV  WKGDTTI.QD  SSGKLGNLTV  NGGVWSENSV
BAC26673   (mouse)       GSKKNKGDSH  LNVQVSNFKS  GKGDSTL.QV  TSRLNENLTV  NGGGWSEKSV
XP_234949  (mouse)       SSHINHDSMY  YEMKDKNVQ.  .....LVGSL  CSSY......  .GYSTAKQEV
XP_285992  (mouse)       ..........  ..........  ..........  ..........  ..........
CAD87805   (zebrafish)   GNKKNK....  ...ESSRVKA  SKGDAIIAPV  TSAWNDVNSV  NGGGLTEVPV 351                                                                    400
XP_043070  (human)       KLSSQISA.G  EEKWNSVSPA  SAGKRKTEPS  AWSQDT.GD.  ANTNGKDWGR
NP_596889  (rat)         KLSSQLSA.G  EEKWNSVPPA  SAGKRKTEQS  AWTQDP.GD.  TNANGKDWGR
XP_145357  (rat)         KLASLLSTWE  VEL...CPTC  LCRQEKQSHL  LGLKTPVMEM  QMI..KTGER
BAC26673   (mouse)       KLSSQLS...  EEKWNSVPPA  SAGKRKTEPS  AWTQDT.GD.  TNANGKDWGR
XP_234949  (mouse)       SLETLLVAFT  LFTVPHYSGK  NVQAQNKAGL  TWKA.TLVPP  MQIHQKNVPP
XP_285992  (mouse)       ..........  ..........  .....KQSHL  LGLKTPVMEM  QMI..KTGER
CAD87805   (zebrafish)   KQAIQSNALN  NDKW.SAGKK  TSGHKNRENS  TWKQESEGPL  TGLDGRIKAE 401                                                                    450
XP_043070  (human)       SWSDRSIFSG  IG.STAEPVS  QSTTSDYQWD  VSRNQPYIDD  EWSGLNGLSS
NP_596889  (rat)         NWSDRSIFSG  IG.STAEPVS  QSTTSDYQWD  GSRNQPHIDD  EWSGLNGLSS
XP_145357  (rat)         TGVITQYF..  LAFESVEPVF  QTTTSDYQWD  VSHNQPCIDD  EWSEVNCGKQ
BAC26673   (mouse)       NWSDRSIFSG  IG.STAEPVS  QSTTSDYQWD  VSRNQPYIDD  EWSGLNGLSS
XP_234949  (mouse)       APKAPSLLSI  MKISVL....  .GEVRIHGME  TKLSKLVTSE  E...LGGKSS
XP_285992  (mouse)       TGVITQYF..  LAFESVEPVF  QTTTSDYQWD  VSHNQPCIDD  EWSEVNCGKQ
CAD87805   (zebrafish)   PNQVNLTMLG  LNPSGGETGS  KSSIEIGKWD  ...KTPVVDS  EWSSFNGLGS 451                                                                    500
XP_043070  (human)       ADPNSDWNAP  AEEWGNWVDE  ERASLLKSQE  PIPDDQKVSD  DDKEKGEGAL
NP_596889  (rat)         ADPSSDWNAP  AEEWGNWVDE  DRASLLKSQE  PISNDQKDSD  DDKEKGEGAL
XP_145357  (rat)         LRL....ECT  CRREGNWVDE  ERGSLLKSQE  LISNDQKFSD  DDKGKGEG..
BAC26673   (mouse)       ADPSSDWNAP  AEEWGNWVDE  DRASLLKSQE  PISNDQKVSD  DDKEKGEGAL
XP_234949  (mouse)       QPP.......  ..........  DRNATLRKR.  ..........  ..RENANWTI
XP_285992  (mouse)       VRP....NGP  SRHSG.....  ..........  ..........  ..........
CAD87805   (zebrafish)   VDPSSDWNAP  SELWDNFEAK  VDASALK.EI  PVSKPLVESN  DDKDKED...

501                                                                    550
XP_043070  (human)       PTGKSKKKKK  KKKKQGEDNS  TAQDTEELEK  EIREDLPVNT  SKTRPKQEKA
NP_596889  (rat)         PTGKSKKKKK  KKKKQGEDNS  ITQDTEDLEK  DTREELPVNT  SKARPKQEKA
XP_145357  (rat)         ..........  ..........  ..........  ..........  ..........
BAC26673   (mouse)       PTGKSKKKKK  KKKKQGEDNS  HTQDTEDLEK  DTREELPVNT  SKARPKQEKA
XP_234949  (mouse)       LNENKKKQKK  RKKKQGEDNY  FIQDTEELEK  DIREEILVTT  CKAIPNWENV
XP_285992  (mouse)       ..........  ..........  ..........  ..........  ..........
CAD87805   (zebrafish)   PAGGGKSKRR  KKKK......  ..........  ..........  ...RPEEE..

551                                                                    600
XP_043070  (human)       FSLKTISTSD  PAEVLVKNSQ  PIKTLPPATS  TEPSVILSKS  DSDKSSSQVP
NP_596889  (rat)         CSLKTMSTSD  PVEVLIKNSQ  PIKTLPPAIS  AEPSVTLSKG  DSDKSSSQVP
XP_145357  (rat)         ..........  .....IKNWH  PIQTPLPAIS  AE....LFSS  ATN.......
BAC26673   (mouse)       CSLKTMSTSD  PAEVLIKNSQ  PVKTLPPAIS  AEPSITLSKG  DSDNSSSQVP
XP_234949  (mouse)       CSLKTMSTID  PTEVDVKNEQ  CIQTLLPTIS  PE....LFST  ATD.......
XP_285992  (mouse)       ..........  ..........  ....PLP...  ........G  PVN.......
CAD87805   (zebrafish)   ........GS  AVEVIPEVSA  P.........  AEKSVTV...  ......KPHPP
```

FIG. 2 Continued

```
                        601                                                      650
XP_043070  (human)      PILQETDKSK SNTKQNSVPP ...SQTKSET SWESPKQIKK KKKARRE...
NP_596889  (rat)        PMLQDTDKPK SNAKQNSVPP ...SQTKSET NWESPKQIKK KKKARRE...
XP_145357  (rat)        .VTRFTDKHK SNAKQNSVPP PPLSQIRSET NYNSPKQIKK KKS.......
BAC26673   (mouse)      PMLQDTDKPK SNAKQNSVPP ...SQTKSET NWESPKQIKK KKKARRE...
XP_234949  (mouse)      .ITRFTDKHK SNTEQNSVPP SPLSQTRSAT NCKTPKQIKK KKKSQTGNVI
XP_285992  (mouse)      .PT.FT.... ......AFP. .......... .........E HAQ.......
CAD87805   (zebrafish)  PHV.....PK DAGSKQNIPP QS.SQKKSDQ NWEPPKQV.Q KKKVRRE...

651
XP_043070  (human)      ..T  (SEQ ID NO: 13)
NP_596889  (rat)        ..T  (SEQ ID NO: 18)
XP_145357  (rat)        ...  (SEQ ID NO: 14)
BAC26673   (mouse)      ..T  (SEQ ID NO: 1)
XP_234949  (mouse)      FLS  (SEQ ID NO: 19)
XP_285992  (mouse)      ...  (SEQ ID NO: 20)
CAD87805   (zebrafish)  ..T  (SEQ ID NO: 15)
```

METADHERIN POLYPEPTIDES, ENCODING NUCLEIC ACIDS AND METHODS OF USE

RELATED APPLICATION

This Application claims priority to U.S. Provisional Application Ser. No. 60/519,675, filed Nov. 13, 2003, hereby incorporated by reference in its entirety.

GOVERNMENTAL INTEREST

This work was supported by grants CA 82713, CA 30199, and CA09579 from the National Cancer Institute of the National Institutes of Health, and DAMD17-02-1-0315 from the Department of Defense. The government may have certain rights in this invention.

FIELD OF THE INVENTION

This invention relates to the field of molecular biology and molecular medicine and more specifically to the regulation of tumor metastasis.

BACKGROUND

Tumor metastasis is a complex, multi-step process in which cancer cells detach from the original tumor mass and establish metastatic foci at organ-specific sites (Fidler, I. J., *Surg Oncol Clin N Am* 10: 257-269, vii-viiii. (2001)). The location of the metastatic site depends on the particular type of cancer and stage of disease. For example, breast cancer typically spreads first to the lungs and liver (Kamby, C. et al., *Cancer* 59: 1524-1529 (1987); Rutgers, E. J. et al., *Br J Surg* 76: 187-190 (1989); Tomin, R. and Donegan, W. L., *J Clin Oncol* 5: 62-67 (1987)). Later in the disease, breast cancer spreads to the central nervous system and bone (Amer, M. H., *J Surg Oncol* 19: 101-105 (1982); Boogerd, W., *Radiother Oncol* 40, 5-22(1996)). The metastatic phase of the disease is devastating, given that conventional treatments are usually ineffective and patients typically survive only a few years after diagnosis (Harris, J. et al., Cancer of the breast. In *Cancer, principles and practice of oncology* (Philadelphia, Lippincott Co.), pp. 1602-1616 (1982)).

Several factors affect the location and growth of metastases. Depending on the blood-flow pattern from the primary tumor, certain tumor cells are carried preferentially to particular organs (Weiss, L., *Clin Exp Metastasis* 10: 191-199 (1992)). While in circulation, some tumor cells selectively recognize particular endothelial cell surface molecules that mediate cell adhesion to specific organs (Abdel-Ghany, M. et al., *J Biol Chem* 276: 25438-25446 (2001); Cheng, H. C. et al., *J Biol Chem* 273: 24207-24215 (1998); Johnson, R. C. et al., *J Cell Biol* 121: 1423-1432 (1993)). The arrest of tumor cells at the metastatic site, through mechanical trapping in small capillaries or through adhesive interactions with the endothelium, is a necessary step for tumors to become established at a secondary site (Chambers, A. F. et al., *Nat Rev Cancer* 2: 563-572 (2002); Orr, F. W. and Wang, H. H., *Surg Oncol Clin N Am* 10: 357-381, ix-x (2001)). Once the tumor cells have seeded the target organ, the local microenvironment influences whether or not a particular cancer cell will proliferate (Fidler, I. J., *Surg Oncol Clin N Am* 10: 257-269, vii-viiii (2001); Radinsky, R., *Cancer Metastasis Rev* 14: 323-338 (1995)). Unfortunately, many of the factors that contribute to organ-specific metastasis have yet to be elucidated.

Of the many possible factors, one such possible factor may be the protein or proteins that allow homing of a protein or a cell to a particular tissue by binding to a molecule in the tissue. Some lung-specific homing peptides have been isolated by in vivo phage display (Rajotte, D. and Ruoslahti, E., *J Biol Chem* 274: 11593-11598 (1999)) and antibodies that specifically bind to lung vasculature have been prepared (McIntosh, D. P., et al., *Proc Natl Acad Sci USA* 99: 1996-2001 (2002)). Tissue-specific expression of vascular markers is not limited to lung vasculature; recent data suggest that each tissue puts a specific signature on its vasculature (Ruoslahti, E., *Nat Rev Cancer* 2: 83-90 (2002)). Thus, binding of tumor cells to tissue-specific vascular markers may play a role in selective tumor metastasis to other tissues as well.

There are examples of adhesive interactions that are required in order for lung metastases to form. Dipeptidyl dipeptidase IV on lung endothelial cells was found to be an adhesion receptor for fibronectin on metastasizing breast and prostate carcinoma cells in a mouse model (Cheng, H. C. et al., *J Biol Chem* 273: 24207-24215 (1998); Johnson, R. C., et al., *J Cell Biol* 121: 1423-1432 (1993)). In another mouse model, $Ca^{2+}$-sensitive chloride channel, hCLCA2, on lung endothelial cells was reported to be a ligand for $\beta 4$ integrins on metastasizing breast cancer cells (Abdel-Ghany, M., et al., *J Biol Chem* 276: 25438-25446 (2001); Elble, R. C., et al., *J Biol Chem* 272: 27853-27861 (1997)). Most recently, the secreted chemokine, CXCL12, which is highly expressed in the lung, liver, and lymph nodes, was shown to bind to CXCR4 receptors on the surface of metastasizing breast cancer cells (Muller et al., 2001). Moreover, interfering with only one of these interactions was sufficient to inhibit metastasis (Abdel-Ghany, M., et al., *J Biol Chem* 276: 25438-25446 (2001); Cheng, H. C. et al., *J Biol Chem* 273: 24207-24215 (1998); Muller, A., et al., *Nature* 410: 50-56 (2001)). Although there is no evidence available on the significance of these interactions in breast cancer, it seems that multiple interactions of cell adhesion molecules and growth factor receptors may be required for the attachment and growth of circulating tumor cells. Similar mechanisms based on unique vascular addresses may play a role in organ-specific metastasis to other organs.

Others have identified numerous genes, whose expression are increased in metastatic breast cancer. One such gene, described as GenBank™ entry AK000745 was up-regulated in metastatic breast cancers, along with many other genes (Van't Veer, et al., *Nature* 415: 530-536 (2002). However, the possibility of a causal role of this gene or its protein product (herein named metadherin) in breast cancer metastasis has not yet been established.

SUMMARY OF INVENTION

Aspects of the invention relate to variants of metadherin and the nucleic acids and polypeptides that encode metadherin. These polypeptides and nucleic acids are useful for modulating and diagnosing tumor metastasis. Metadherin polypeptides and nucleic acids can be advantageously used to diagnose or treat cancer, in particular breast cancer and lung cancer.

Furthermore, metadherin polypeptides and nucleic acids encoding metadherin can be useful to screen for agents that can alter metadherin activity or expression. In addition, these nucleic acids and proteins can be used to discover useful general agents and binding agents, such as small molecule drugs, peptides, antibodies, anti-sense nucleic acids, or small interfering RNA, each of which can affect tumor metastasis.

Some embodiments of the invention may also include vectors containing metadherin nucleic acids, host cells containing such vectors, metadherin anti-sense nucleic acids and related compositions.

Other embodiments of the invention include a molecule which is able to localize desired substances to the lung tissue. In one embodiment, the localizing molecule is a fragment of metadherin. In another embodiment, the molecule includes amino acids 378-440 of metadherin.

Yet other embodiments are oligonucleotides that hybridize to, or amplify, a metadherin nucleic acid.

Other embodiments are anti-metadherin specific antibodies and the use of these antibodies to treat metastatic cancer. Further provided are kits containing metadherin nucleic acids or metadherin specific antibodies, such kits and reagents can be used to diagnose cancer, monitor response to therapy, or predict the prognosis of a cancer patient.

Also provided are methods of modulating tumor metastasis using metadherin polypeptides, encoding nucleic acids, compounds, or agents that modulate the activity or expression of metadherin polypeptides. The methods for modulating tumor metastasis can be used to treat diseases such as cancer.

Other embodiments provide methods of therapy involving administering antisense nucleotides directed to the metadherin sequence. Further provided are methods of treating a patient involving administering, to a patient, antisense nucleotides that are directed to the metadherin sequence.

Other embodiments provide methods of reducing metadherin mediated localization by administering an antibody that is directed to metadherin.

Other embodiments provide methods of reducing the expression of metadherin by administering siRNA directed to the metadherin sequence to a sample. Further provided is a method for helping a patient with cancer by administering an effective amount of siRNA to the patient in order to reduce the level of expression of metadherin on the metastatic cells.

Other embodiments provide methods for imaging a cancer in a subject.

BRIEF DESCRIPTION OF THE DRAWINGS

FIG. 1 shows the sequence of the lung-binding domain and structural information of metadherin protein.

FIG. 1A shows an amino acid sequence of metadherin's lung-homing domain. This domain corresponds to residues 378-440 of the full-length mouse metadherin protein.

FIG. 1B shows a hydrophobicity analysis of metadherin, using a window size of 9 amino acids.

FIG. 1C shows a layout of the full-length metadherin protein.

FIG. 2 shows an alignment performed on BLAST of human metadherin and several metadherin homologs.

FIG. 4 shows that the lung-homing domain of metadherin is extracellular.

FIG. 7 shows that anti-metadherin antibodies and siRNA reactive to metadherin mRNA inhibit lung metastasis.

DETAILED DESCRIPTION OF THE INVENTION

Figure 3:
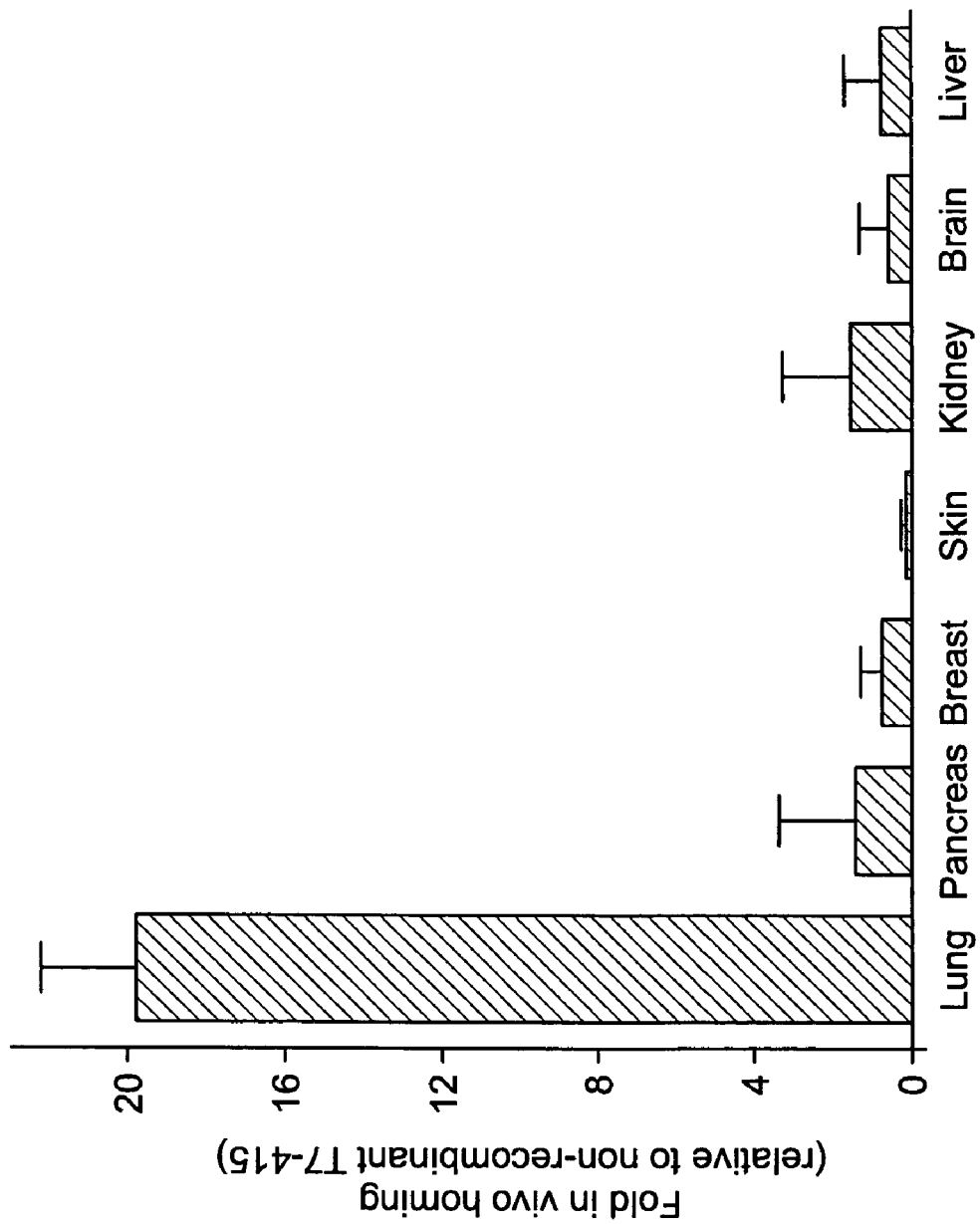
FIG. 3 is a graph showing metadherin phage titers recovered from lung, pancreas, breast, skin, kidney, brain, and liver after injection into the tail-vein of Balb/c mice and circulation for 5 minutes.

As disclosed herein, metadherin and functional fragments thereof were characterized and discovered to be cell-surface proteins that particularly recognize lung vasculature and are involved in the metastasis of tumors. One functional fragment is shown in SEQ ID NO: 3 and corresponds to amino acids 378-440 of murine metadherin (SEQ ID NO: 1). As disclosed herein, metadherin was found to be over-expressed in metastatic breast tumors and bound to the lung vasculature through a C-terminal segment in the extracellular domain. Accordingly, methods and compositions are provided for inhibiting tumor metastasis by inhibiting the expression or function of metadherin. Methods and compositions are also provided for inhibiting the binding of metadherin to its receptor in the lung vasculature.

Some embodiments of the invention include isolated murine metadherin protein (SEQ ID NO: 1) or isolated DNA (SEQ ID NO: 2) encoding the metadherin protein, as well as the human homologs (SEQ ID NO: 13 and SEQ ID NO: 16). In addition, embodiments of the invention include isolated polypeptides and functional variants thereof, the nucleic acid molecules encoding such polypeptides and variants, and related compositions and methods. Other embodiments include methods and compositions for inhibiting the activity or expression of metadherin. Compositions for modulating the activity or expression of metadherin can include, but are not limited to, metadherin, variants thereof, antibodies, siRNA, antisense molecules, peptides, proteins, or small molecules.

Methods are provided herein to identify compounds that modulate, either positively or negatively, the activity or expression of metadherin. Embodiments of the invention also include oligonucleotides that can be used to hybridize to or amplify a metadherin nucleic acid. Embodiments of the invention also include kits containing metadherin nucleic acids or metadherin specific antibodies. Such kits and reagents can be used to diagnose cancer, monitor response to therapy, or predict the prognosis of a cancer patient.

Another embodiment of the invention is a method for inhibiting tumor metastasis. The method includes selecting a patient who has a risk of tumor metastasis and administering an effective amount of a compound that inhibits the binding of metadherin or a variant or fragment thereof, to the metadherin receptor. The selection of a patient may be done in many alternative ways. For example, the type of cancer that a patient has may indicate the likelihood of the cancer's spread. In one embodiment, any patient with cancer, or with a substantial risk of getting cancer, may be the subject of this treatment. In another embodiment, the identification of the patient is achieved by using the method of the current embodiments, such as detecting the presence of excess metadherin, as described more fully below. In one embodiment, the compound comprises a binding fragment of metadherin, such as the murine lung homing domain (SEQ ID NO: 3) or the corresponding domain (SEQ ID NO: 17) from amino acids 378-440 of the human metadherin protein (SEQ ID NO: 13). In an alternative embodiment, the compound may be a monoclonal antibody that preferentially binds metadherin. In an alternative embodiment, the compound may be a peptide, where the peptide binds either to metadherin or to a receptor of metadherin. In one embodiment, the compound may be a variant of metadherin. In one embodiment, the compound may be a peptidomimetic, where the peptidomimetic binds either to metadherin or to a receptor of metadherin. In an alternative embodiment, the compound may be an antisense or siRNA molecule that inhibits expression of metadherin. In an alternative embodiment, the compound may be a small molecule drug.

The compounds can be delivered to locations depending upon the compounds' properties, as will be appreciated by one of skill in the art. For example, antibodies, peptides to metadherin, antisense mRNA, siRNA and receptors can be delivered to the location of the present cancer. Likewise, peptides that bind to the receptor or metadherin, antibodies, receptors or fragments thereof, and metadherin or variants thereof, may be delivered to the location to which the cancer may spread. In one embodiment, the cancer is breast cancer. In one embodiment, the receptor for metadherin is located on the lung vasculature.

Methods are described below for the treatment of a patient suffering from breast cancer, or at risk of breast cancer. In one embodiment, antibodies directed to metadherin are administered to a patient in order to prevent the metadherin molecules on the cancerous cells from metastasizing. In one embodiment, the antibodies preferentially, specifically or selectively bind to metadherin. In one embodiment, the antibodies are directed to the lung-binding domain of metadherin, such as the murine lung binding domain (SEQ ID NO: 3) or the corresponding human lung binding domain (SEQ ID NO: 17). In another embodiment, antisense RNA for metadherin is administered to the patient in order to reduce the expression of metadherin on the cancerous cells and thus reduce metastasis. In another embodiment, siRNA, directed to metadherin, is administered to a patient in order to reduce the level of expression of metadherin in the cancerous cells. In one embodiment, the compound is metadherin, a variant of metadherin, or a fragment of metadherin. In one embodiment, the compound is a peptide derived from metadherin, or a peptidomimetic thereof.

Functional fragments of metadherin, methods of making the functional fragments, and methods of using the functional fragments are also described below. In one embodiment, the functional fragments of the metadherin protein are used as homing agents in order to deliver a desired substance to the lungs. In one preferred embodiment, the functional fragment is a lung-binding domain, such as shown in SEQ ID NO: 3 or SEQ ID NO: 17. In another embodiment the functional fragment is a variant of the lung-binding domain. The functional fragments may be expressed on cells; and the cells thereby become specifically localized to the lung tissue. The possible lung-homing domain of metadherin is displayed in FIG. 1A. FIG. 1B displays the predicted hydrophobicity of the protein. FIG. 1C provides additional structural information concerning the metadherin protein. "TM" denotes the location of the putative transmembrane domain. The numbers denote the position of amino acids in the metadherin protein.

In another embodiment, the functional fragments are attached to a protein or drug of interest. In a more preferred embodiment, these fragments, which are attached to a desired substance, are administered to a patient and the fragments home to the lung tissue, delivering the protein or drug of interest primarily to the lung tissues. In one embodiment, the lung binding domain has the amino acid sequence supplied in SEQ ID NO: 3 or SEQ ID NO: 17. In one embodiment, the compound or compositions may be administered intravenously.

In an alternative embodiment, functional fragments of metadherin are used to compete with and block the metadherin receptors that reside on lung tissue. In a preferred embodiment, the functional fragments comprise the lung-binding domain of metadherin, as shown in SEQ ID NO: 3 or SEQ ID NO: 17. In another preferred embodiment, the functional fragments are variants of metadherin that prevent metastasis by binding to the metadherin receptor.

In one embodiment, metadherin functional fragments are used to block the spread of a cancer. The functional fragments described above, which prevent the association of metastatic cells with the lung tissue, are administered to the patient's lung tissue where they can bind to the metadherin receptors.

In some embodiments, a method for diagnosing metastatic cancer in a patient is supplied. In some of these embodiments, a patient having a tissue suspected to be at risk for metastatic spread of a cancer is selected. A determination is then made whether the tissue that is at risk of metastasis is expressing a higher level of metadherin than normal tissue. A higher expression level of metadherin is indicative of metastatic cancer. In other embodiments, binding agents that bind to metadherin are used as a diagnostic to detect the presence of cancer. The localization of a metadherin binding agent at a specific location in a tissue can indicate that the tissue has a possible cancerous area. In some embodiments, the binding agent is a small peptide that binds to metadherin. In another embodiment, the binding agent is a receptor for metadherin. In other embodiments, the level of metadherin expression in the tissue is examined by applying an antibody that preferentially binds metadherin. Preferably, the antibody is labeled with a radioactive or colorometric label so that it can be easily detected. It should be noted that this method can be performed on a tissue in vivo or in vitro. While any patient may benefit from this examination, there are options for narrowing which patients to test. In one embodiment, the selection may be done by family history. In another embodiment it may be determined by a correlation between cancers and risk of cancer spread, any risk greater than 10% may be considered to result in a patient at risk. In an alternative embodiment, any risk greater than 1% may be considered "at risk." As will be appreciated by one of skill in the art, the damaging effects of the cancer may also be a factor to consider.

In one preferred embodiment, a phage expression library of cDNAs from metastatic breast carcinoma is used to identify protein domains that bind to the vasculature of the lung, a frequent site of breast cancer metastasis.

Definitions

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a polynucleotide in a generally one-to-one manner. An mRNA molecule corresponds to an HnRNA and polynucleotide from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The compositions and methods of the present invention also encompass variants of the above polypeptides and polynucleotides. Such variants include, but are not limited to, naturally occurring allelic variants of the inventive sequences.

A metadherin "variant," as used herein, is a polypeptide, polynucleotide, or molecule that differs from the recited polypeptide or polynucleotide, but only such that the activity of the metadherin protein is not detrimentally altered. In a preferred embodiment, the ability of the metadherin variant to bind to the metadherin receptor(s) is not detrimentally altered. In one preferred embodiment, the variant metadherin molecule comprises or encodes for at least amino acids 378-440 of the metadherin protein, but not the entire protein sequence in SEQ ID NO: 1. In another preferred embodiment, variant metadherins differ from the wild-type sequence by substitution, deletion or addition of five amino acids or fewer. Such variants may generally be identified by modifying one of the above polypeptide sequences, and evaluating the metastasis preventing properties of the modified polypeptide using, for example, the representative procedures described herein. Polypeptide variants preferably exhibit at least about 70%, more preferably at least about 90%, more preferably at least about 95%, and most preferably at least about 99% identity (determined as described below) to the identified polypeptides. In a further preferred embodiment, the variant differs only in conservative substitutions and/or modifications.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also contain other modifications, including the deletion or addition of amino acids, the alterations have minimal effect on the lung-binding domain. In a preferred embodiment, the alterations have minimal influence on the metastasis preventing properties, secondary structure and hydropathic nature of the metadherin polypeptide. For example, a metadherin polypeptide may be conjugated to a signal (or leader) sequence at the N-terminal end of the protein that co-translationally or post-translationally directs transfer of the protein. The metadherin polypeptide may also be conjugated to a linker or other sequence for ease of synthesis, purification or identification of the metadherin polypeptide (e.g., poly-His), or to enhance binding of the metadherin polypeptide to a solid support. For example, a metadherin polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (DNA, 2:183, 1983). Nucleotide variants may be naturally occurring allelic variants, or non-naturally occurring variants. Variant nucleotide sequences preferably exhibit at least about 70%, 75%, 80%, 85%, 90% and most preferably at least about 95% identity (determined as described below) to the recited sequence.

The functional fragments of the peptides provided by in one preferred embodiment include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include prewashing in a solution of 5×SSC; 0.5% SDS, 1.0 mM EDTA (pH 8:0); hybridizing at 50° C.-65° C., 5×SSC, overnight or, in the event of cross-species homology, at 45° C. with 0.5×SSC followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode an metadherin polypeptide that is encoded by a hybridizing DNA sequence.

In alternative embodiment, a homolog is one that can be aligned via a BLAST alignment and is as homologous to metadherin as one of the sequences already aligned in FIG. 2. In a preferred embodiment, the new sequence is a homolog if, following alignment of the sequence with the metadherin sequence, there are fewer variations between the potential homolog and metadherin than there are between the metadherin sequence described herein and all of those listed in FIG. 2. In one embodiment the metadherin is a human metadherin. In an alternative embodiment, the metadherin is a mouse metadherin. As will be appreciated by one of skill in the art, FIG. 2, and similar figures, may also be used to identify functional domains of the metadherin protein. In one embodiment, domains of the protein that are homologous across species are important domains and may be useful for alternative "lung-binding" domains or other signaling functions. In a more preferred embodiment, domains that are identical across organisms in different classes are important domains. Thus, by this type of comparison, one may easily identify alternative functional domains of metadherin, of which the lung-binding domain is one example. In one embodiment, domains that are as similar as the four sequences presented in FIG. 2 are to one another, over the lung-binding domain, are considered homologous, and thus potential functional fragments. One may then use the additional methods disclosed in the present specification to readily test the selected domains for functional activity.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

In one embodiment, alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, *National Biomedical Research Foundation*, Washington D.C. Vol. 5, Suppl. 3, pp. 345-358; Hein J. (1990) Unified Approach to Alignment and Phylogenes pp. 626-645 *Methods in Enzymology vol.* 183, Academic Press, Inc., San Diego, Calif.; Higgins, D. G. and Sharp, P. M. (1989) Fast and sensitive multiple sequence alignments on a microcomputer *CABIOS* 5:151-153; Myers, E. W. and Muller W. (1988) Optimal alignments in linear space *CABIOS* 4:11-17; Robinson, E. D. (1971) *Comb. Theor* 11:105; Santou, N. Nes, M. (1987) The neighbor joining method. A new method for reconstructing phylogenetic trees *Mol. Biol. Evol.* 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Rapid similarity searches of nucleic acid and protein data banks *Proc. Natl. Acad. Sci. USA* 80:726-730. There are many options for alignment another option would be that offered by the ncbi webpage, bl2seq.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Functional metadherin protein or metadherin fragments described herein may be created in any number of ways. They may be isolated from tissue, as described in the Examples. Alternatively, they may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149-2146, 1963). Equipment for automated synthesis of polypeptides is commercially available from suppliers such as Perkin Elmer/Applied BioSystems Division (Foster City, Calif.), and may be operated according to the manufacturer's instructions.

Alternatively, any of the above polypeptides may be produced recombinantly by inserting a DNA sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli*, yeast or a mammalian cell line, such as CHO cells. The DNA sequences expressed in this manner may encode naturally occurring polypeptides, portions of naturally occurring polypeptides, or other variants thereof.

Another embodiment includes mimetics of the metadherin protein. In a more preferred embodiment, the mimetic is of the lung-binding domain of the protein. By "mimetic," it is meant that the functional structure of the lung-binding domain, is the same as the metadherin lung-binding domain. Mimetics may be determined by the same process that the original metadherin protein was discovered, as described in the present specification. Alternatively, mimetics may be created by sequence analysis and structural predictions, wherein predicted, or actual, protein structures for the metadherin lung-binding protein are used as a blueprint to create alternative mimetics of the lung-binding domain. Alternatively, the mimetics may not be structurally similar, but are only functionally similar and may comprise small molecule drugs.

In one embodiment, the mimetics are small molecules and are functionally similar to the lung-binding domain of metadherin. Given the present disclosure, one of skill in the art could determine whether a particular small molecule was a mimetic of the lung-binding domain, simply by repeating the procedure described herein and determining if the small molecule either bound in a similar fashion as the lung-binding domain, or if the mimetic had the same effect on metastasis, as the lung-binding domain. In one embodiment, these small molecules that mimic the activity of metadherin may be used to treat a patient, just as the lung-binding domain itself, as discussed herein, may be used to treat a patient. In an alternative embodiment, the small molecules that mimic the activity of metadherin may be used as a diagnostic aid, in a manner similar to how the lung-binding portion of metadherin can be used to diagnose cancer, as described herein.

In one embodiment, the mimetics are peptides or peptidomimetics, including bifunctional peptides, multivalent peptides and peptidomimetics, and homing peptides and peptidomimetics discussed further below. As used herein, the term "peptide" is used broadly to mean peptides, proteins, fragments of proteins, and the like. The term "peptidomimetic," as used herein, means a peptide-like molecule that has the activity of the peptide upon which it is structurally based. In one embodiment, such peptidomimetics include chemically modified peptides, peptide like molecules containing non naturally occurring amino acids, and peptoids and have an activity such as selective homing activity of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803 861).

A variety of peptidomimetics are known in the art including, as a matter of example, peptide like molecules which contain a constrained amino acid, a nonpeptide component that mimics peptide secondary structure, or an amide bond isostere. Another example is a peptidomimetic that contains a constrained, non naturally occurring amino acid, for example, an α methylated amino acid; α,α dialkylglycine or α aminocycloalkane carboxylic acid; an Nα Cα cyclized amino acid; an Nα methylated amino acid; a β or γ amino cycloalkane carboxylic acid; an α,β unsaturated amino acid; a β,β dimethyl or β methyl amino acid; a β substituted 2,3 methano amino acid; an N Cδ or Cα Cδ cyclized amino acid; a substituted proline or another amino acid mimetic. Another example is a peptidomimetic that mimics peptide secondary structure, for example, a non peptidic β turn mimic; γ turn mimic; mimic of β sheet structure; or mimic of helical structure, each of which is well known in the art. Another example is a peptidomimetic that can also be a peptide like molecule that comprises, for example, an amide bond isostere such as a retro inverso modification; reduced amide bond; methylenethioether or methylene-sulfoxide bond; methylene ether bond; ethylene bond; thioamide bond; trans olefin or fluoroolefin bond; 1,5 disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. As an example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a peptide of the invention, as well as potential geometrical and chemical complementarity to a target molecule. Where no crystal structure of a peptide of the invention or a target molecule that binds the peptide is available, a structure can be generated using, for example, the program CONCORD (Rusinko et al., J. Chem. Inf. Comput. Sci. 29:251 (1989)). Another database, the Available Chemicals Directory (Molecular Design Limited, Information Systems; San Leandro Calif.), contains about 100,000 compounds that are commercially available and also can be searched to identify potential peptidomimetics of a peptide of the invention, for example, with activity in selectively binding to metadherin, variants thereof or the metadherin receptor.

In one embodiment, an isolated peptide or peptidomimetic, or a homing molecule, as will be discussed further below, can be cyclic or otherwise conformationally constrained. As used herein, a "conformationally constrained" molecule, such as a peptide or peptidomimetic, is one in which the three dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization as discussed further below.

As used herein in reference to a peptide or peptidomimetic, the term "cyclic" means a structure including an intramolecular bond between two nonadjacent amino acids or amino acid analogues. The cyclization can be effected through a covalent or noncovalent bond. Intramolecular bonds include, but are not limited to, backbone to backbone, side chain to backbone and side chain to side chain bonds. A preferred method of cyclization is through formation of a disulfide bond between the side chains of nonadjacent amino acids or amino acid analogs. Residues capable of forming a disulfide bond include, for example, cysteine (Cys), penicillamine (Pen), β,β pentamethylene cysteine (Pmc), β,β pentamethylene β mercaptopropionic acid (Pmp) and functional equivalents thereof.

A peptide or peptidomimetic also can cyclize, for example, via a lactam bond, which can utilize a side chain group of one amino acid or analog thereof to form a covalent attachment to the N terminal amine of the amino terminal residue. Residues capable of forming a lactam bond include aspartic acid (Asp), glutamic acid (Glu), lysine (Lys), ornithine (Orn), α,β diamino-propionic acid, γ amino adipic acid (Adp) and M (aminomethyl)benzoic acid (Mamb). Cyclization additionally can be effected, for example, through the formation of a lysinonorleucine bond between lysine (Lys) and leucine (Leu) residues or a dityrosine bond between two tyrosine (Tyr) residues. One of ordinary skill in the art understands that these and other bonds can be included in a cyclic peptide or peptidomimetic of the invention.

In another embodiment, the present invention provides for metadherin or variants thereof, to be associated with and direct the localization of a desired substance. The "desired substance" can be any anything that associates with the metadherin protein. In one preferred embodiment, fusion proteins comprising a metadherin and a second polypeptide, the desired substance, are linked together through covalent bonds. In another non-limiting example, cells that are artificially induced to express metadherin on their surface are the desired substance, that are associated with metadherin, by expressing the metadherin on their cell surface. In another embodiment, nanoparticles may be a desired substance attached to the metadherin protein or variant. In another embodiment, nanodevices may be a desired substance attached to the metadherin protein or variant. The methods of making and using the particles and devices is well known in the art. For a review of this technology, see Erkki Ruoslahti, Cancer Cell, August 2002, 97-98.

These particles and devices, connected to the metadherin protein or variant thereof, will then be delivered to the site of interest, by the metadherin protein or variant of this embodiment. For example, as described by Hood et al., (Science, 296:2404-2407 (2002)), a molecule, in this instance a metadherin or variant thereof, may be added to the external surface of the nanoparticle, the result being that wherever the molecule would naturally be directed to, the entire nanoparticle will be directed to and result in the delivery of the nanoparticle's cargo to those localized cells. The cargo may be any compound, for example, it can be protein based, DNA based, RNA based, a binding agent, a therapeutic agent, a diagnostic agent, or any other number of possibilities as discussed herein or as will be appreciated by one of skill in the art.

In another embodiment, viruses may be the desired substance associated with a metadherin protein or variant thereof. In one embodiment, the virus is a vaccinia or other pox virus, retrovirus, or adenovirus. The use of viruses to deliver genetic material for gene therapy is well known in the art, for example, see Panicali et al., (U.S. Pat. No. 5,656,465, Issued Aug. 12, 1997), herein incorporated in its entirety by reference. One embodiment involves metadherin being cloned into a phage vector such as fuse 5 (for example, as described in Ruoslahti et al., U.S. Pat. No. 6,610,651, Issued Aug. 26, 2003, herein incorporated in its entirety by reference), wherein, upon expression, the encoded peptide is expressed as a fusion protein on the surface of the phage, thus directing the localization of the phage to areas with metadherin receptors. In one embodiment, the viruses contain material to allow for gene therapy. The material may either help or kill the diseased cells. In another embodiment, the viruses contain material to allow for the diagnostic imaging of the tumors. Since the level of metadherin will indicate the risk of cancer, the materials need not be involved in detecting the cancer and may simply be a detectable probe, such as green fluorescent protein. However, in another embodiment, the material in the virus may also serve to actually detect the presence of different markers on cells.

In some embodiments, a "linking element" is used to attach the metadherin or metadherin variant to the desired substance. One of skill in the art will recognize that there are many alternatives by which one can connect two molecules. A linking element may be a complex molecule with particular desired characteristics, such as light cleavable bonds, or it could be as simple as a disulfide bond. When another molecule or desired substance is associated with a metadherin or metadherin variant, it results in the formation of a conjugate. The term "conjugate" is meant to denote the association of both the desired substance and another compound or molecule. In one embodiment, it is meant to denote a desired substance associated with metadherin or a metadherin variant. In another embodiment, it is meant to denote a desired substance associated with an antibody to metadherin or a metadherin variant. In another embodiment, it is meant to denote a desired substance associated with a binding agent of metadherin. Conjugates may be additionally defined as described in this specification, or as would be understood by one of skill in the art.

In one embodiment, a DNA sequence encoding a fusion protein of the present invention is constructed using known recombinant DNA techniques to assemble separate DNA sequences encoding the metadherin and second polypeptides into an appropriate expression vector. The 3' end of a DNA sequence encoding the metadherin is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the metadherin and the second polypeptides. As appreciated by one of skill in the art, only a fraction of the metadherin molecule needs to be included in the fusion protein. In a preferred embodiment, only amino acids 378-440 of SEQ ID NO: 1 are used.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., *Proc. Natl. Acad. Sci. USA* 83:8258-8262, 1986; U.S. Pat. Nos. 4,935,233 and 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptide. Similarly, stop codons require to end translation and transcription termination signals are only present 3' to the DNA sequence encoding the second polypeptide. The metadherin polypeptide need not be the first in the nucleotide sequence.

In one embodiment, a second polypeptide, encoded by a second polynucleotide is a means to attach desired substances to metadherin, thus allowing metadherin to direct desired substances to the lungs, even if the desired substances are not nucleotide based. The second polypeptide of this embodiment may either have its own binding ability or may simply be a molecule that is readily bound by other binding entities.

In an alternative embodiment, there is no linker or second polynucleotide involved; however, there is a desired substance. The desired substance has the ability to bind or associate itself with metadherin polypeptide. In a further preferred embodiment, the method by which the desired substance binds itself to metadherin does not block the lung-binding domain of metadherin. In another preferred embodiment, residues 378-440 of metadherin are not blocked by the association of the desired substance with metadherin. By "lung-binding domain," all that is meant is the structure by which metadherin binds to its receptors. Depending upon the context, this structure may be a nucleic acid structure, the amino acid structure or a non protein structure which resembles the three dimensional shape of the lung-binding domain. "Lung-binding domain" does not mean that the domain only binds to receptors located in the lung. In one embodiment, the "lung-binding domain" may bind to similar metadherin receptors located in other organs. In one embodiment, the lung-binding domain may bind to similar receptors in the liver. In one embodiment, the lung-binding domain will also bind to different receptors in the liver. As will be appreciated by one of skill in the art, all of the embodiments herein, which apply to the use of metadherin with the lungs, may also be applied to other organs that also express a effective expression level of a receptor that binds to metadherin. For example, if metadherin or variants thereof, also bind to receptors in the liver, then the metadherin or variants thereof can be used as a diagnostic, as described herein for lung diagnosis, or the metadherin or variants thereof, can be used to stop the spread of a cancer to the liver, as described herein for stopping breast cancer. One of skill in the art will appreciate the changes that must be made for localization to a particular location in the body.

In one embodiment, the desired substance incorporated into a conjugate of the invention is a therapeutic agent. As used herein, the term "therapeutic agent" means a molecule that has one or more biological activities in a normal or pathologic tissue. A variety of therapeutic agents can be included in a conjugate of the invention. In one embodiment, a conjugate of metadherin, or variant thereof, contains a cancer chemotherapeutic agent. As used herein, a "cancer chemotherapeutic agent" is a chemical agent that inhibits the proliferation, growth, life span or metastatic activity of cancer cells. Such a cancer chemotherapeutic agent can be, without limitation, a taxane such as docetaxel; an anthracyclin such as doxorubicin; an alkylating agent; a vinca alkaloid; an anti metabolite; a platinum agent such as cisplatin or carboplatin; a steroid such as methotrexate; an antibiotic such as adriamycin; a isofamide; or a selective estrogen receptor modulator; an antibody such as trastuzumab.

In one embodiment, taxanes are chemotherapeutic agents useful in the conjugates of the invention. Useful taxanes include, without limitation, docetaxel (Taxotere; Aventis Pharmaceuticals, Inc.; Parsippany, N.J.) and paclitaxel (Taxol; Bristol Myers Squibb; Princeton, N.J.). See, for example, Chan et al., J. Clin. Oncol. 17:2341-2354 (1999).

In one embodiment, a cancer chemotherapeutic agent useful in a conjugate of the invention is an anthracyclin such as doxorubicin, idarubicin or daunorubicin. Doxorubicin is a commonly used cancer chemotherapeutic agent and can be useful, for example, for treating breast cancer (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti angiogenic activity (Folkman, Nature Biotechnology 15:510 (1997); Steiner, In "Angiogenesis: Key principles Science, technology and medicine," pp. 449-454 (eds. Steiner et al.; Birkhauser Verlag, 1992)), which can contribute to its effectiveness in treating cancer.

In one embodiment, an alkylating agent such as melphalan or chlorambucil is a cancer chemotherapeutic agent useful in a conjugate of the invention. Similarly, a vinca alkaloid, such as, vindesine, vinblastine or vinorelbine; or an antimetabolite, such as, 5 fluorouracil, 5 fluorouridine or a derivative thereof can be a cancer chemotherapeutic agent useful in a conjugate of the invention.

In one embodiment, a platinum agent is a cancer chemotherapeutic agent useful in the conjugates of the invention. Such a platinum agent can be, for example, cisplatin or carboplatin as described, for example, in Crown, Seminars in Oncol. 28:28-37 (2001). Other cancer chemotherapeutic agents useful in a conjugate of the invention include, without limitation, methotrexate, mitomycin C, adriamycin, ifosfamide and ansamycins.

In one embodiment, a cancer chemotherapeutic agent for treatment of breast cancer, or other hormonally dependent cancers, is an agent that antagonizes the effect of estrogen, such as a selective estrogen receptor modulator or an anti estrogen. The selective estrogen receptor modulator, tamoxifen, is a cancer chemotherapeutic agent that can be used in a conjugate of the invention for treatment of breast cancer (Fisher et al., J. Natl. Cancer Instit. 90:1371 1388 (1998)).

In one embodiment, a therapeutic agent useful in a conjugate of the invention is an antibody such as a humanized monoclonal antibody. As a non-limiting example, the anti epidermal growth factor receptor 2 (HER2) antibody, trastuzumab (Herceptin; Genentech, South San Francisco, Calif.) is a therapeutic agent useful in a conjugate of the invention for treating HER2/neu overexpressing breast cancers (White et al., Annu. Rev. Med. 52:125 141 (2001)).

In one embodiment, a therapeutic agent useful in the invention is a cytotoxic agent. A "cytotoxic agent," as used herein, is any molecule that directly or indirectly promotes cell death. Cytotoxic agents useful in the invention include, without limitation, small molecules, polypeptides, peptides, peptidomimetics, nucleic acid molecules, cells and viruses. As non limiting examples, cytotoxic agents useful in the invention include cytotoxic small molecules such as doxorubicin, docetaxel or trastuzumab; antimicrobial peptides such as those described further below; pro-apoptotic polypeptides such as caspases and toxins, for example, caspase 8; diphtheria toxin A chain, *Pseudomonas* exotoxin A, cholera toxin, ligand fusion toxins such as DAB389EGF, *ricinus communis* toxin (ricin); and cytotoxic cells such as cytotoxic T cells. See, for example, Martin et al., Cancer Res. 60:3218 3224 (2000); Kreitman and Pastan, Blood 90:252 259 (1997); Allam et al., Cancer Res. 57:2615 2618 (1997); and Osborne and Coronado Heinsohn, Cancer J. Sci. Am. 2:175 (1996). One skilled in the art understands that these and additional cytotoxic agents described herein or known in the art can be useful in the conjugates and methods of the invention.

In one embodiment, a therapeutic agent is a therapeutic polypeptide. As used herein, a "therapeutic polypeptide" is any polypeptide with a biologically useful function. Therapeutic polypeptides useful in the invention include, without limitation, cytokines, antibodies, cytotoxic polypeptides, pro apoptotic polypeptides, and anti angiogenic polypeptides. As nonlimiting examples, a therapeutic polypeptide useful in the invention can be a cytokine such as tumor necrosis factor α (TNF α), tumor necrosis factor β (TNF β), granulocyte macrophage colony stimulating factor (GM CSF), granulocyte colony stimulating factor (G CSF), interferon α (IFN α); interferon γ (IFN γ), interleukin 1 (IL 1), interleukin 2 (IL 2), interleukin 3 (IL 3), interleukin 4 (IL 4), interleukin 6 (IL 6), interleukin 7 (IL 7), interleukin 10 (IL 10), interleukin 12 (IL 12), lymphotactin (LTN) or dendritic cell chemokine 1 (DC CK1); an anti HER2 antibody or fragment thereof; a cytotoxic polypeptide including a toxin or caspase, for example, diphtheria toxin A chain, *Pseudomonas* exotoxin A, cholera toxin, a ligand fusion toxin such as DAB389EGF or ricin; or an anti angiogenic polypeptide such as angiostatin, endostatin, thrombospondin, platelet factor 4; anastellin; or one of those described further herein or known in the art (see below). It is understood by one of skill in the art that these and other polypeptides with biological activity can be a "therapeutic polypeptide" useful in the invention.

The term "compound" is meant to denote a broad variety of substances and can encompass, for example, toxins, agents, cytotoxic agents, siRNA, therapeutic agents, antibodies, binding agents, metadherin receptor proteins, metadherin receptor nucleic acid sequence, metadherin amino acid sequence and metadherin nucleic acid sequences, metadherin lung-binding domain, and variants thereof. The particular group or subgroup will depend upon how the term is used.

The term "agent" can denote the presence of a molecule that is to be associated with a metadherin protein or nucleotide sequence. However, in some situations, the term agent also encompasses the protein or nucleic acid sequences of metadherin.

A "test compound" is a compound that can be administered either in vivo, in vitro, in silico, or by another manner, so as to be present when metadherin binds to its receptor. Test compounds can either block the interaction between metadherin and its receptor (either partially or completely), or not interfere with the interaction of metadherin and its receptor. Test compounds can include the above agents, antibodies, siRNA, therapeutics, etc. Successful test compounds will be those that inhibit the functional interaction between metadherin and its receptor. Thus, binding may still occur, but the binding will not be sufficient to allow metadherin to function in metastasis. Alternatively, a successful test compound may effectively prevent the binding of metadherin to its receptor under in vivo conditions and concentrations. Alternatively, binding simply may not occur because there is no or a reduced amount of metadherin which can bind. Examples of successful test compositions can include variants of the lung-binding domain, siRNAs, peptidomimetics, and various agents and therapeutics, for example.

Metadherin

As described in the below and in the examples, a protein that selectively targeted phage to lung tissue was discovered and named "metadherin." A nucleic acid sequence of the protein is shown in SEQ ID NO: 2 (murine) and 16 (human). An amino acid sequence of the protein is shown in SEQ ID NO: 1 (murine) and 13 (human). FIG. 1A displays a metadherin sequence and identifies the putative lung-homing domain in the protein. FIG. 1B demonstrates a hydrophobicity plot of the protein, which suggests various structural features of the protein. By inserting a myc epitope tag into the protein (e.g., as shown in FIG. 1C) the protein was found to have an extra-cellular domain involved in cell adhesion. This domain not only targeted phage to lung tissue, but was also found to localize cells that were over-expressing metadherin to the lung tissue.

High expression of metadherin was found in cultured tumor cells and in both experimental and clinical breast cancers. The high expression of metadherin was selective for cancers in that the expression in normal breast tissue and in other normal tissues was low, as detected with metadherin-specific antibodies.

Immunostaining revealed that metadherin was highly expressed in breast cancer tissue and breast tumor xenografts. As illustrated below, antibodies reactive to a lung-homing domain (SEQ ID NO: 3) of metadherin inhibited experimental lung metastasis, indicating that metadherin expressed on the surface of tumor cells mediated the localization, and possibly the growth, at the metastatic site. Additionally, siRNA-mediated inhibition of metadherin expression in breast cancer cells likewise was discovered to inhibit experimental lung metastasis.

Metadherin appears to detect and target a specific marker of lung vasculature. Phage displaying metadherin accumulated in lung vasculature, suggesting that among the various vascular beds, it primarily binds to lung endothelium. The ability of metadherin phage to specifically target lung vasculature suggests that among the various vascular beds, the metadherin receptor is primarily expressed on lung endothelium.

As such, it has been discovered that metadherin appears to play an important role in cancer metastasis and that compounds and methods that alter metadherin availability can thereby be used to alter and reduce cancer metastasis and the risk thereof.

The importance of metadherin in tumor cell metastasis is not be limited to breast cancer. By use of SAGEmap (Lal, A., et al., *Cancer Res* 59: 5403-5407 (1999); Lash, A. E., et al., *Genome Res* 10: 1051-1060 (2000)), a component of The Cancer Genome Anatomy Project at the National Center for Biotechnology Information, it was determined that metadherin mRNA is significantly over expressed in cancers of the brain and prostate ($P<0.05$). This suggests that metadherin might also play a role in the metastasis of these cancers as well. Thus, the general methods and compositions described in the present specification may be used, not only for breast cancer, but also for any cancer with elevated levels of metadherin.

Metadherin is conserved among mammals, and with the BLAST algorithm (Altschul, S. F., et al., *Nucleic Acids Res* 25: 3389-3402 (1997)), it was determined that there were additional mouse and human metadherin-like molecules in the GenBank™ databases.

In some embodiments, the metadherin protein, or variant thereof, can be expressed in cells that then express metadherin on their surface and thus allow localization of the cells to the lung tissue. In one embodiment, only the lung-binding domain of metadherin need be expressed on the cell to be delivered to the lungs. A simple method to create such homing cells is to make the cells express metadherin, the lung-binding domain of metadherin, or a chimera of metadherin on their cell surface, and then administer the cells to the patient. In an alternative embodiment, the metadherin molecules are not expressed on the cells but are instead associated with the cells. While there are many ways of associating a peptide with a cell, a linker, which binds to the metadherin peptide and to a particular molecule on the cell is one common way of creating such an association. The linker can either bind to particular proteins or molecules on the cell, or it can indiscriminately bind to the cell membrane.

In other embodiments, metadherin or a variant or fragment thereof can be used to stop metastasis. Metadherin peptides can be administered to a patient with lung or breast cancer to stop or reduce the risk of metastasis. The metadherin proteins can be administered in a variety of ways, as discussed below, and can either be administered to the lungs directly or elsewhere, since the metadherin molecules will localize to the lung tissue eventually on their own. The entire metadherin protein need not be administered, as any functional variant will also localize to the lung. The metadherin, or variant thereof, may be administered in the lung tissue in an amount sufficient to block a substantial amount of the metadherin receptors in the lung and thus prevent later metadherin molecules from localizing in the lung tissue. Alternatively, the metadherin receptors or variants thereof may be added to the initial tumor, or lung tissue, in order to bind to the metadherin on the cancerous cells. This in turn prevents the metadherin on the cancerous cells from binding to the receptors on the lung tissue, thereby preventing tumor metastasis to the lungs.

In a preferred embodiment, a lung-binding domain of metadherin is administered to the patient in order to reduce the chances of any nonspecific binding occurring between the fragment and unknown targets in the patient. A "fragment" as used herein is a subset of a "variant." In other words, a variant may include species that are not fragments. In a preferred embodiment, only cell-free metadherin is administered to the lungs, so that the binding of metadherin to the surface of the lung tissue will have a minimal impact on any local tissue. The metadherin or metadherin fragment will localize to the lungs where it will occupy the metadherin receptors present in the lungs and prevent cancer cells, which associate with the lung tissue via the metadherin receptors from localizing to the lung, thus preventing metastasis. As will be appreciated by one of skill in the art, the peptide or full length protein need not be administered as a peptide and can be administered in nucleic acid form to later be expressed in vivo.

In an alternative embodiment, antisense RNA that binds and inhibits translation of metadherin is used to treat metastatic or potentially metastatic tumors. In a preferred embodiment, the RNA is anti-sense RNA that prevents effective production of the metadherin protein. In an alternative embodiment, small interfering RNAs (siRNAs) are used to treat metastatic tumors. The structure and activity of siRNA is reviewed by Bosher et al. (*Nature Cell Biol.* 2:E31, 2000) and C. P. Hunter (*Curr. Biol.* 9:R440, 1999). Such siRNA complexes comprise double-stranded RNA molecules having metadherin sense and antisense polynucleotides that specifically inhibit translation of mRNA encoding metadherin. Kits and instructions for using or creating siRNA are plentiful in the industry and are available at many companies. For example, Ambion (Austin, Tex.) makes several kits for in vitro siRNA production, such as the "Silencer siRNA Construction Kit." As described below, the pSilencer 3.0-H1 plasmid, and an Ambion vector for making siRNA, was used effectively to reduce metastatic breast cancer.

Metadherin, or metadherin variants, including fusion proteins, can be present within a pharmaceutical composition and/or a vaccine. Pharmaceutical compositions may comprise one or more polypeptides, each of which may contain one or metadherins, and a physiologically acceptable carrier. Pharmaceutical compositions may also comprise small molecules, antibodies, peptides, polynucleotides, anti-sense RNA and siRNA.

There can be situations where it is desired to have the body make its own antibodies to metadherin, in order to constantly produce antibodies to block metadherin binding. In such a case, one may use the metadherin molecule, or variant thereof to make a vaccine to metadherin. The vaccines may comprise one or more metadherins and a non-specific immune response enhancer, wherein the non-specific immune response enhancer is capable of eliciting or enhancing an immune response to a metadherin. Examples of non-specific-immune response enhancers include adjuvants, biodegradable microspheres (e.g., polylactic galactide) and liposomes (into which the polypeptide is incorporated). Pharmaceutical compositions and vaccines may also contain other epitopes of breast tumor antigens, either incorporated into a combination polypeptide (i.e., a single polypeptide that contains multiple epitopes) or present within a separate polypeptide.

Alternatively, a pharmaceutical composition or vaccine may contain DNA encoding one or more metadherins, such that the metadherin is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as *Bacillus*-Calmette-Guerrin) that expresses an epitope of a breast tumor cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317-321, 1989; Flexner et. al., *Ann. N.Y. Acad. Sci.* 569:86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *PNAS* 91:215-219, 1994; Kass-Eisler et al., PNAS 90:11498-11502, 1993, Guzman et al., Circulation 88:2838-2848, 1993; and Guzman et al., *Cir. Res.* 73:1202-1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745-1749, 1993, reviewed by Cohen, *Science* 259:1691-1692, 1993. The uptake of naked DNA may be increased by coating the DNA onto biodegradable beads, which are efficiently transported into the cells.

Routes and frequency of administration, as well as dosage, will vary from individual to individual and may parallel those currently being used for other diseases. In general, the pharmaceutical compositions and vaccines may be administered by injection (e.g., intracutaneous, intramuscular, intravenous or subcutaneous), intranasally (e.g., by aspiration) or orally.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

In a further embodiment, the embodiments above are combined in a kit in order to administer either a treatment to stop metastasis, a test to diagnosis the presence or risk of a cancer spreading, or both. In one preferred embodiment, the carriers and the metadherin variants, or the binding agents described below, are combined to provide a pill form, which is then packaged so as to allow for regular dosage for the prevention of cancer metastasis. In one preferred embodiment, a kit for the treatment to stop the metastasis of lung cancer would include multiple embodiments of the invention. It could include a metadherin based device to prevent metastasis, such as a fragment of metadherin, and a metadherin based device to detect the amount the amount of native metadherin remaining in the system, perhaps an antibody detection system directed against metadherin.

In a different embodiment, the conjugates and therapeutic agents discussed above, and the binding agents discussed below, can be used in methods of imaging tumor metastasis. In one embodiment, the binding agents also block the binding of metadherin to its receptor.

The conjugates and agents can be useful for detecting the presence of metastasized tumor cells associated with a variety of tumors, including breast, ovarian, brain, colon, kidney, lung, liver, bladder and prostate tumors and melanomas. Following administration of an agent or conjugate containing a detectable agent, tumor metastasis is visualized. If the image is positive for the presence of tumor metastasis, the tumor can be evaluated for further treatment. These results provide valuable information to the clinician with regard to the stage of development of the cancer and the presence or probability of metastasis.

In one embodiment, a method of imaging tumor lymphatic vasculature is provided. The conjugate or agent administered contains a detectable agent that allows detection or visualization of vasculature in and around tumors, for example in and around breast tumors. For in vivo diagnostic imaging of tumor metastasis, a peptide or other agent which binds to metadherin, variant thereof, or the metadherin receptor is linked to a detectable agent that, upon administration to the subject, is detectable external to the subject. In one embodiment, such a detectable agent may be, for example, a gamma ray emitting radionuclide such as indium 113, indium 115 or technetium 99; following administration to a subject, the conjugate or agent may be visualized using a solid scintillation detector.

A variety of detectable agents are useful in the methods of the invention. As used herein, the term "detectable agent" refers to any molecule that can be administered in vivo and subsequently detected. In one embodiment, detectable agents useful in the imaging methods of the embodiment include, but are not limited to, radioactive agents and colorometric agents. Exemplary radioactive agents include indium 111, technetium 99, carbon 11, and carbon 13. Fluorescent molecules useful in the invention encompass, without limitation, fluorescein, allophycocyanin, phycoerythrin, rhodamine, and Texas red.

In another embodiment, the agents- and conjugates used in this method comprise a mimic to the lung-binding domain of metadherin, as well as the detectable agent.

In one embodiment, metadherin, or variants thereof, may be used to generate binding agents, such as antibodies or fragments thereof. In a preferred embodiment, these binding agents are capable of detecting or preventing the metastasis of human breast or lung tumors. Binding agents of the present invention may generally be prepared using methods known to those of ordinary skill in the art, including the representative procedures described herein. In one embodiment, binding agents are capable of differentiating between patients with and without lung or breast cancer, using the representative assays described herein. In other words, antibodies or other binding agents that bind to metadherin, or a suitable variant thereof, will generate a signal indicating the presence of lung or breast cancer. In a different embodiment, the emphasis of the binding agent is not in distinguishing between the presence or absence of cancer, but in how efficiently the binding agent binds to metadherin.

The ability of metadherin or metadherin variants to generate antibodies capable of detecting tumors may generally be evaluated by raising one or more antibodies against metadherin, or a metadherin variant, and determining the ability of the antibodies to detect tumors in patients. This determination may be made by assaying biological samples from patients with and without cancer for the presence of metadherin that is bound by the generated antibodies. Such test assays may be performed, for example, using a representative procedure described below. Antibodies capable of detecting tumors by such procedures are considered useful. In a further preferred embodiment, metadherin variants or fragments that generate antibodies capable of detecting at least 20% of tumors by such procedures are considered to be very useful in assays for detecting metastatic human lung or breast tumors. Antibodies may be used alone or in combination to improve sensitivity.

Metadherin may be used as a marker for diagnosing cancer or for monitoring disease progression in patients. In one embodiment, cancer in a patient may be diagnosed by evaluating a biological sample obtained from the patient for the level of metadherin; relative to a predetermined cut-off value. As used-herein, suitable "biological samples" include blood, sera, urine, as well as the more traditional tissue samples. In a preferred embodiment, the sample is a lung tissue sample.

The level of metadherin may be evaluated using any binding agent that is specific for metadherin. A "binding agent," in the context of the invention, is any agent (such as a compound or a cell) that binds to metadherin. As used herein, "binding" refers to an association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In a preferred embodiment, two compounds are said to "bind" in the context of the present invention when the binding constant for complex formation exceeds about $10^3$ L/mol. The binding constant may be determined using methods well known to those of ordinary skill in the art. Binding may either be covalent, such as with the formation of disulfide bonds, or it may be non-covalent.

Any agent that satisfies the above requirements may be a binding agent. For example, a binding agent may be a ribosome with or without a peptide component, an RNA molecule or a peptide. The binding agents of the present embodiments need not bind exclusively to metadherin. In one embodiment, the binding agents preferentially bind to metadherin. By "preferentially" all that is meant is that the binding agent binds to metadherin with a stronger preference than it binds to at least one other target compound. Similarly, if a binding agent is "specific" for metadherin, all that is meant is that the binding agent binds to metadherin with greater specificity than it does to one other material. As will be appreciated by one of skill in the art, the degree of specificity required in any particular application of the binding agents will depend upon many factors, including the other molecules to which the binding agent will be exposed.

In a preferred embodiment, the binding agent is an antibody, or a binding fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect a molecule like metadherin in a sample. See, e.g., Harlow and Lane, Antibodies: A Laboratory Manual, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a metadherin is labeled with a reporter group and allowed to bind to the immobilized binding partner after incubation of the binding partner with the sample. The extent to which components of the sample inhibit the binding of the labeled metadherin to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but in a preferred embodiment is typically between about 1 hour and about 1 day. In general, contacting a well of a plastic microtiter plate (such as polystyrene or polyvinylchloride) with an amount of binding agent ranging from about 10 ng to about 10 microgram, and preferably about 100 ng to about 1 microgram, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides of metadherin, or fragments of metadherin, within the sample are allowed to bind to the immobilized antibody. Unbound sample is then removed from the immobilized metadherin-antibody complexes and a second antibody (containing a reporter group) capable of binding to a different site on metadherin is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or TWEEN 20.™ (Sigma Chemical Co., St. Louis, Mo.). The immobilized antibody is then incubated with the sample, and metadherin, or a fragment thereof, is allowed to bind to the antibody. The sample may be diluted with a suitable diluent, such as phosphate-buffered saline (PBS) prior to incubation. In general, an appropriate contact time is that period of time that is sufficient to detect the presence of metadherin within a sample obtained from an individual with cancer. In a preferred embodiment, the contact time is sufficient to achieve a level of binding that is at least about 95% of that achieved at equilibrium between bound and unbound metadherin. Those of ordinary skill in the art will recognize that the time necessary to achieve equilibrium may be readily determined by assaying the level of binding that occurs over a period of time. As a general guideline, at room temperature, an incubation time of about 30 minutes is generally sufficient.

Unbound sample may then be removed by washing the solid support with an appropriate buffer, such as PBS containing 0.1% Tween 20.™ The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-metadherin complex for an amount of time sufficient to detect the bound metadherin. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the risk of the spread of cancer in a patient, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without cancer. In another preferred embodiment, the cut-off value is determined by the amount of metadherin in the system of one that has cancer, but no spread of cancer has occurred. In one embodiment, when the sample generating the signal is higher than the cut-off value, then there is a risk of metastasis of cancer in that tissue. In a preferred embodiment, a sample generating a signal that is three standard deviations above the predetermined cut-off value is considered positive for a risk of spread of the cancer to that organ. In an alternate preferred embodiment, the cut-off value is determined using a Receiver Operator Curve, according to the method of Sackett et al., Clinical Epidemiology: A Basic Science for Clinical Medicine, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for cancer. In an alternate preferred embodiment, the cut-off value is the average mean signal obtained when the immobilized antibody is incubated with samples from patients with cancer. In this embodiment, the result from the sample examined will be as large or larger than the sample from the known cancer.

In another embodiment, metadherin may be used as a marker for the progression of lung or breast cancer. In this embodiment, assays as described above for the diagnosis of cancer may be performed over time, and the change in the amount of metadherin evaluated. In general, lung or breast cancer is progressing in those patients in whom the level of metadherin detected by the binding agent increases over time. In contrast, lung or breast cancer is not progressing when the level of reactive metadherin either remains constant or decreases with time.

Metadherin, or variants thereof, may also, or alternatively, be used to generate binding agents that are capable of inducing a change in the binding characteristics of metadherin. Such binding agents would allow one to bind to and alter the binding characteristics of the metadherin polypeptide that is already present on the cancerous cells. The result being that the lung-binding domain of the cancerous cell would effectively be neutralized and the cancer would not spread to other sections of the patient, particularly the lungs. In a preferred embodiment, the binding agent blocks the binding ability of metadherin to the metadherin receptor(s). In another preferred embodiment, the binding agents bind to and block the lung-binding domain of metadherin. In an alternative embodiment, the binding agent may actually promote or strengthen the binding of metadherin and its receptor. In order to be perfectly clear on terminology, such binding agents should be referred to as "enhancing binding agents," rather than simply binding agents. In one embodiment, the binding agents are small molecules that bind to and block metadherin binding. In another embodiment, the binding agents are peptides. In another embodiment, the binding agents are antibodies. In one embodiment, the binding agents may be used to either treat or prevent the spread of a cancer. In another embodiment, the binding agents may be used in diagnostic imaging methods, as described herein.

There are many ways to determine if a small molecule, peptide, protein, or antibody has an effect on the binding characteristics of metadherin. In general, the methods described previously concerning detection of metadherin will be useful in observing if the binding characteristics of metadherin have been altered by the binding agent. An example of one such binding agent is demonstrated in the Examples below. In a preferred embodiment, the metadherin protein and possible binding agents are first allowed to bind together to form a complex under conditions that would be appropriate for the desired properties of the final binding agent. This complex is then exposed to metadherin receptors. There are a variety of ways to do this. In one preferred embodiment, the complex is expressed on the surface of a cell and then the cell is injected into an animal to see if it localizes to the lung tissue, in particular, to the metadherin receptors. If the presence of the binding agent reduces the number of cells that are localized to the lungs, then the binding agent will be an effective binding agent that modulates the binding ability of metadherin.

In an alternative preferred embodiment, a similar process will demonstrate if an agent is an effective means for modulating metadherin activity, in other words, is the agent an activity modulating agent. This can be tested for by determining if cancerous cells, expressing metadherin, can still localize to the lungs after or during exposure to the possible activity modulating agent in question.

In one embodiment, a method for screening compounds (e.g., test compounds) that alter tumor metastasis is provided. The embodiment comprises selecting a first test compound, contacting the first test compound in the presence of a metadherin polypeptide, variant, or fragment thereof, and the metadherin receptor, and then determining whether the first compound affects the binding of the metadherin polypeptide, variant or fragment to the metadherin receptor. In an alternative embodiment, the effect to be observed may be to determine if tumor metastasis occurs, rather than simply looking for binding of the compound to the metadherin receptor. In one embodiment, the metadherin receptor is located on the lung vasculature.

In a further embodiment, it may be desired to distinguish between agents in the above embodiments, that is, to determine if the agent is a binding agent, reducing metadherin localization by blocking the binding of metadherin to a receptor, or if the agent is an activity modulating agent, reducing localization by, perhaps, less direct means. These are not necessarily distinct groups as activity reducing agents may encompass binding agents as well. However, as appreciated by one of skill in the art, there are many methods in the art to help distinguish between direct binding reactions and perhaps a cascade of reactions that is brought to a stop. A simple example would employ surface plasmon resonance, for example with a BiaCORE™ 2000 surface-plasmon-resonance device (BIAcore, Inc., Piscataway, N.J.) in order to observe if the presence of the agent prevents binding by metadherin receptors; a source of said receptors would be lung cells identified in the current patent. Additionally, various reagents to stop well-known cascades as well as the kinetics of the binding process, will all indicate which type of agent one has discovered. However, it will often not be necessary to distinguish between these two agents.

In an alternative preferred embodiment, the method can be adjusted to determine if possible expression-modulating agents can modulate the expression of metadherin. In this embodiment, localization of cells transformed with metadherin, with and without the possible expression-modulating agents are injected into a host and monitored for localization to the lungs. In this situation, it is important that the agents be given enough time to actually influence expression of metadherin, and that the agents are removed from the cell sample before injection into the host to remove false positives that merely signify the presence of binding agents. If the expression-modulatingagents have an impact on the percent of cells that localize to the lungs for the metadherin expressing cells, but not a significant effect on the localization of cells not expressing metadherin, then the agent will be classified as an expression-modulating agent.

The small molecules, peptides, proteins, or antibodies derived from the above screens, as well as the method of using them to prevent metastasis are also embodiments of this invention.

In another embodiment, cells expressing metadherin are used to screen for their ability to bind to a library of cells, wherein the library expresses DNAs that encode for potential metadherin receptor proteins. Creating a library of cells and analyzing the results can be performed in a variety of ways known to those of skill in the art. For example, once potential metadherin receptors are cloned, antibodies to the receptors can be created in manner as described for metadherin. The antibodies can then be used to assay which of the potential metadherin receptors is an actual receptor.

Antibodies for use in the above methods may be prepared by any of a variety of techniques known to those of ordinary skill in the art. See, e.g., Harlow and Lane, Antibodies: A Laboratory Manual, Cold Spring Harbor Laboratory, 1988. In one such technique, an immunogen comprising metadherin is initially injected into any of a wide variety of mammals (e.g., mice, rats, rabbits, sheep and goats). In this step, metadherin may serve as the immunogen without modification. Alternatively, a superior immune response may be elicited if the metadherin is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the metadherin may then be purified from such antisera by, for example, affinity chromatography using the metadherin coupled to a suitable solid support.

Monoclonal antibodies specific for metadherin may be prepared, for example, using the technique of Kohler and Milstein, Eur. J. Immunol. 6:511-519, 1976, and improvements thereto. Briefly, these methods involve the preparation of immortal cell lines capable of producing antibodies having the desired specificity (i.e., reactivity with the metadherin of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against metadherin. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies may also be used as therapeutic reagents, to diminish or eliminate lung or breast tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group that is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody-molecule. In another embodiment, more than one of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the density of metadherin, and the rate of clearance of the antibody.

Diagnostic reagents of the present invention may also comprise DNA sequences encoding metadherin, or one or more portions thereof. For example, at least two oligonucleotide primers may be employed in a polymerase chain reaction (PCR) based assay to amplify metadherin nucleic acids derived from a biological sample, wherein at least one of the oligonucleotide primers is specific for a metadherin gene or RNA. The presence of the amplified cDNA is then detected using techniques well known in the art, such as gel electrophoresis. Similarly, oligonucleotide probes specific for metadherin may be used in a hybridization assay to detect the presence of an inventive metadherin in a biological sample.

As used herein, the term "oligonucleotide primer specific for metadherin" means an oligonucleotide sequence that has at least about 60%, preferably at least about 75% and more preferably at least about 95%, identity to metadherin. Oligonucleotide primers and/or probes that can be usefully employed in the diagnostic methods described herein can have at least about 10-40 nucleotides. The oligonucleotide primers can comprise at least about 10 contiguous nucleotides of a polynucleotide having a sequence shown in SEQ ID NO: 2. Oligonucleotide probes for use in the diagnostic methods can have at least about 15 contiguous oligonucleotides of a polynucleotide with a sequence shown in SEQ ID NO: 2. Techniques for both PCR based assays and hybridization assays are well-known in the art. Primers or probes may thus be used to detect breast tumor-specific sequences in biological samples, including blood, urine and/or breast tumor tissue.

The following Examples are offered by way of illustration and not by way of limitation.

EXAMPLES

Example 1

Identification of the cDNA of Metadherin

This example demonstrates how candidate cell adhesion proteins that mediated breast cancer metastasis were identified using an in vivo phage screening approach. This approach could also be used to find similar proteins or verify that possible metadherin variants are functional in their ability to bind lung cells. The highly metastatic, BALB/c-derived 4T1 mammary tumor cell line was selected to study tumor metastases because 4Ti cells and human mammary adenocarcinomas share similar sites of metastasis (Aslakson, C. J. and Miller, F. R., *Cancer Res* 52: 1399-1405 (1992); Dexter, D. L. et al., *Cancer Res* 38: 3174-3181 (1978); Miller et al., 1983). Human breast cancer typically spreads first to the lungs in 24-77% of the cancers and to the liver in 22-62% (Kamby, C. et al., *Cancer* 59: 1524-1529 (1987); Rutgers, E. J. et al., *Br J Surg* 76: 187-190 (1989); Tomin, R. and Donegan, W. L., *J Clin Oncol* 5: 62-67 (1987)). Similarly, 4T1 cells spread in mice to the lungs in >95% of cases and to the liver in >75% of the cancers (Pulaski, B. A. and Ostrand-Rosenberg, S., *Cancer Res* 58: 1486-1493 (1998)). 4T1, a cell line derived from a BALB/c breast adenocarcinoma, was obtained from ATCC and maintained as described by Pulaski et al. (*Cancer Res* 58: 1486-1493 (1998)). MDA-MB-435 and KRIB cell lines were maintained as described before (Laakkonen, P. et al., *Nat Med* 8: 751-755 (2002)). Nude BALB/c mice were subcutaneously injected with $1 \times 10^6$ 4T1 tumor cells and kept for 5 weeks (KRIB) or 10 weeks (MDA-MB-435). Tumors were then removed, frozen in OCT embedding medium (Tissue-Tek, Elkhart, Ind.), and sectioned. 4T1 cells were used to prepare a cDNA library enriched in transcripts that encode secreted and transmembrane proteins potentially involved in metastasis.

Phage Library and Screening

A cDNA library was prepared from membrane-bound polyribosomal mRNA of 4T1 cells. Briefly, RNA from membrane-bound polysomes of $3.2 \times 10^8$ 4T1 cells was prepared using the methods described by Mechler (1987). Approximately 1 µg of this RNA was used to generate 6 µg of amplified anti-sense mRNA (aRNA), using the methods described by Luo et al. (1999). Using aRNA as template, mRNA was synthesized as described by Luo et al. (1999), except the primer, 5'-TTNNNNNN-3' [SEQ ID NO: 4], was used instead of random hexamer primer, and methylated dNTPs were used instead of dNTPs. A cDNA library was prepared from the mRNA, as described in the manufacturer's protocol (OrientExpress™ Random Primer cDNA synthesis kit; Novagen, Madison, Wis.).

A "stop linker" was inserted into the myc epitope phage vectors described above to prevent myc epitope expression in phage vectors that were unsuccessfully ligated to cDNA during library construction. Oligonucleotides, encoding stop codons in all three reading frames, were synthesized, phosphorylated, annealed, and ligated to EcoRI/HindIII-digested myc epitope phage vectors to form myc-T7 vectors. The cDNA libraries were then ligated to EcoRI/HindIII-digested myc-T7 vectors, phage were packaged, and libraries were amplified. As measured by plaque assay, the library contained $4.7 \times 10^6$ primary recombinants.

T7 phage vectors that expressed myc epitope-tagged inserts of the cDNA in the library were then assembled. Oligonucleotides, encoding myc epitopes in all three reading frames, internal EcoRI and HindIII restriction enzyme cleavage sites, and flanking EcoRI/HindIII adapters were synthesized. The oligonucleotides were then individually phosphorylated, annealed, and ligated to EcoRI/HindIII-digested T7Select 1-2a, 1-2b, or 1-2c vector arms (Novagen) to generate myc epitope phage vectors.

Phage clones that expressed cDNA inserts with open reading frames were enriched by three rounds of selection with an anti-myc mAb (3.1 µg/ml MAB8864; Chemicon, Temecula, Calif.) bound to rat anti-mouse IgG1 magnetic beads (3.1 µl per 1 ml of buffer; Miltenyi Biotec, Auburn, Calif.). Selections were performed with $10^{11}$ pfu of phage in 10 ml of Dulbecco's phosphate buffered saline containing 0.5% bovine serum albumin (PBSB). Phage were applied to a magnetized LS MACS column (Miltenyi Biotec), washed with buffer (50 mM Tris-HCl, pH 7.5, 150 mM NaCl, 1% NP-40, 0.5% sodium deoxycholate, 0.1% sodium dodecyl sulfate), eluted with PBSB after demagnetizing the column, and transferred to a second column for more washes. Phage were amplified using the liquid lysate method after each anti-myc selection round.

Ex vivo and in vivo screenings with the 4T1 cDNA library were performed as previously described (Hoffman et al., in press). The library was pre-selected for phage that bound to lung tissue by performing two rounds of ex vivo selection on single-cell lung suspensions. The pre-selected 4T1 library was then injected intravenously into Balb/c mice and phage that accumulated in lung were isolated. After three rounds of in vivo selections, cDNA inserts were sequenced from 32 phage clones.

Individual phage clones were tested for their ability to specifically bind to lung vasculature. One of the five lung-specific clones identified encoded a fragment of a protein recently deposited into GenBank™ (accession numbers AAL92861 and AAP30791). The selected phage, when intravenously (i.v.) injected into mice and allowed to circulate for five minutes, bound to lungs almost 20-fold more than control phage (FIG. 3, error bars represent mean±s.d. for 2-7 experiments per variable). No selective accumulation of this phage was seen in breast, skin, brain, or liver and its amount was less than 2-fold above control phage in pancreas and kidney. The phage co-localized with blood vessels in the lungs. This was determined via an anti-phage immunostaining of lungs from mice co-injected with fluorescein-labeled tomato lectin and either metadherin phage (T7-metadherin) or T7-415 non-recombinant phage (T7-Control). Control lungs were from non-injected mice (lectin⁻phage⁻), mice injected with lectin alone (lectin⁺phage⁻), and mice only injected with metadherin phage (lectin⁻phage⁺). Anti-phage antibody was detected with Alexa 594 goat anti-rabbit IgG antibody. Nuclei were stained with DAPI. This demonstrates that the protein fragment was an effective means for delivering desired substances to blood vessels in the lungs Cloning of Full-Length Metadherin cDNA The following primers were synthesized to amplify the full-length mouse metadherin cDNA:

(SEQ ID NO: 5)
5'-ACCATGGCTGCACGAAGCTGGCAGGACGAGCTG-3'.

(SEQ ID NO: 6)
5'-TCACGTTTCCCGTCTGGCCTTTTTCTTCTTTTTTA-3'.

RNA was isolated from 4T1 cells using a Total RNA isolation kit (Qiagen, Valencia, Calif.). The metadherin cDNA (SEQ ID NO: 2) was amplified by RT-PCR using a Superscript™ One-Step RT-PCR Kit for Long Templates (according to manufacturer's protocol; Invitrogen, Carlsbad, Calif.) and subcloned into the TOPO-TA vector, pcDNA3.1-V5/His according to the manufacturer's protocol (Invitrogen, Carlsbad, Calif.).

Example 2

Antibodies Against Metadherin

This example demonstrates how to obtain antibodies directed against metadherin, in particular, the lung-homing domain of metadherin. This example also demonstrates that metadherin is localized on the external surface of tumor cells. Anti-T7 phage affinity purified antibody was previously described (Laakkonen, et al., (2002). *Nat Med* 8: 751-755). A polyclonal antibody was generated in New Zealand White rabbits against the recombinant metadherin lung-homing domain (SEQ ID NO: 3) that was fused to glutathione-S transferase. The initial immunization was done in complete Freund's adjuvant and boosters were with incomplete Freund's adjuvant. The antibody was affinity purified on recombinant hexahistine-tagged metadherin$_{(378-440)}$ peptide coupled to SulfoLink Gel (Pierce, Rockford, Ill.) via a cysteine residue added to the amino terminus of the metadherin$_{(378-440)}$ peptide. The tags were added by first subcloning the lung-binding domain into the vector pQE-60 (Qiagen, Valencia, Calif.) using the primers 5'-CCCGC-CATGGGGTTAAATGGTTTGTCTTCTGCTGACCC-3', (SEQ ID NO: 7); and 5'-CCCGAGATCTTTTAGATTTC-CCAGTTGGAAGAGCTCCCTCCCC-3' (SEQ ID NO: 8).

These primers resulted in 6 histidine residues at the C-terminus when expressed in the pQE-60 vector. This construct was then used for subcloning, via PCR, the lung-binding domain with hexahistidine tag into the PGEX4T1 vector (Pharmacia, Piscataway, N.J.), using primers 5'-CCCGG-GATCCGGGTGCGGGTTAAATGGTTTGTCTTC-3' (SEQ ID NO: 9) and 5'-CCCGCTCGAGTTAGTGATGGTGATG-GTGATGAGATCTTTTAG-3'(SEQ ID NO: 10). This resulted in a GST tag at the N-terminus.

Figure 4B:
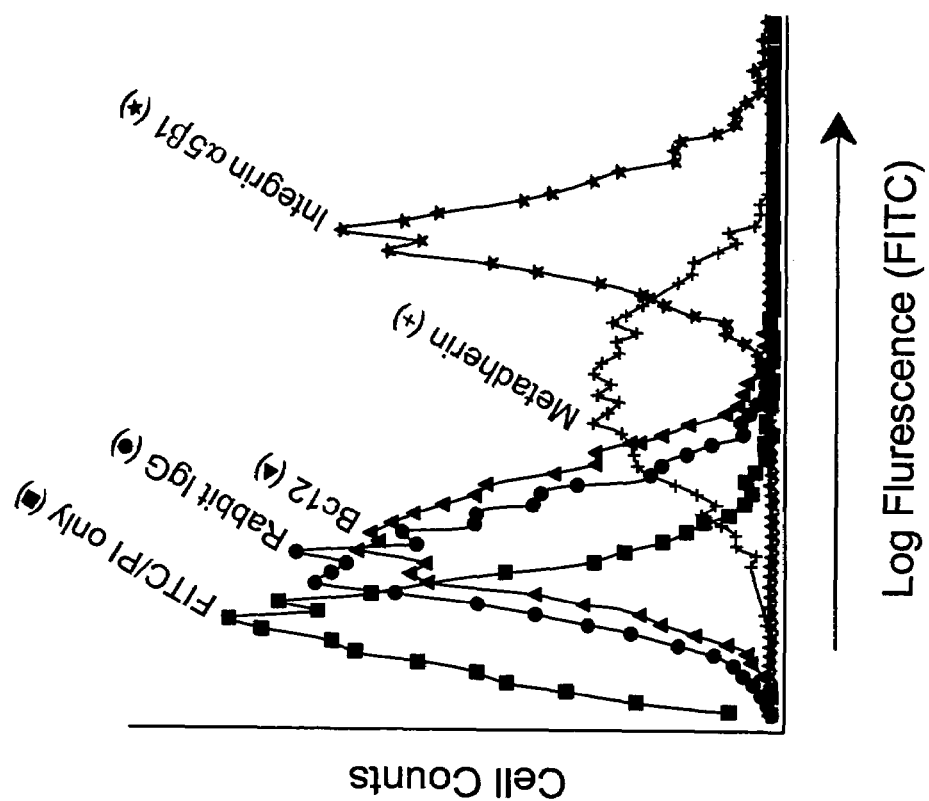
FIG. 4B is a graph that shows Rabbit IgG, anti-Bcl2 polyclonal Ab (Bcl2), anti-integrin α5β1 polyclonal antibody (Integrin α5β1), or anti-metadherin$_{(378-440)}$ (metadherin) as applied to non-permeabilized 4T1 tumor cells and detected with a FITC-labeled secondary Ab.
Figure 4A:
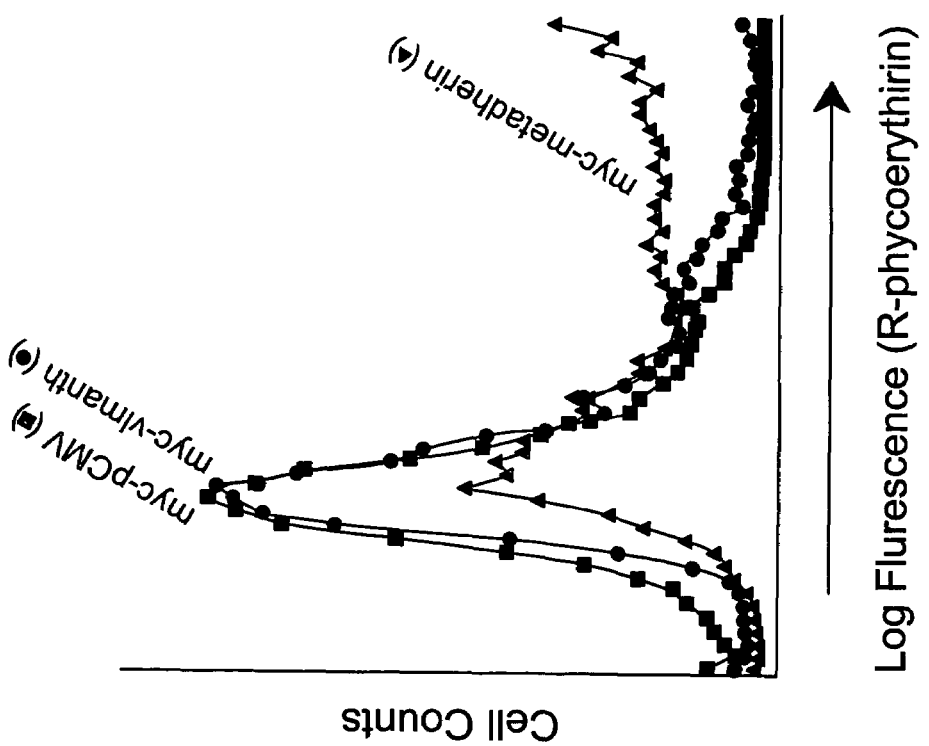
FIG. 4A is a graph that shows HEK293T cells expressing full-length myc-tagged metadherin, myc-vimentin, or myc-pCMV that were analyzed by flow cytometry.

These antibodies bound to non-permeabilized 4T1 cells in flow cytometry (FIG. 4A, anti-myc antibodies were applied to the cells and detected with a PE-labeled secondary Ab). This result confirms the presence of the lung-homing domain of metadherin on tumor cells at the cell surface where it would be available to bind to vascular targets during metastasis. A control antibody against a cytoplasmic protein (Bcl-2) and rabbit IgG did not bind to the surface of non-permeabilized 4T1 cells, while the cells were strongly positive for integrin α5β1 (FIG. 4A, control cells were stained with FITC-labeled secondary Ab and propidium iodide alone (FITC/PI only)).

Example 3

FACS Detection of Metadherin via Metadherin Antibodies

This example demonstrates how to detect the presence of metadherin protein on cells. To analyze the presence of metadherin on 4T1 cells by FACS, the cells were detached from culture plates by incubating with PBS with 2 mM EDTA (PBSE) for 10 minutes. The cells were then washed with PBSB and incubated with 40 μg/ml (in PBSB) of the following antibodies: anti-Bcl2 (SL-492, Santa Cruz Biotechnology, Santa Cruz, Calif.), normal rabbit IgG (Sigma, St. Louis, Mo.), anti-integrin α5β1 (Protein G-purified from rabbit serum containing antibodies raised against human fibronectin receptor), and anti-metadherin$_{(378-4.40)}$. To detect bound antibodies, cells were incubated with goat anti-rabbit IgG-FITC (40 μg/ml in PBSB; Molecular Probes, Eugene, Oreg.). After the final wash, the cells were resuspended with PBS containing 2 μg/ml of propidium iodide (PI) and analyzed by FACS. The antibodies raised against metadherin$_{(378-440)}$ specifically bound to non-permeabilized 4T1 cells in flow cytometry (FIG. 4A). In contrast, the control antibodies against a cytoplasmic protein (Bcl-2) and rabbit IgG did not bind to the surface of non-permeabilized 4T1 cells.

Example 4

FACS analysis of Metadherin via MYC-Metadherin

This example demonstrates an alternative method by which a variant of metadherin can be observed by FACS analysis. A fusion protein, myc-metadherin, which was still able to localize metadherin to the lungs was used in the following experiment. Transiently transfected HEK293T cells expressing myc-vimentin, myc-metadherin, or myc-pCMV vector alone (Clontech, Palo Alto, Calif.) were detached from their culture dishes by gently washing with PBS containing 1% BSA (PBSB). The cells were then stained with mouse anti-myc mAb (2 μg/ml in PBSB; Chemicon, Temecula, Calif.) for 20 minutes at 4° C. The cells were washed with PBSB, stained with goat anti-mouse IgG PE-labeled antibody (4 μg/ml in PBSB; Pharmingen, San Diego, Calif.), washed again with PBSB, fixed with 2% paraformaldehyde in PBS, resuspended in PBS, and analyzed using a FACScan flow cytometer (BD, San Jose, Calif.). It was observed that intact myc metadherin-expressing cells were specifically labeled with anti-myc antibodies (FIG. 4B). However, the cells treated with myc-vimentin or myc-pCMV were not labeled with the anti-myc antibody.

Example 5

Blood Vessel Localization via Metadherin

This example demonstrates how to examine for the presence of metadherin in lung blood vessels and that a metadherin expressing phage will cause cell delivery to the lung blood vessels. Phage expressing metadherin were examined by i.v. injection of 2.5×10$^{10}$ pfu metadherin phage (in 200 μl M9LB) into the tail vein of a mouse. Blood vessels were visualized by co-injection of phage with 200 μg of *Lycopersicon esculentum* (tomato) lectin conjugated to fluorescein and either metadherin phage (T7-metadherin) or T7-415 non-recombinant phage (T7-Control). Control lungs were from non-injected mice (lectin⁻phage⁻), mice injected with lectin alone (lectin⁺phage⁻), and mice only injected with metadherin phage (lectin⁻phage⁺). Anti-phage antibody was detected with Alexa 594 goat anti-rabbit IgG antibody. Nuclei were stained with DAPI. The injected materials were allowed to circulate for 10 min. Lungs were removed and frozen in OCT embedding medium (Tissue-Tek). The phage bound to lungs almost 20-fold more than control phage (FIG. 3). No selective accumulation of this phage was seen in breast, skin, brain, or liver and its amount was less than 2-fold above control phage in pancreas and kidney. The phage co-localized with blood vessels in the lungs.

Example 6

Analysis of Metadherin and Metadherin Variant Levels in Tumor Cell Lysates

This example demonstrates how to monitor the amount of metadherin in tumor cell lysates. Tumor cell lysates were prepared in 2.5× Laemmli's sample buffer (Laemmli, 1970) at a ratio of $10^6$ cells per 150 µL, subjected to SDS/PAGE on 4-20% acrylamide gradient gels. Proteins were transferred to PVDF membrane and immunoblots were performed with anti-metadherin$_{(378-440)}$ (0.1 µg/ml) and goat anti-rabbit IgG-HRP (diluted 1:10,000; Bio-Rad, Hercules, Calif.) and developed using ECL+plus chemiluminescence reagent (Amersham Biosciences, Piscataway, N.J.), according to the manufacturer's instructions. The relative amount of metadherin detected by immunoblot was quantitated using an AlphaImager (Alpha Innotech, San Leandro, Calif.). β-actin was detected with an anti-actin monoclonal antibody (10 µg/ml, Chemicon, Temecula, Calif.). Transferrin receptor was detected with an anti-transferrin receptor polyclonal antibody (2 µg/ml, Santa Cruz Biotech, Santa Cruz, Calif.). Affinity-purified polyclonal antibody reactive to a novel 175 kDa protein Clone D2 was prepared as described for anti-metadherin$_{(378-440)}$. Control immunoblots were performed with anti-Clone D2 (0.1 µg/ml) and goat anti-rabbit IgG-HRP (described above).

Figure 5:
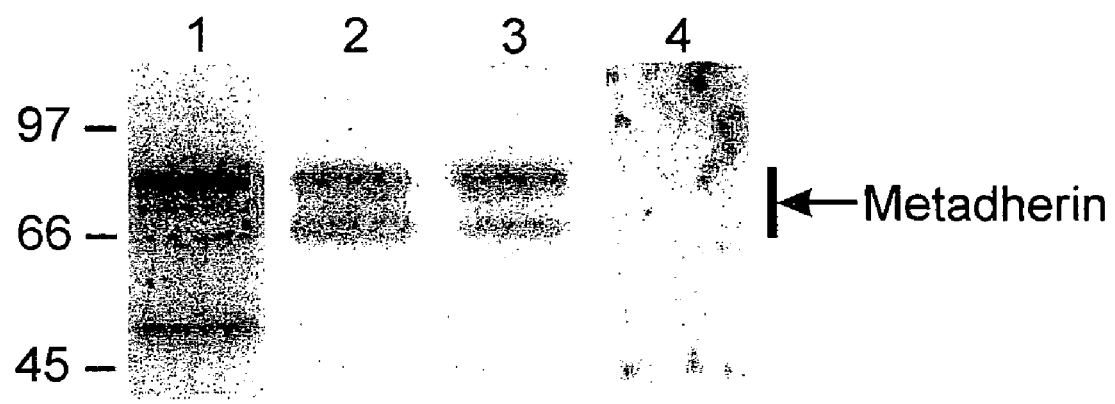
FIG. 5 is an image of a gel that demonstrates metadherin expression in 4T1 tumor cells.

In 4T1 tumor cell extracts, anti-metadherin$_{(378-440)}$ antibodies-detected proteins with apparent molecular weights of approximately 80 kDa, 75 kDa, and 55 kDa. KRIB and MDA-MB-435 cell extracts also contained the 80 kDa and 75 kDa proteins. FIG. 5 shows an immunoblot of endogenous metadherin. Lanes 1 and 4, are from 4T1 cell extract, lane 2, KRIB cell extract, and lane 3, MDA-MB-435 cell extract. Immunoblot detection of metadherin was performed with anti-metadherin$_{(378-440)}$ (lanes 1-3). Immunoblot detection of an unrelated protein, Clone D2, was performed with anti-Clone D2 polyclonal antibody (lane 4). The control affinity-purified polyclonal antibody reactive to a non-related protein (Clone D2) did not detect the anti-metadherin$_{(378-440)}$ immunoreactive bands. The 80 kDa and 55 kDa proteins detected by anti-metadherin$_{(378-440)}$ were also produced by an in vitro transcription and translation reaction using an epitope-tagged metadherin cDNA as template; this suggested that the 75 kDa and 55 kDa proteins may be degradation products of metadherin.

Example 7

Metadherin Localizes to the Cell Membrane and the Specificity of mB$_{(378-440)}$ This example provides a demonstration of how to use anti-metadherin$_{(378-440)}$ antibodies to look for metadherin in different locations of the cell, and describes the distribution of the molecule throughout the cell. This example also demonstrates how to determine which labeling effects are due to the specific binding of this antibody.

Cell-surface labeling: Anti-metadherin$_{(378-440)}$, diluted to 20 µg/ml in ice-cold IMEM (Invitrogen) with 10% fetal bovine serum (FBS), was added to cells cultured on chamber slides and incubated for 1 hour on ice. The cells were washed with IMEM and fixed with cold 4% paraformaldehyde in PBS for 15 minutes. Anti-metadherin antibodies were detected with Alexa 594 goat anti-rabbit IgG (diluted 1:500 in PBS with 1% FBS and 3% goat serum). Slides were mounted with Vectashield fluorescence mounting medium (Vector, Burlingame, Calif.). In non-permeabilized cells, the staining was concentrated at the edges of the cells. Controls showed that pre-incubation of anti-metadherin$_{(378-440)}$ with the metadherin$_{(378-440)}$ lung-homing peptide inhibited the staining, whereas a control peptide did not.

Permeabilized cell labeling: Cells were first fixed with 4% paraformaldehyde (described above) and then treated with 0.1% Triton X-100 in PBSB for 15 minutes. The cells were washed with PBSB and incubated with anti-metadherin$_{(378-440)}$ (diluted to 20 µg/ml in IMEM with 10% FBS) for 1 hour at room temp. Anti-metadherin$_{(378-440)}$ was detected with Alexa 594 goat anti-rabbit IgG, as described above. In fixed and permeabilized 4T1 cells, metadherin immunoreactivity localized to the cytoplasm and plasma membrane. In sections (0.15 µm thick) of non-permeabilized 4T1 cells stained with anti-metadherin$_{(378-440)}$ the staining was concentrated to the edges of the cell. As a control, non-permeabilized 4T1 cells that were pre-incubated with excess metadherin$_{(378-440)}$ peptide demonstrated reduced staining with anti-metadherin$_{(378-440)}$, while those cells incubated in excess control peptide did not. Alexa 594 goat anti-rabbit IgG antibody were used.

Example 8

Detection of Metadherin in Human Tumors Samples as a Means for Diagnosing the Spread of Cancer This example demonstrates how to determine the amount of metadherin present in a human tissue sample that is cancerous. Paraffin-embedded human tumor sections (Spring Biosciences, Fremont, Calif.) were de-paraffinized and then treated with Target Retrieval Solution (according to the manufacturer's instructions; Dako, Carpinteria, Calif.). The sections were stained as described above, except PBSB was substituted for 0.5% Blocking Reagent (NEN Life Sciences, Boston, Mass.) in 0.1 M Tris/150 mM NaCl. To determine specificity, anti-metadherin$_{(378-440)}$ (20 µg/ml) was pre-incubated overnight with 200 µg/ml recombinant metadherin lung-homing protein (SEQ ID NO: 3) or unrelated recombinant control protein (72 amino acid, lung-homing Clone D2) in blocking buffer before immunostaining the sections. Both sections of human breast tumor and normal human breast tissue were stained with either anti-metadherin$_{(378-440)}$ alone or anti-metadherin$_{(378-440)}$ pre-incubated with excess metadherin$_{(378-440)}$ peptide or excess control peptide.

Several human breast cancer sections stained with anti-metadherin$_{(378-440)}$ showed high expression of metadherin throughout the tumor. In contrast, no cytoplasmic or cell surface-associated metadherin was detected in normal human breast tissue; however, nuclear staining was present. The cell surface staining of breast cancer tissue was inhibited with the metadherin$_{(378-440)}$ peptide, but not with a control peptide. Neither peptide inhibited nuclear staining.

Example 9

Detection of Metadherin in Xenografts as Means for Diagnosing Cancer Cells

This example demonstrates that the detection method works for samples that are not of human origin. High amounts of metadherin proteins were detected in sections of murine MDA-MB-435 (breast adenocarcinoma) and KRIB (osteosarcoma tumor) tumor xenografts, which are two tumor models known to generate lung metastases (Berlin et al., 1993; Price et al., 1990). Xenografts were grown in nude Balb/c mice and were analyzed by immunostaining. Sections were stained with either anti-metadherin$_{(378-440)}$ alone or anti-metadherin$_{(378-440)}$ pre-incubated with excess metadherin$_{(378-440)}$ peptide or excess control peptide. Anti-metadherin$_{(378-440)}$ was detected with Alexa 594 goat anti-rabbit IgG antibody and nuclei were stained with DAPI. Metadherin appeared to be localized to the tumor cell surface in the both models and particularly strong expression of metadherin was found at the periphery of the KRIB tumors. The anti-metadherin immunostaining was specific, since pre-incubation of antibody with the metadherin$_{(378-440)}$ lung-homing peptide, but not the control peptide, inhibited the staining. Subcutaneous tissue or skin adjacent to the tumors showed no anti-metadherin staining.

Specific metadherin staining was present in frozen tissue sections of normal mouse mammary tissue at the apical surface of epithelial cells lining ducts of the mammary glands and a small amount of metadherin was dispersed through the mammary fat pad. Sections of mouse breast tissue were stained with either anti-metadherin$_{(378-440)}$ alone or anti-metadherin$_{(378-440)}$ pre-incubated with excess metadherin$_{(378-440)}$ peptide. No metadherin was detected in the spleen, kidney, lung, and skin, but minute amounts were seen in the liver. Purkinje neurons in the early post natal and adult cerebellum were strongly positive for metadherin staining. These immunostaining results show that metadherin is selectively over-expressed in tumors.

Example 10

Delivery of a Desired Substance to a Particular Location

This example demonstrates the ability of metadherin to effectively deliver an associated substance to the lung tissue. To test the effect of metadherin on tissue distribution of i.v.-injected tumor cells, HEK293T cells were studied by transiently transfecting them with metadherin cDNA (SEQ ID NO: 2). HEK293T cells were co-transfected with DsRed2 (Clontech, Palo Alto, Calif.) and either metadherin-pCMV or an empty myc-pCMV vector. Two days post-transfection, the cells were detached with PBSE and filtered through a 40 µm nylon filter. DsRed-expressing cells were isolated using a FACS Vantage flow cytometer (BD Biosciences, San Jose, Calif.). $2.5 \times 10^5$ DsRed-positive cells, the cells being the desired substance in this experiment, were injected into the tail-vein of nude BALB/c mice. Five mice were injected with each cell type. After 2 hours, the mice were sacrificed, organs were removed and fixed with 4% paraformaldehyde in PBS, and 10 µm-thick frozen tissue sections were prepared. For each lung section, 3 different fields were counted. Clumps of DsRed positive cells with 3 or more cells were excluded from the count. Five sections per lung were counted.

Figure 6:
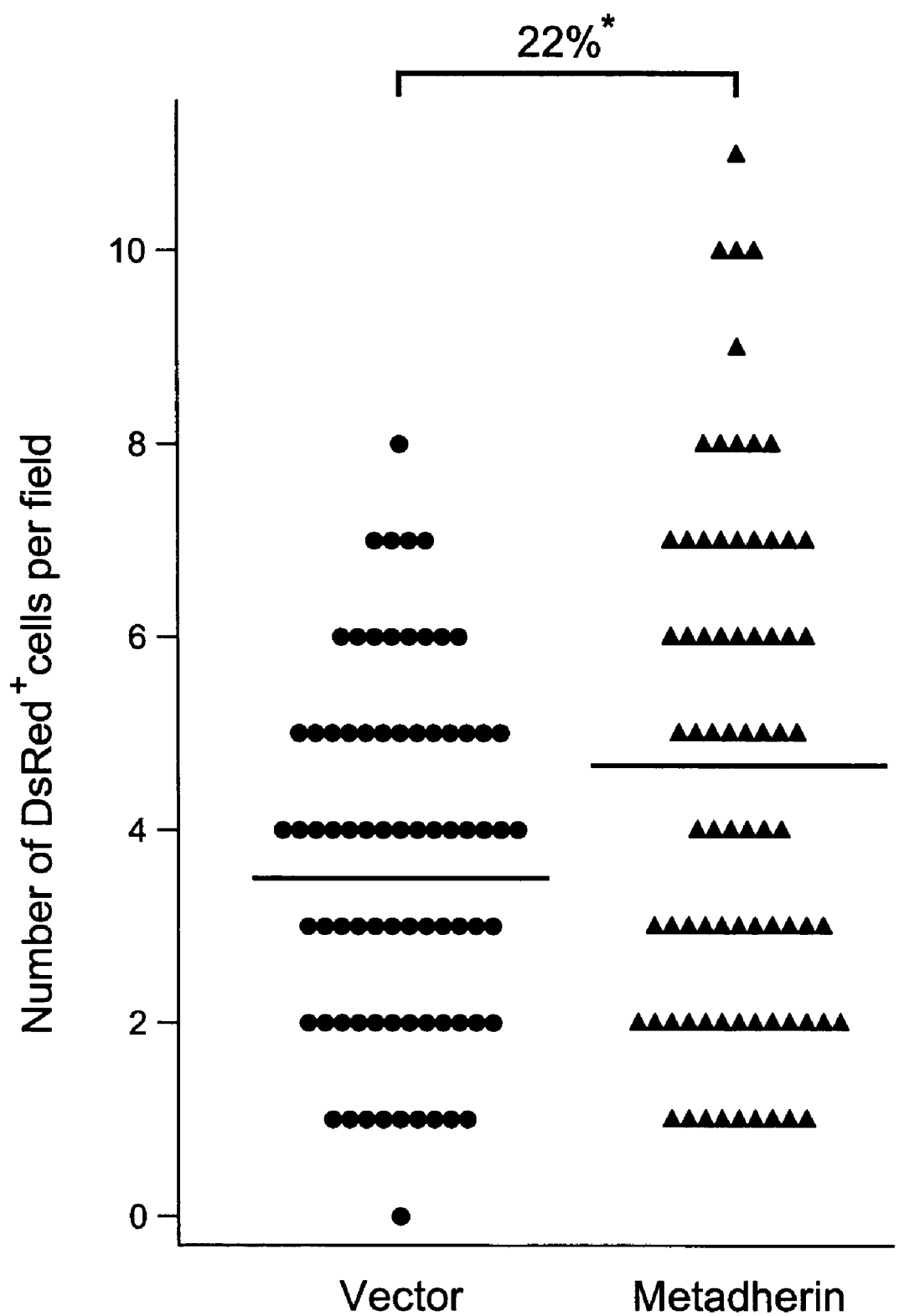
FIG. 6 is a graph that shows the number of DsRed2-positive cells per viewing field in the lung sections. (n=75; One-tailed Student's t-test; *P<0.001).

Fluorescent cells were detected in the blood vessels of lungs examined two hours after the injection; cell counting showed 22% more metadherin-transfected cells than that of vector-transfected cells. No significant amounts of DsRed2 HEK293T cells were observed in the brain, skin, liver, kidney, heart, spleen, or pancreas. FIG. 6 shows the number of DsRed2-positive cells per viewing field in the lung sections (n=75; One-tailed Student's t-test; *P<0.001). This result supports the phage homing data indicating that metadherin preferentially binds to lung vasculature.

Example 11

Figure 7A:
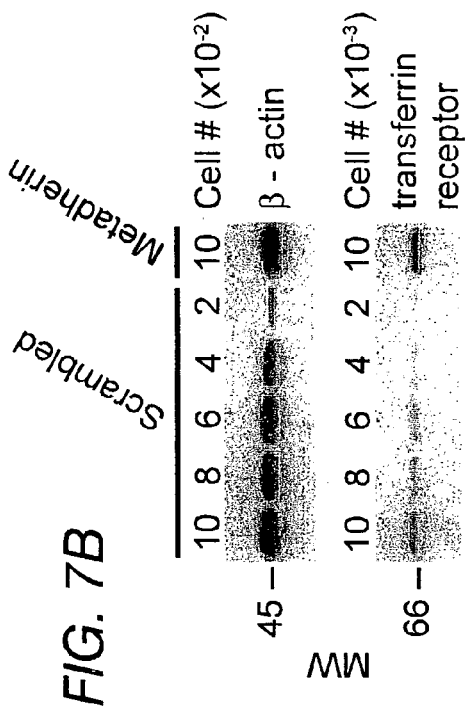
FIG. 7A is an image of a gel that shows an anti-myc immunoblot of HEK293T cell extracts expressing myc-tagged metadherin and siRNA reactive to GAPDH, scrambled mRNA, or metadherin.
Figure 7B:
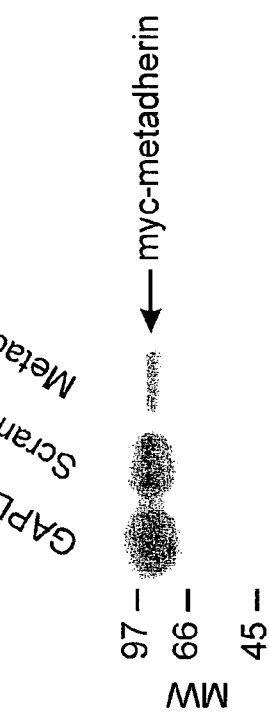
FIG. 7B is an image of a gel that shows immunoblot quantitation of β-actin and transferrin receptor protein levels in 4T1 cells expressing siRNA reactive to metadherin or scrambled mRNA.
Figure 7C:
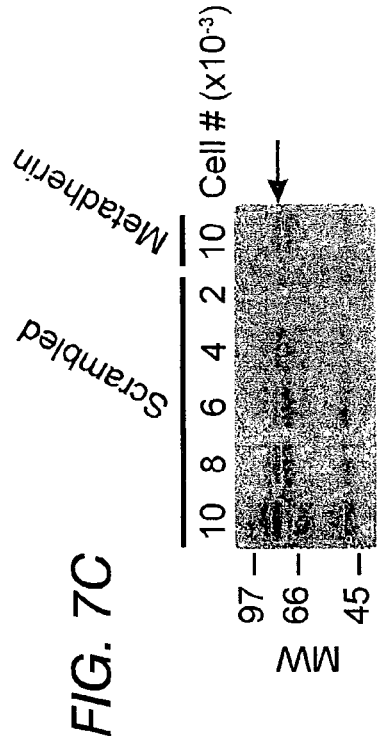
FIG. 7C is an image of a gel that shows immunoblot quantitation of metadherin protein levels in 4T1 cells expressing siRNA reactive to metadherin or scrambled mRNA.

Inhibition of Metadherin via SiRNA and its Ability to Reduce the Formation of Metastases siRNA to Metadherin can Inhibit Metadherin The ability of siRNA to alter metadherin production was examined. As shown in FIG. 7A, siRNA reactive to metadherin, but not to GAPDH or a negative control, mRNA (e.g., "scrambled"), was able to reduce expression of transfected myc-metadherin in HEK293T cells. Metadherin levels returned to normal after two weeks. However, a workable model was created using the co-expression of EGFP and the metadherin-reactive siRNA or scrambled-siRNA in 4T1 cells and the cells were selected by FACS. The transfection with metadherin-siRNA did not affect the expression of beta-actin or the type-II transmembrane protein, transferring receptor (see FIG. 7B). However, metadherin protein expression in metadherin-siRNA cells was reduced by about 40%, relative to the scrambled-siRNA cells (FIG. 7C). The arrow in FIG. 7C denotes the 80 kDa metadherin protein band quantified by densitometry.

Figure 7D:
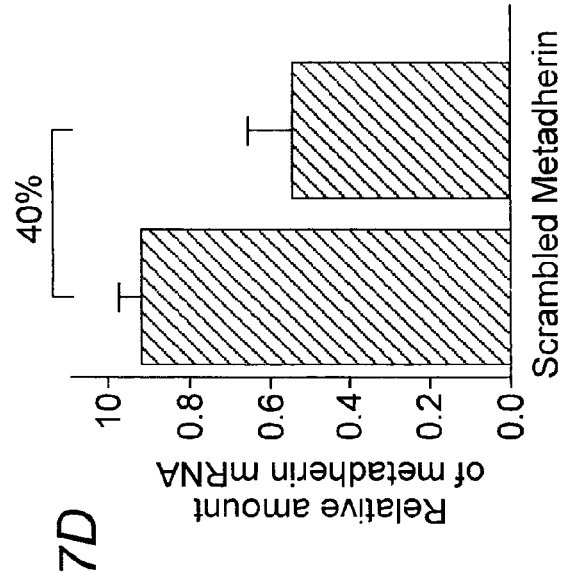
FIG. 7D is a bar graph that shows real time RT-PCR quantitation of metadherin mRNA in 4T1 cells expressing siRNA reactive to metadherin or scrambled mRNA.

Measured by real-time PCR, metadherin-siRNA cells expressed about 40% less metadherin mRNA than the scrambled-siRNA cells when metadherin mRNA levels were normalized to beta-actin mRNA levels (FIG. 7D). The relative amount of metadherin mRNA was normalized to the abundance of P-actin mRNA, also detected by real time RT-PCR. Error bars represent mean±s.d.

siRNA to Metadherin can Inhibit the Formation of Metastases in Mouse Model

This example demonstrates the effectiveness of siRNA directed against metadherin to alter the metastatic potential of breast cancer cells by reducing the native level of metadherin in cells. For the siRNA-mediated inhibition of metadherin expression, nucleotides 1597-1615 of the mouse metadherin cDNA (5'-GTGCCACCGATGTTACAAG-3') (SEQ ID NO: 11) were used as the target sequence. Oligonucleotides containing this target sequence were synthesized and subcloned into the pSilencer 3.0-H1 plasmid (Ambion, Austin, Tex.), according to the manufacturer's instructions. Green fluorescent protein (EGFP) was co-expressed with the metadherin-reactive siRNA or a control scrambled-siRNA in 4T1 cells and selected for siRNA-transfected cells by FACS. 4T1 cells were transfected with the metadherin or a negative control siRNA pSilencer vector together with an EGFP-expression vector (Clontech, Palo Alto, Calif.), using a 4:1 ratio of pSilencer to EGFP vectors. Two days post-transfection, 4T1 cells that were labeled with EGFP and excluded propidium iodide were isolated by FACS. 10,000 or 50,000 of these selected 4T1 cells in 100 µl of PBS were injected into the tail-vein of anesthetized nude BALB/c mice. The mouse lungs were harvested 22 days post-injection and stained with Bouin's solution. The tumor foci on the lung surface were counted under a dissecting microscope. Data were recorded as the number of tumor foci formed per 10,000 cells injected.

Figure 7E:
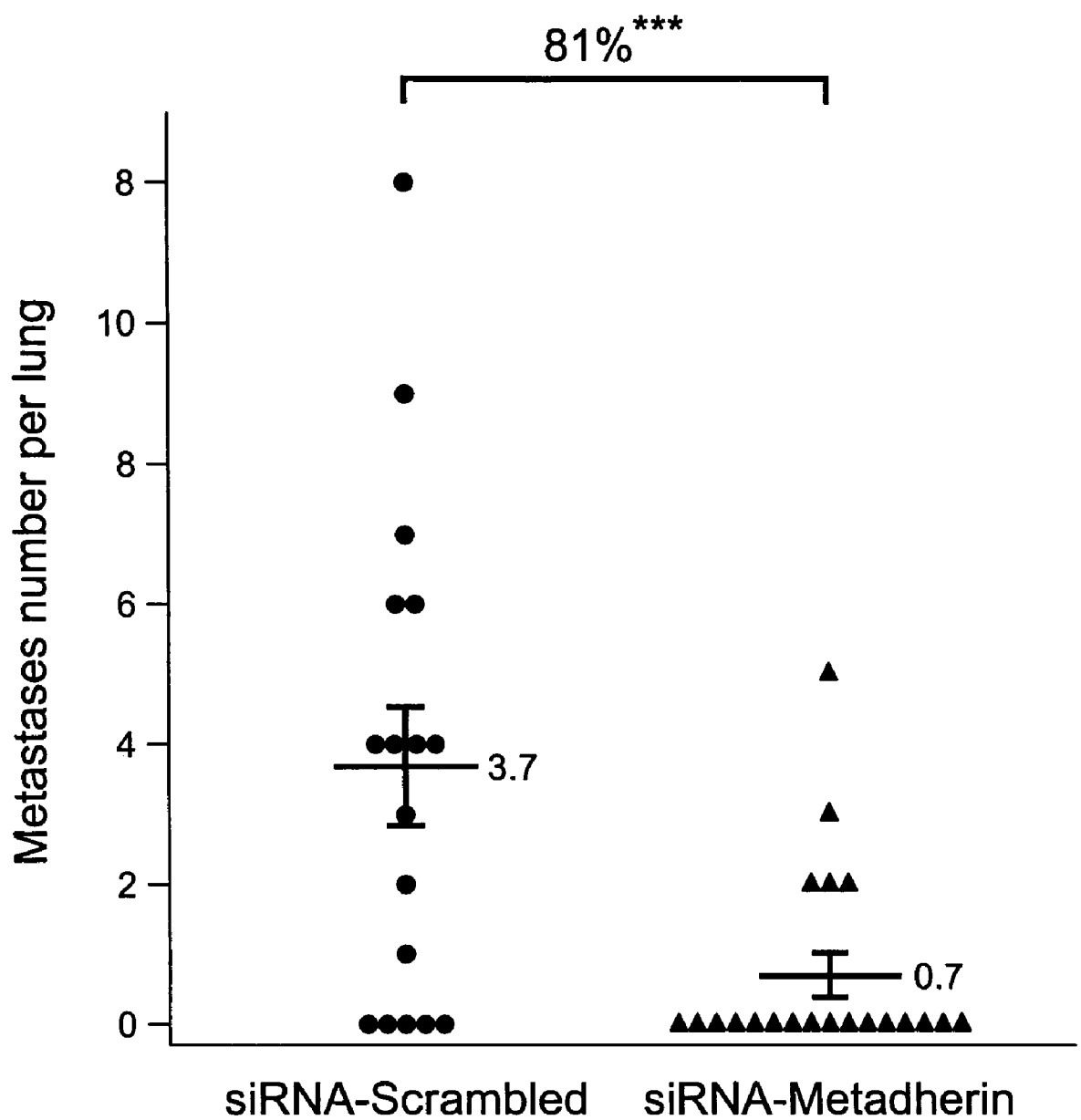
FIG. 7E is a graph displaying that siRNA reactive to metadherin transcripts inhibits 4T1 cell experimental lung metastasis.

When injected into mice, the 4T1 cells expressing metadherin-reactive siRNA formed about 80% fewer experimental lung metastases than cells expressing scrambled-siRNA (P<0.001). The results are displayed in FIG. 7E. Values are expressed as number of tumor foci per 10,000 cells injected. Bars represent mean±s.e.m (One-tailed Student's t-test; *P<0.02, P<0.01, *P<0.001). Percentages indicate relative suppression compared to control group. No difference in the viability of metadherin-siRNA and scrambled-siRNA cells was detected by the use of propidium iodide staining. In addition, a count of the number of cells before and two days after transfecting the siRNA expression plasmids did not show any significant effect of the metadherin-siRNA on the growth rate of the cells.

Example 12

Production of an Additional Homolog to Metadherin:

The deduced amino acid sequence of the lung-homing domain of the lung-homing phage is shown in SEQ ID NO: 3. Using BLAST (Altschul, S. F., et al., *Nucleic Acids Res* 25: 3389-3402 (1997)), It was determined that one cDNA clone (GenBank™ accession number AY082966—SEQ ID NO: 16) encoded the putative full-length human protein (SEQ ID NO: 13) corresponding to the phage clone. The cDNA encoding metadherin has a coding region that is 93% identical to the coding region (SEQ ID NO: 2) of the murine metadherin. The GenBank™ entry refers to the protein as "LYRIC" and describes it as a putative CEACAM1-associated protein in colon carcinoma. These results that show the importance of this lung-homing protein in breast cancer metastasis. The protein was named metadherin (metastasis adhesion protein). A reported mouse cDNA homolog of metadherin was used (GenBank™ accession number AK029915) to design oligonucleotides and amplified by reverse transcription-polymerase chain reaction the full-length mouse metadherin cDNA (SEQ ID NO: 2). As shown in SEQ ID NO: 2, the mouse metadherin cDNA is 2530 nucleotides in length with a 1737 base pair coding region that starts at nucleotide 319 and ends at nucleotide 2058. The human metadherin cDNA is 2031 nucleotides in length with a 1748 base pair coding region that starts at nucleotide 79 and ends at nucleotide 1827. As will be appreciated by one of skill in the art, this procedure can readily be repeated to identify additional homologs in other organisms.

Example 13

Process for Determining the Functional Regions of Metadherin

This example demonstrates a method for identifying and then verifying the functional features of metadherin or its variants. Analysis of the hydrophobic regions of metadherin (Kyte, J. and Doolittle, R. F., *J Mol Biol* 157, 105-132 (1982)) revealed that amino acid residues 52-74 encode a putative transmembrane domain (e.g., FIG. 1B and FIG. 1C). A search did not reveal any domains in metadherin that were similar to other known proteins. Using a hidden Markov model to detect membrane helices and predict transmembrane topology in proteins (Glasgow, J. (1998), Proceedings, Sixth International Conference on Intelligent Systems for Molecular Biology: Jun. 28-Jul. 1, 1998, Montreal, Quebec (Menlo Park, Calif., AAAI Press); Krogh, A., et al., *J Mol Biol* 305: 567-580 (2001)), it was discovered that metadherin was predicted to be a type II transmembrane protein with an extracellular lung-homing domain. To confirm this prediction, a c-myc epitope was subcloned into the lung-homing domain of the metadherin cDNA, as shown in FIG. 1C. A myc epitope was added to metadherin protein by first inserting an EcoRI restriction enzyme site in the metadherin cDNA after nucleotide 1222 with a QuickChange site-directed mutagenesis kit (Stratagene, La Jolla, Calif.). Then, oligonucleotides encoding a myc epitope (EQKLISEEDL) [SEQ ID NO: 12] and flanking EcoRI adapters were synthesized, phosphorylated, and ligated into the EcoRI-digested metadherin cDNA. The myc-metadherin cDNA was subcloned into the pCMV vector (Clontech, Palo Alto, Calif.). Human myc-vimentin cDNA was generated by reverse transcription-polymerase chain reaction, using vimentin-specific primers and human mRNA as template, and then subcloned into the pCMV-Myc vector (Clontech, Palo Alto, Calif.).

This myc-tagged cDNA was expressed in HEK293T cells and these cells were then stained with anti-myc antibodies. Using flow cytometry, it was observed that intact myc metadherin-expressing cells were labeled with anti-myc antibodies, which indicated that the lung-homing domain of metadherin was extracellular. No cell-surface labeling was detected in vector-transfected cells or non-permeabilized cells expressing the intracellular protein, myc-vimentin. Anti-myc antibodies stained the myc vimentin-expressing cells when permeabilized, confirming the expression of myc-vimentin, and permeabilized cells expressing vector alone were not stained with anti-myc antibodies.

This example can be modified by simply using the antibody to metadherin$_{(378\text{-}440)}$ in order to determine if variants of metadherin are still functional or still have certain desired properties.

Example 14

Inhibition of Metastasis by Metadherin mAbs

Figure 7F:
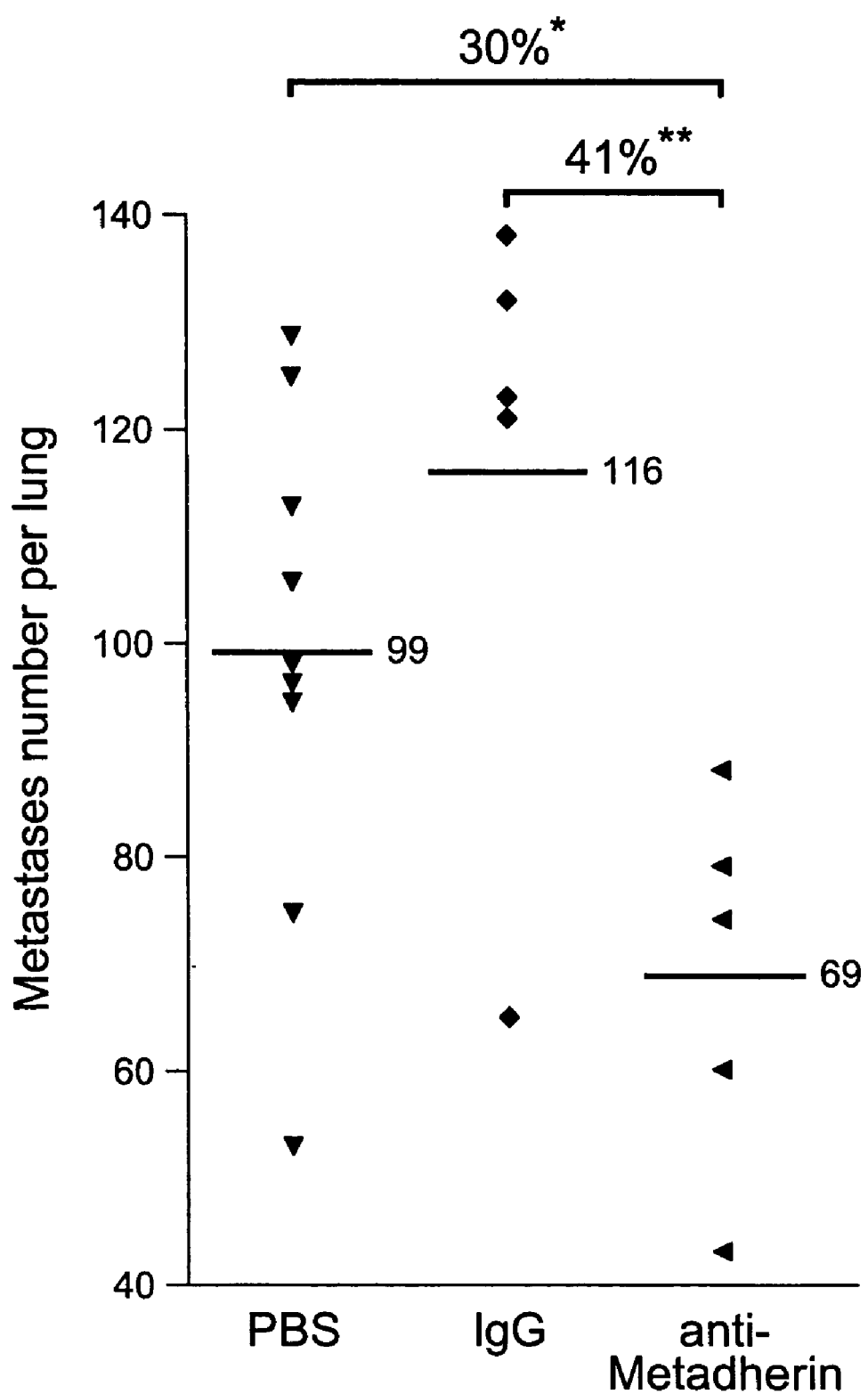
FIG. 7F is a graph that shows the number of lung metastases from mice injected with 4T1 cells that were treated with anti-metadherin$_{(378-440)}$, rabbit IgG, or PBS.

This example demonstrates how metastasis were inhibited by the addition of a binding agent, in this case, antibodies directed to the lung-binding domain of metadherin. The mouse model system was used to inhibit metadherin activity in the 4T1 cells with antibodies reactive to the lung-homing domain of metadherin. The 4T1 cells were detached from plates with PBSE, washed once with PBS, re-suspended to $5 \times 10^5$ cells/ml in PBS, and placed on ice. Anti-metadherin$_{(378\text{-}440)}$ or rabbit IgG (200 µg) was added to $5 \times 10^4$ cells and the cells were then injected via the lateral tail vein into female Balb/c nu/nu mice. Animals were sacrificed 7 days after tumor cell injection. Lungs were recovered, stained with Bouin's solution, and the tumor foci on the surface of the left lobe were counted under a dissecting microscope. When co-injected with the 4T1 cells, anti-metadherin$_{(378\text{-}440)}$ inhibited lung metastasis by about 40%, compared to 4T1 cells treated with rabbit IgG (FIG. 7F). In a separate experiment, no difference was observed between the growth of mammary fat pad tumors formed from 4T1 cells pretreated with the anti-metadherin$_{(378\text{-}440)}$ or rabbit IgG.

Example 15

Screening of Therapeutics that Block Metastasis via Metadherin

This example demonstrates how one can screen for small molecules, peptides or proteins that bind to and block metastasis via blocking metadherin. Cells expressing metadherin or a fragment thereof, such as in the phage clones in Example 1, are mixed with the possible blocking agent and then injected into mice, according to Example 1. If the injected cells localize to the lung tissue, then the blocking agent is not effective as a complete blocking agent, over the time period of the experiment. A reduction in the localization of the cells to the lung tissue or comparison to a control will indicate a possible blocking agent.

Example 16

Determination of Metadherin's Role in Other Cancers in Silico

This example demonstrates how one can determine if the metadherin of the current invention will be useful in stopping the metastasis of other cancers. SAGEmap (Lal, A., et al., *Cancer Res* 59: 5403-5407 (1999); Lash, A. E., et al., *Genome Res* 10: 1051-1060 (2000)), a component of The Cancer Genome Anatomy Project at the National Center for Biotechnology Information, was used to determine that metadherin was significantly over-expressed not only in breast cancers, but also in cancers of the brain and prostate ($P<0.05$). This suggests a similar role for metadherin in the metastasis of brain and prostate cancers. One may then administer the anti-metadherin antibody of the current invention and determine if cancer metastasis is halted or not.

Example 17

Determination of Variants of Metadherin, in Silico

This example demonstrates a technique to determine other variants of metadherin. A BLAST algorithm (Altschul, S. F., et al., *Nucleic Acids Res* 25: 3389-3402 (1997)), was used to determine additional mouse and human metadherin-like molecules in the GENBANK™ databases. FIG. 2 demonstrates a functional comparison of the several metadherin homologs or variants from human (SEQ ID NO: 13), mouse (SEQ ID NO: 1), rat (SEQ ID NO: 14), and zebra fish (SEQ ID NO: 15) are now known.

Example 18

Determination of Functional Variants for Preventing Metastasis

This example demonstrates how possible variants of metadherin can be examined to determine if they are still functional for preventing cancer metastasis. The possible variant is expressed in a host cell that can be monitored, as in Example 1. The variant is then administered, as in Example 1, into a host to determine if the variant is able to localize the host cell to the lung tissue. If the variant is still able to localize to the lung tissue, and thus bind to the metadherin receptors, then it is considered a functional variant, for the purposes of preventing the spread of cancer.

Example 19

The use of Antibodies Directed to Metadherin to Reduce Breast Cancer Metastasis A patient with cancer and a risk of breast cancer metastasis is selected. The risk of breast cancer metastasis is examined by determining the presence of metadherin in the patient's system, with increased levels of metadherin, relative to cancer free patients, indicating that the patient has an increased risk of breast cancer metastasis. An effective amount of an antibody directed to the binding region of metadherin is then administered to the patient, this may be administered in combination with other cancer chemotherapy or other treatments. An effective amount is determined on a patient by patient basis and can be directly monitored by repeated assays for antibody-free metadherin that still exists in the patient's system. Alternatively, an effective amount is determined by monitoring the overall health of the patient and the reduction of any spread of the cancer. The treatment is continued until the spread of the cancer is reduced.

Example 20

The use of siRNA Directed to Metadherin to Reduce Breast Cancer Metastasis

A patient with cancer and a risk of breast cancer metastasis is selected. The risk of breast cancer metastasis is determined by looking for the presence of metadherin in the patient's system, with increased levels of metadherin, relative to cancer free patients, indicating that the patient has an increased risk of breast cancer metastasis. An effective amount of a siRNA directed to metadherin is then administered to the patient, this may be administered in combination with other cancer chemotherapy or other treatments. An effective amount is determined on a patient by patient basis and is directly monitored by repeated assays for the presence of metadherin that still exists in the patient's system. The treatment is continued until the spread of the cancer is reduced.

Example 21

The use of siRNA to Treat Breast Cancer

A patient with breast cancer is selected. The risk of breast cancer metastasis is determine by looking for the presence of metadherin in the patient's system, with increased levels of metadherin, relative to cancer free patients, indicating that the patient has an increased risk of breast cancer metastasis. An effective amount of a siRNA directed to metadherin is then administered to the patient, this may be administered in combination with other cancer chemotherapy or other treatments. An effective amount is determined on a patient by patient basis and is directly monitored by repeated assays for the presence of metadherin that still exists in the patient's system. The treatment is continued until the breast cancer is reduced.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference in their entireties.

We claim:

1. A method of inhibiting tumor metastasis in a patient, comprising:
    selecting a patient at risk for metastasis of a tumor; and
    administering to said patient an effective amount of an antibody, or a binding fragment of the antibody, that binds to a metadherin polypeptide comprising the amino acid sequence in SEQ ID NO: 17, and wherein the antibody, or binding fragment of the antibody, reduces the metadherin polypeptide, or a binding fragment of the metadherin polypeptide, from binding to its receptor, thereby inhibiting tumor metastasis in the patient.

2. The method of claim 1, wherein said metadherin polypeptide comprises the amino acid sequence shown in SEQ ID NO: 13.

3. The method of claim 1, wherein said metadherin polypeptide consists of the amino acid sequence shown in SEQ ID NO: 17.

4. The method of claim 1 wherein the antibody is a monoclonal antibody that preferentially binds the metadherin polypeptide.

5. The method of claim 4, wherein said antibody is a monoclonal antibody that preferentially binds to a lung-binding domain of the metadherin polypeptide.

6. The method of claim 1, wherein said receptor is located on lung vasculature.

7. The method of claim 1, wherein said tumor is a breast cancer tumor.

8. A method of inhibiting tumor metastasis in a patient, comprising:
    selecting a patient at risk for metastasis of a tumor; and
    administering to said patient an effective amount of an antibody, or binding fragment of the antibody, that binds to a metadherin polypeptide, wherein the metadherin polypeptide comprises the amino acid sequence in SEQ ID NO: 13, and wherein the antibody, or binding fragment of the antibody, reduces the metadherin polypeptide, or a binding fragment of the metadherin polypeptide, from binding to its receptor, thereby inhibiting tumor metastasis in the patient.

9. The method of claim 8, wherein said metadherin polypeptide consists of the amino acid sequence shown in SEQ ID NO: 13.

10. The method of claim 8, wherein said antibody, or binding fragment of the antibody, binds to a polypeptide consisting of the amino acid sequence in SEQ ID NO: 17.

11. The method of claim 8, wherein the antibody is a monoclonal antibody that preferentially binds the metadherin polypeptide.

12. The method of claim 8, wherein said antibody is a monoclonal antibody that preferentially binds to a lung-binding domain of the metadherin polypeptide.

13. The method of claim 8, wherein said receptor is located on lung vasculature.

14. The method of claim 8, wherein said tumor is a breast cancer tumor.

15. A method of inhibiting tumor metastasis in a patient, comprising:
    selecting a patient at risk for metastasis of a tumor; and
    administering to said patient an effective amount of an antibody, or binding fragment of the antibody, that binds to a protein consisting of the amino acid sequence in SEQ ID NO: 17, and wherein the antibody, or binding fragment of the antibody, reduces a metadherin polypeptide from binding to its receptor, wherein the metadherin polypeptide comprises the amino acid sequence in SEQ ID NO: 13.

* * * * *

UNITED STATES PATENT AND TRADEMARK OFFICE
CERTIFICATE OF CORRECTION

PATENT NO. : 7,560,242 B2  Page 1 of 1
APPLICATION NO. : 10/986466
DATED : July 14, 2009
INVENTOR(S) : Ruoslahti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 838 days.

Signed and Sealed this

Seventh Day of September, 2010

David J. Kappos
*Director of the United States Patent and Trademark Office*

SEQUENCE LISTING

<160> NUMBER OF SEQ ID NOS: 20

<210> SEQ ID NO 1
<211> LENGTH: 579

-continued

```
<212> TYPE: PRT
<213> ORGANISM: Mus musculus

<400> SEQUENCE: 1
```

| Met | Ala | Ala | Arg | Ser | Trp | Gln | Asp | Glu | Leu | Ala | Gln | Gln | Ala | Glu | Glu |
|---|---|---|---|---|---|---|---|---|---|---|---|---|---|---|---|
| 1 | | | | 5 | | | | | 10 | | | | | 15 | |

| Gly | Ser | Ala | Arg | Leu | Arg | Glu | Leu | Leu | Ser | Val | Gly | Leu | Gly | Phe | Leu |
| | | | 20 | | | | | 25 | | | | | 30 | | |

| Arg | Thr | Glu | Leu | Gly | Leu | Asp | Leu | Gly | Leu | Glu | Pro | Lys | Arg | Tyr | Pro |
| | | 35 | | | | | 40 | | | | | 45 | | | |

| Gly | Trp | Val | Ile | Leu | Val | Gly | Thr | Gly | Ala | Leu | Gly | Leu | Leu | Leu |
| | 50 | | | | | | 55 | | | | | 60 | | | |

| Phe | Leu | Leu | Gly | Tyr | Gly | Trp | Ala | Ala | Ala | Cys | Ala | Gly | Ala | Arg | Lys |
| 65 | | | | 70 | | | | | 75 | | | | | | 80 |

| Lys | Arg | Arg | Ser | Pro | Pro | Arg | Lys | Arg | Glu | Glu | Ala | Ala | Pro | Pro | Thr |
| | | | | 85 | | | | | 90 | | | | | 95 | |

| Pro | Ala | Pro | Asp | Asp | Leu | Ala | Gln | Leu | Lys | Asn | Leu | Arg | Ser | Glu | Glu |
| | | | | 100 | | | | | 105 | | | | | 110 | |

| Gln | Lys | Lys | Lys | Asn | Arg | Lys | Lys | Leu | Pro | Glu | Lys | Pro | Lys | Pro | Asn |
| | | | 115 | | | | | 120 | | | | | 125 | | |

| Gly | Arg | Thr | Val | Glu | Val | Pro | Glu | Asp | Glu | Val | Val | Arg | Asn | Pro | Arg |
| | 130 | | | | | 135 | | | | | 140 | | | | |

| Ser | Ile | Thr | Ala | Lys | Gln | Ala | Pro | Glu | Thr | Asp | Lys | Lys | Asn | Glu | Lys |
| 145 | | | | | 150 | | | | | 155 | | | | | 160 |

| Ser | Lys | Lys | Asn | Lys | Lys | Ser | Lys | Ser | Asp | Ala | Lys | Ala | Val | Gln |
| | | | | 165 | | | | | 170 | | | | | 175 | |

| Asn | Ser | Ser | Arg | His | Asp | Gly | Lys | Glu | Val | Asp | Glu | Gly | Ala | Trp | Glu |
| | | | | 180 | | | | | 185 | | | | | 190 | |

| Thr | Lys | Ile | Ser | His | Arg | Glu | Lys | Arg | Gln | Gln | Arg | Lys | Arg | Asp | Lys |
| | | | 195 | | | | | 200 | | | | | 205 | | |

| Val | Leu | Thr | Asp | Ser | Gly | Ser | Leu | Asp | Ser | Thr | Ile | Pro | Gly | Ile | Glu |
| | | 210 | | | | | 215 | | | | | 220 | | | |

| Asn | Ile | Ile | Thr | Val | Thr | Thr | Glu | Gln | Leu | Thr | Thr | Ala | Ser | Phe | Pro |
| 225 | | | | | 230 | | | | | 235 | | | | | 240 |

| Val | Gly | Ser | Lys | Lys | Asn | Lys | Gly | Asp | Ser | His | Leu | Asn | Val | Gln | Val |
| | | | | 245 | | | | | 250 | | | | | 255 | |

| Ser | Asn | Phe | Lys | Ser | Gly | Lys | Gly | Asp | Ser | Thr | Leu | Gln | Val | Ser | Ser |
| | | | | 260 | | | | | 265 | | | | | 270 | |

| Arg | Leu | Asn | Glu | Asn | Leu | Thr | Val | Asn | Gly | Gly | Trp | Ser | Glu | Lys |
| | | | 275 | | | | | 280 | | | | | 285 | | |

| Ser | Val | Lys | Leu | Ser | Ser | Gln | Leu | Ser | Glu | Lys | Trp | Asn | Ser | Val |
| | 290 | | | | | 295 | | | | | 300 | | | | |

| Pro | Pro | Ala | Ser | Ala | Gly | Lys | Arg | Lys | Thr | Glu | Pro | Ser | Ala | Trp | Thr |
| 305 | | | | | 310 | | | | | 315 | | | | | 320 |

| Gln | Asp | Thr | Gly | Asp | Thr | Asn | Ala | Asn | Gly | Lys | Asp | Trp | Gly | Arg | Asn |
| | | | | 325 | | | | | 330 | | | | | 335 | |

| Trp | Ser | Asp | Arg | Ser | Ile | Phe | Ser | Gly | Ile | Gly | Ser | Thr | Ala | Glu | Pro |
| | | | | 340 | | | | | 345 | | | | | 350 | |

| Val | Ser | Gln | Ser | Thr | Thr | Ser | Asp | Tyr | Gln | Trp | Asp | Val | Ser | Arg | Asn |
| | | | | 355 | | | | | 360 | | | | | 365 | |

| Gln | Pro | Tyr | Ile | Asp | Asp | Glu | Trp | Ser | Gly | Leu | Asn | Gly | Leu | Ser | Ser |
| | | 370 | | | | | 375 | | | | | 380 | | | |

| Ala | Asp | Pro | Ser | Ser | Asp | Trp | Asn | Ala | Pro | Ala | Glu | Glu | Trp | Gly | Asn |
| 385 | | | | | 390 | | | | | 395 | | | | | 400 |

-continued

```
Trp Val Asp Glu Asp Arg Ala Ser Leu Leu Lys Ser Gln Glu Pro Ile
            405                 410                 415
Ser Asn Asp Gln Lys Val Ser Asp Asp Lys Glu Lys Gly Glu Gly
        420                 425                 430
Ala Leu Pro Thr Gly Lys Ser Lys Lys Lys Lys Lys Lys Lys
        435                 440                 445
Gln Gly Glu Asp Asn Ser His Thr Gln Asp Thr Glu Asp Leu Glu Lys
        450                 455                 460
Asp Thr Arg Glu Glu Leu Pro Val Asn Thr Ser Lys Ala Arg Pro Lys
465                 470                 475                 480
Gln Glu Lys Ala Cys Ser Leu Lys Thr Met Ser Thr Ser Asp Pro Ala
                485                 490                 495
Glu Val Leu Ile Lys Asn Ser Gln Pro Val Lys Thr Leu Pro Pro Ala
            500                 505                 510
Ile Ser Ala Glu Pro Ser Ile Thr Leu Ser Lys Gly Asp Ser Asp Asn
        515                 520                 525
Ser Ser Ser Gln Val Pro Pro Met Leu Gln Asp Thr Asp Lys Pro Lys
        530                 535                 540
Ser Asn Ala Lys Gln Asn Ser Val Pro Pro Ser Gln Thr Lys Ser Glu
545                 550                 555                 560
Thr Asn Trp Glu Ser Pro Lys Gln Ile Lys Lys Lys Lys Ala Arg
                565                 570                 575
Arg Glu Thr

<210> SEQ ID NO 2
<211> LENGTH: 2530
<212> TYPE: DNA
<213> ORGANISM: Mus musculus
<220> FEATURE:
<221> NAME/KEY: CDS
<222> LOCATION: (319)...(2058)

<400> SEQUENCE: 2
ggccgccatt gttccgccgg gggaggacag cgggtcctgg cgctggcgcc ccgacgccgc      60
ttagcggccg cctctggaga cactctgtcc ccgccgcccc gtgtcctcct ggtggcggcg     120
gcgtgaggcc ggctgcggag actgggaacc tttggctctc cccgtggcgg cggcggccct     180
ctatccccta ctccggcgtg agggttggcc gcgatgcgct cggcctgagg tgtcgcggcc     240
ctgtcgcctc ccacgactgt tccagcggcg gctccgctcc ccggcgtcat ccgcgagtc      300 tctctgacgg gagggaag atg gct gca cga agc tgg cag gac gag ctg gcc       351
                    Met Ala Ala Arg Ser Trp Gln Asp Glu Leu Ala
                    1               5                   10 cag cag gcc gag gag ggc tct gcc cgg ctg cgg gag ttg ctc tcg gtc       399
Gln Gln Ala Glu Glu Gly Ser Ala Arg Leu Arg Glu Leu Leu Ser Val
            15                  20                  25 ggc cta ggt ttt ctg cgc acg gag ttg ggc ctc gac ctg ggg cta gag       447
Gly Leu Gly Phe Leu Arg Thr Glu Leu Gly Leu Asp Leu Gly Leu Glu
        30                  35                  40 ccg aag cgg tac ccg ggc tgg gtg atc ctg gtg ggc acc ggc gct ctc       495
Pro Lys Arg Tyr Pro Gly Trp Val Ile Leu Val Gly Thr Gly Ala Leu
    45                  50                  55 ggg ctg ctc ctg ctc ttc ctt cta ggt tac ggc tgg gcc gcg gct tgc       543
Gly Leu Leu Leu Leu Phe Leu Leu Gly Tyr Gly Trp Ala Ala Ala Cys
60                  65                  70                  75 gcc ggc gcc cgc aag aag cga agg agc ccg ccc cgc aaa cgg gag gag       591
Ala Gly Ala Arg Lys Lys Arg Arg Ser Pro Pro Arg Lys Arg Glu Glu
```

|  |  |  |  |  |  |  |  |  |  |  |  |  |  |  |  |
|---|---|---|---|---|---|---|---|---|---|---|---|---|---|---|---|
|  |  |  | 80 |  |  |  |  | 85 |  |  |  |  | 90 |  |  |
| gcg | gcc | ccg | ccg | act | ccg | gcc | ccc | gac | gac | cta | gcc | cag | ctg | aag | aat | 639
| Ala | Ala | Pro | Pro | Thr | Pro | Ala | Pro | Asp | Asp | Leu | Ala | Gln | Leu | Lys | Asn |
|  |  |  | 95 |  |  |  |  | 100 |  |  |  |  | 105 |  |  | ctc aga agc gag gag caa aag aag aag aac cgg aag aag ctt cct gaa      687
Leu Arg Ser Glu Glu Gln Lys Lys Lys Asn Arg Lys Lys Leu Pro Glu
        110                 115                 120 aag ccc aaa cca aat gga cgg act gtt gaa gta ccc gag gat gaa gtt      735
Lys Pro Lys Pro Asn Gly Arg Thr Val Glu Val Pro Glu Asp Glu Val
125                 130                 135 gtt aga aat ccc cga agt ata act gca aaa caa gca cca gag aca gac      783
Val Arg Asn Pro Arg Ser Ile Thr Ala Lys Gln Ala Pro Glu Thr Asp
140                 145                 150                 155 aag aaa aat gaa aag tca aag aaa aat aag aag aaa tca aag tca gat      831
Lys Lys Asn Glu Lys Ser Lys Lys Asn Lys Lys Lys Ser Lys Ser Asp
                160                 165                 170 gct aaa gca gtg caa aac agt tca cgc cat gat gga aag gaa gtt gat      879
Ala Lys Ala Val Gln Asn Ser Ser Arg His Asp Gly Lys Glu Val Asp
        175                 180                 185 gaa gga gcc tgg gaa act aaa att agt cac aga gag aaa cga caa cag      927
Glu Gly Ala Trp Glu Thr Lys Ile Ser His Arg Glu Lys Arg Gln Gln
        190                 195                 200 cgt aaa cgt gat aaa gtg ctg act gat tct ggt tca ttg gat tca act      975
Arg Lys Arg Asp Lys Val Leu Thr Asp Ser Gly Ser Leu Asp Ser Thr
205                 210                 215 atc cct ggg ata gaa aat atc atc aca gtt acc acc gag caa ctt aca     1023
Ile Pro Gly Ile Glu Asn Ile Ile Thr Val Thr Thr Glu Gln Leu Thr
220                 225                 230                 235 act gca tca ttt cct gtt ggt tcc aag aag aat aaa ggt gat tct cat     1071
Thr Ala Ser Phe Pro Val Gly Ser Lys Lys Asn Lys Gly Asp Ser His
                240                 245                 250 cta aat gtt caa gtt agc aac ttt aag tct gga aaa gga gat tct aca     1119
Leu Asn Val Gln Val Ser Asn Phe Lys Ser Gly Lys Gly Asp Ser Thr
        255                 260                 265 ctg cag gtt act tca agg ctg aat gaa aat ctt act gtc aat gga gga     1167
Leu Gln Val Thr Ser Arg Leu Asn Glu Asn Leu Thr Val Asn Gly Gly
        270                 275                 280 ggc tgg agt gaa aag tct gta aaa ctc tcc tca caa ttg agt gag gag     1215
Gly Trp Ser Glu Lys Ser Val Lys Leu Ser Ser Gln Leu Ser Glu Glu
285                 290                 295 aag tgg aac tct gtc cca cct gct tct gca ggc aag agg aaa aca gag     1263
Lys Trp Asn Ser Val Pro Pro Ala Ser Ala Gly Lys Arg Lys Thr Glu
300                 305                 310                 315 cca tcg gct tgg act caa gac act ggt gac act aat gca aat ggg aaa     1311
Pro Ser Ala Trp Thr Gln Asp Thr Gly Asp Thr Asn Ala Asn Gly Lys
                320                 325                 330 gac tgg gga agg aat tgg agt gat cgc tca ata ttt tct ggc att gga     1359
Asp Trp Gly Arg Asn Trp Ser Asp Arg Ser Ile Phe Ser Gly Ile Gly
        335                 340                 345 tct act gct gag cca gtt tct cag tct acc act tct gat tat cag tgg     1407
Ser Thr Ala Glu Pro Val Ser Gln Ser Thr Thr Ser Asp Tyr Gln Trp
        350                 355                 360 gat gtt agc cgt aat caa cct tat atc gat gat gaa tgg tct ggg tta     1455
Asp Val Ser Arg Asn Gln Pro Tyr Ile Asp Asp Glu Trp Ser Gly Leu
365                 370                 375 aat ggt ttg tct tct gct gac cct agc tca gac tgg aat gca cca gca     1503
Asn Gly Leu Ser Ser Ala Asp Pro Ser Ser Asp Trp Asn Ala Pro Ala
380                 385                 390                 395 gag gag tgg ggg aac tgg gta gat gaa gat aga gct tca ctt ctg aag     1551

| | | | | | | | | | | | | | | | |
|---|---|---|---|---|---|---|---|---|---|---|---|---|---|---|---|
|Glu|Glu|Trp|Gly|Asn|Trp|Val|Asp|Glu|Asp|Arg|Ala|Ser|Leu|Leu|Lys|
| | | |400| | |405| | | | |410| | | | |

| | | | | | | | | | | | | | | | | |
|---|---|---|---|---|---|---|---|---|---|---|---|---|---|---|---|---|
|tcc|cag|gaa|cca|att|tct|aat|gat|caa|aag|gtt|tca|gat|gat|gat|aaa|1599|
|Ser|Gln|Glu|Pro|Ile|Ser|Asn|Asp|Gln|Lys|Val|Ser|Asp|Asp|Asp|Lys| |
| | |415| | | | |420| | | | |425| | | | |

| | | | | | | | | | | | | | | | | |
|---|---|---|---|---|---|---|---|---|---|---|---|---|---|---|---|---|
|gaa|aaa|ggg|gag|gga|gct|ctt|cca|act|gga|aaa|tct|aaa|aag|aaa|aag|1647|
|Glu|Lys|Gly|Glu|Gly|Ala|Leu|Pro|Thr|Gly|Lys|Ser|Lys|Lys|Lys|Lys| |
| | |430| | | | |435| | | | |440| | | | |

| | | | | | | | | | | | | | | | | |
|---|---|---|---|---|---|---|---|---|---|---|---|---|---|---|---|---|
|aag|aaa|aag|aag|aag|caa|ggg|gaa|gat|aac|tct|cac|aca|cag|gac|aca|1695|
|Lys|Lys|Lys|Lys|Lys|Gln|Gly|Glu|Asp|Asn|Ser|His|Thr|Gln|Asp|Thr| |
| |445| | | | |450| | | | |455| | | | | |

| | | | | | | | | | | | | | | | | |
|---|---|---|---|---|---|---|---|---|---|---|---|---|---|---|---|---|
|gaa|gac|cta|gaa|aag|gac|act|aga|gaa|gag|ctt|cca|gtg|aat|acc|tca|1743|
|Glu|Asp|Leu|Glu|Lys|Asp|Thr|Arg|Glu|Glu|Leu|Pro|Val|Asn|Thr|Ser| |
|460| | | | |465| | | | |470| | | | |475| |

| | | | | | | | | | | | | | | | | |
|---|---|---|---|---|---|---|---|---|---|---|---|---|---|---|---|---|
|aaa|gcc|cga|cca|aaa|cag|gag|aaa|gct|tgt|tcc|ctg|aag|acc|atg|agc|1791|
|Lys|Ala|Arg|Pro|Lys|Gln|Glu|Lys|Ala|Cys|Ser|Leu|Lys|Thr|Met|Ser| |
| | | |480| | | | |485| | | | |490| | | |

| | | | | | | | | | | | | | | | | |
|---|---|---|---|---|---|---|---|---|---|---|---|---|---|---|---|---|
|act|agt|gac|cca|gct|gaa|gta|ctc|atc|aaa|aat|agc|cag|cct|gtc|aag|1839|
|Thr|Ser|Asp|Pro|Ala|Glu|Val|Leu|Ile|Lys|Asn|Ser|Gln|Pro|Val|Lys| |
| | | |495| | | | |500| | | | |505| | | |

| | | | | | | | | | | | | | | | | |
|---|---|---|---|---|---|---|---|---|---|---|---|---|---|---|---|---|
|act|ctt|cct|cct|gct|atc|tct|gcc|gag|cca|tct|att|acc|tta|tca|aaa|1887|
|Thr|Leu|Pro|Pro|Ala|Ile|Ser|Ala|Glu|Pro|Ser|Ile|Thr|Leu|Ser|Lys| |
| | |510| | | | |515| | | | |520| | | | |

| | | | | | | | | | | | | | | | | |
|---|---|---|---|---|---|---|---|---|---|---|---|---|---|---|---|---|
|ggt|gac|tct|gac|aac|agc|tct|tcc|caa|gtg|cca|ccg|atg|tta|caa|gac|1935|
|Gly|Asp|Ser|Asp|Asn|Ser|Ser|Ser|Gln|Val|Pro|Pro|Met|Leu|Gln|Asp| |
| |525| | | | |530| | | | |535| | | | | |

| | | | | | | | | | | | | | | | | |
|---|---|---|---|---|---|---|---|---|---|---|---|---|---|---|---|---|
|aca|gac|aag|ccc|aag|tca|aat|gct|aag|caa|aac|agt|gtg|cct|ccc|tca|1983|
|Thr|Asp|Lys|Pro|Lys|Ser|Asn|Ala|Lys|Gln|Asn|Ser|Val|Pro|Pro|Ser| |
|540| | | | |545| | | | |550| | | | |555| |

| | | | | | | | | | | | | | | | | |
|---|---|---|---|---|---|---|---|---|---|---|---|---|---|---|---|---|
|cag|acc|aag|tct|gaa|act|aac|tgg|gaa|tct|cca|aaa|caa|ata|aaa|aag|2031|
|Gln|Thr|Lys|Ser|Glu|Thr|Asn|Trp|Glu|Ser|Pro|Lys|Gln|Ile|Lys|Lys| |
| | | | |560| | | | |565| | | | |570| | |

| | | | | | | | | |
|---|---|---|---|---|---|---|---|---|
|aag|aaa|aag|gcc|aga|cgg|gaa|acg|tga|atttttttt|tcctgaattg|2078|
|Lys|Lys|Lys|Ala|Arg|Arg|Glu|Thr|*| | | |
| | | |575| | | | | | | | | gacatgtgtt tacaaacact gtcttgaaga ttatgctgtt tatgcaataa tttgtgaaca  2138 tgtacagagt tttatataaa tttaaaccaa tttttaaaac aaaactgaac acaaccacca  2198 taaaatggaa tcaaggaaa gttaatttat gaaataaaga ggtcaacaga atacacagtg  2258 ctggaagaca cttgggagag tcttttcaat tgaacgagaa tgatcgtaat ttaagactat  2318 tatcctggtt ttacaacagt tacctgttta caacagactg tgccctgtct cctctgcagc  2378 tgaggaataa tgaatggatt ctgattagag agaaggctgc cgtgaggcca gtaggcaagt  2438 ccttggatct tatgcacgac cttagaccat ttgaatctgt tttatgctta aatcaaagtg  2498 ctttgatcaa atgtataatc tgccatatct tt  2530

```
<210> SEQ ID NO 3
<211> LENGTH: 63
<212> TYPE: PRT
<213> ORGANISM: Mus musculus

<400> SEQUENCE: 3
```

| | | | | | | | | | | | | | | | |
|---|---|---|---|---|---|---|---|---|---|---|---|---|---|---|---|
|Gly|Leu|Asn|Gly|Leu|Ser|Ser|Ala|Asp|Pro|Ser|Ser|Asp|Trp|Asn|Ala|
|1| | | |5| | | | |10| | | | |15| |

| | | | | | | | | | | | | | | |
|---|---|---|---|---|---|---|---|---|---|---|---|---|---|---|
|Pro|Ala|Glu|Glu|Trp|Gly|Asn|Trp|Val|Asp|Glu|Asp|Arg|Ala|Ser|Leu|
| | | |20| | | | |25| | | | |30| | |

| | | | | | | | | | | | | | | |
|---|---|---|---|---|---|---|---|---|---|---|---|---|---|---|
|Leu|Lys|Ser|Gln|Glu|Pro|Ile|Ser|Asn|Asp|Gln|Lys|Val|Ser|Asp|Asp|
| | | |35| | | | |40| | | | |45| | |

```
Asp Lys Glu Lys Gly Glu Gly Ala Leu Pro Thr Gly Lys Ser Lys
    50                  55                  60
```

<210> SEQ ID NO 4
<211> LENGTH: 8
<212> TYPE: DNA
<213> ORGANISM: Artificial Sequence
<220> FEATURE:
<223> OTHER INFORMATION: Synthetic oligonucleotide primer sequence
<220> FEATURE:
<221> NAME/KEY: misc_feature
<222> LOCATION: 3, 4, 5, 6, 7, 8
<223> OTHER INFORMATION: n = methylated A,T,C or G

<400> SEQUENCE: 4 ttnnnnnn                                                                  8

<210> SEQ ID NO 5
<211> LENGTH: 33
<212> TYPE: DNA
<213> ORGANISM: Artificial Sequence
<220> FEATURE:
<223> OTHER INFORMATION: Synthetic oligonucleotide primer sequence

<400> SEQUENCE: 5
accatggctg cacgaagctg gcaggacgag ctg                                     33

<210> SEQ ID NO 6
<211> LENGTH: 35
<212> TYPE: DNA
<213> ORGANISM: Artificial Sequence
<220> FEATURE:
<223> OTHER INFORMATION: Synthetic oligonucleotide primer sequence

<400> SEQUENCE: 6
tcacgtttcc cgtctggcct ttttcttctt tttta                                   35

<210> SEQ ID NO 7
<211> LENGTH: 38
<212> TYPE: DNA
<213> ORGANISM: Artificial Sequence
<220> FEATURE:
<223> OTHER INFORMATION: Synthetic oligonucleotide primer sequence

<400> SEQUENCE: 7
cccgccatgg ggttaaatgg tttgtcttct gctgaccc                                38

<210> SEQ ID NO 8
<211> LENGTH: 43
<212> TYPE: DNA
<213> ORGANISM: Artificial Sequence
<220> FEATURE:
<223> OTHER INFORMATION: Synthetic oligonucleotide primer sequence

<400> SEQUENCE: 8
cccgagatct tttagatttc ccagttggaa gagctccctc ccc                          43

<210> SEQ ID NO 9
<211> LENGTH: 36
<212> TYPE: DNA
<213> ORGANISM: Artificial Sequence
<220> FEATURE:
<223> OTHER INFORMATION: Synthetic oligonucleotide primer sequence

<400> SEQUENCE: 9
cccgggatcc gggtgcgggt taaatggttt gtcttc                                  36

```
<210> SEQ ID NO 10
<211> LENGTH: 42
<212> TYPE: DNA
<213> ORGANISM: Artificial Sequence
<220> FEATURE:
<223> OTHER INFORMATION: Synthetic oligonucleotide primer sequence

<400> SEQUENCE: 10
cccgctcgag ttagtgatgg tgatggtgat gagatctttt ag                              42

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide  sequence

<400> SEQUENCE: 11
gtgccaccga tgttacaag                                                        19

<210> SEQ ID NO 12
<211> LENGTH: 10
<212> TYPE: PRT
<213> ORGANISM: Artificial Sequence
<220> FEATURE:
<223> OTHER INFORMATION: myc epitope

<400> SEQUENCE: 12

Glu Gln Lys Leu Ile Ser Glu Glu Asp Leu
 1               5                  10

<210> SEQ ID NO 13
<211> LENGTH: 582
<212> TYPE: PRT
<213> ORGANISM: Homo sapiens

<400> SEQUENCE: 13

Met Ala Ala Arg Ser Trp Gln Asp Glu Leu Ala Gln Gln Ala Glu
 1               5                  10                  15

Gly Ser Ala Arg Leu Arg Glu Met Leu Ser Val Gly Leu Gly Phe Leu
                 20                  25                  30

Arg Thr Glu Leu Gly Leu Asp Leu Gly Leu Glu Pro Lys Arg Tyr Pro
             35                  40                  45

Gly Trp Val Ile Leu Val Gly Thr Gly Ala Leu Gly Leu Leu Leu Leu
 50                  55                  60

Phe Leu Leu Gly Tyr Gly Trp Ala Ala Cys Ala Gly Ala Arg Lys
 65                  70                  75                  80

Lys Arg Arg Ser Pro Pro Arg Lys Arg Glu Glu Ala Ala Val Pro
                 85                  90                  95

Ala Ala Ala Pro Asp Asp Leu Ala Leu Leu Lys Asn Leu Arg Ser Glu
                100                 105                 110

Glu Gln Lys Lys Lys Asn Arg Lys Lys Leu Ser Glu Lys Pro Lys Pro
                115                 120                 125

Asn Gly Arg Thr Val Glu Val Ala Glu Gly Glu Ala Val Arg Thr Pro
            130                 135                 140

Gln Ser Val Thr Ala Lys Gln Pro Pro Glu Ile Asp Lys Lys Asn Glu
145                 150                 155                 160

Lys Ser Lys Lys Asn Lys Lys Lys Ser Lys Ser Asp Ala Lys Ala Val
                165                 170                 175
```

-continued

```
Gln Asn Ser Ser Arg His Asp Gly Lys Glu Val Asp Glu Gly Ala Trp
            180                 185                 190
Glu Thr Lys Ile Ser His Arg Glu Lys Arg Gln Gln Arg Lys Arg Asp
        195                 200                 205
Lys Val Leu Thr Asp Ser Gly Ser Leu Asp Ser Thr Ile Pro Gly Ile
    210                 215                 220
Glu Asn Thr Ile Thr Val Thr Thr Glu Gln Leu Thr Thr Ala Ser Phe
225                 230                 235                 240
Pro Val Gly Ser Lys Lys Asn Lys Gly Asp Ser His Leu Asn Val Gln
                245                 250                 255
Val Ser Asn Phe Lys Ser Gly Lys Gly Asp Ser Thr Leu Gln Val Ser
            260                 265                 270
Ser Gly Leu Asn Glu Asn Leu Thr Val Asn Gly Gly Trp Asn Glu
        275                 280                 285
Lys Ser Val Lys Leu Ser Ser Gln Ile Ser Ala Gly Glu Glu Lys Trp
    290                 295                 300
Asn Ser Val Ser Pro Ala Ser Ala Gly Lys Arg Lys Thr Glu Pro Ser
305                 310                 315                 320
Ala Trp Ser Gln Asp Thr Gly Asp Ala Asn Thr Asn Gly Lys Asp Trp
                325                 330                 335
Gly Arg Ser Trp Ser Asp Arg Ser Ile Phe Ser Gly Ile Gly Ser Thr
            340                 345                 350
Ala Glu Pro Val Ser Gln Ser Thr Thr Ser Asp Tyr Gln Trp Asp Val
        355                 360                 365
Ser Arg Asn Gln Pro Tyr Ile Asp Asp Glu Trp Ser Gly Leu Asn Gly
    370                 375                 380
Leu Ser Ser Ala Asp Pro Asn Ser Asp Trp Asn Ala Pro Ala Glu Glu
385                 390                 395                 400
Trp Gly Asn Trp Val Asp Glu Glu Arg Ala Ser Leu Leu Lys Ser Gln
                405                 410                 415
Glu Pro Ile Pro Asp Asp Gln Lys Val Ser Asp Asp Lys Glu Lys
            420                 425                 430
Gly Glu Gly Ala Leu Pro Thr Gly Lys Ser Lys Lys Lys Lys Lys
        435                 440                 445
Lys Lys Lys Gln Gly Glu Asp Asn Ser Thr Ala Gln Asp Thr Glu Glu
    450                 455                 460
Leu Glu Lys Glu Ile Arg Glu Asp Leu Pro Val Asn Thr Ser Lys Thr
465                 470                 475                 480
Arg Pro Lys Gln Glu Lys Ala Phe Ser Leu Lys Thr Ile Ser Thr Ser
                485                 490                 495
Asp Pro Ala Glu Val Leu Val Lys Asn Ser Gln Pro Ile Lys Thr Leu
            500                 505                 510
Pro Pro Ala Thr Ser Thr Glu Pro Ser Val Ile Leu Ser Lys Ser Asp
        515                 520                 525
Ser Asp Lys Ser Ser Ser Gln Val Pro Pro Ile Leu Gln Glu Thr Asp
    530                 535                 540
Lys Ser Lys Ser Asn Thr Lys Gln Asn Ser Val Pro Pro Ser Gln Thr
545                 550                 555                 560
Lys Ser Glu Thr Ser Trp Glu Ser Pro Lys Gln Ile Lys Lys Lys Lys
                565                 570                 575
Lys Ala Arg Arg Glu Thr
            580
```

<210> SEQ ID NO 14
<211> LENGTH: 381
<212> TYPE: PRT
<213> ORGANISM: Rattus norvegicus

<400> SEQUENCE: 14

```
Met Ala Ile Gly Tyr Ile Ser Glu Lys Arg Ser Lys Ala Arg Ala Gly
 1               5                  10                  15
Leu Leu Ile Val Pro Ala Gln Ala Arg Gly Lys Gly Ala Ala Val Val
                20                  25                  30
Gln Gly Leu Arg His Ile Gly Glu Tyr Gln Lys Pro Arg Ala Lys Glu
            35                  40                  45
Gln Pro Lys Arg Leu Pro Glu Lys Pro Lys Gln Asn Arg Leu Leu Val
        50                  55                  60
Glu Leu Pro Glu Asp Glu Val Val Ser Arg Ile Pro Ala Lys Gln
 65                  70                  75                  80
Pro Pro Lys Arg Asp Thr Glu Asn Lys Ser Lys Lys Asn Lys Lys
                 85                  90                  95
Ser Ser Lys Ser Asp Ala Lys Ala Val Pro Asn Ser Leu Cys His Thr
            100                 105                 110
Lys Asn Thr Ile Thr Val Thr Thr Ser Gln Leu Thr Thr Ala Ser Phe
        115                 120                 125
Pro Val Asp Ser Lys Lys Asn Lys Gly Val Ser Arg Leu Asn Val Gln
    130                 135                 140
Ile Ser Ile Leu Val Trp Lys Gly Asp Thr Thr Ile Gln Asp Ser Ser
145                 150                 155                 160
Gly Lys Leu Gly Asn Leu Thr Val Asn Gly Val Trp Ser Glu Asn
                165                 170                 175
Ser Val Lys Leu Ala Ser Leu Leu Ser Thr Trp Glu Val Glu Leu Cys
            180                 185                 190
Pro Thr Cys Leu Cys Arg Gln Glu Lys Gln Ser His Leu Leu Gly Leu
        195                 200                 205
Lys Thr Pro Val Met Glu Met Gln Met Ile Lys Thr Gly Glu Arg Thr
    210                 215                 220
Gly Val Ile Thr Gln Tyr Phe Leu Ala Phe Glu Ser Val Glu Pro Val
225                 230                 235                 240
Phe Gln Thr Thr Thr Ser Asp Tyr Gln Trp Asp Val Ser His Asn Gln
                245                 250                 255
Pro Cys Ile Asp Asp Glu Trp Ser Glu Val Asn Cys Gly Lys Gln Leu
            260                 265                 270
Arg Leu Glu Cys Thr Cys Arg Arg Glu Gly Asn Trp Val Asp Glu Glu
        275                 280                 285
Arg Gly Ser Leu Leu Lys Ser Gln Glu Leu Ile Ser Asn Asp Gln Lys
    290                 295                 300
Phe Ser Asp Asp Lys Gly Lys Gly Glu Gly Ile Lys Asn Trp His
305                 310                 315                 320
Pro Ile Gln Thr Pro Leu Pro Ala Ile Ser Ala Glu Leu Phe Ser Ser
                325                 330                 335
Ala Thr Asn Val Thr Arg Phe Thr Asp Lys His Lys Ser Asn Ala Lys
            340                 345                 350
Gln Asn Ser Val Pro Pro Pro Leu Ser Gln Ile Arg Ser Glu Thr
        355                 360                 365
Asn Tyr Asn Ser Pro Lys Gln Ile Lys Lys Lys Ser
    370                 375                 380
```

<210> SEQ ID NO 15
<211> LENGTH: 544
<212> TYPE: PRT
<213> ORGANISM: Danio rerio

<400> SEQUENCE: 15

```
Met Asp Gln Asp Trp Gln Ala Leu Ala Thr Gln Arg Ala Glu Tyr Val
 1               5                  10                  15

Ser Asp Arg Ile Arg Gly Leu Leu Ser Ser Gly Leu Asp Phe Leu Arg
            20                  25                  30

Ala Glu Leu Gly Val Asp Leu Gly Ile Lys Pro Glu Lys Cys Pro Ser
        35                  40                  45

Trp Leu Ile Leu Ser Ala Ala Leu Ile Gly Leu Leu Leu Val Val
    50                  55                  60

Leu Ala Ala Cys Gly Arg Arg Lys Arg Ala Ala Pro Val Thr Ala
65                  70                  75                  80

Ser Pro Arg Ser Ile Ala Ala Ala Pro Val Lys Thr Ser Ala Pro
                85                  90                  95

Pro Lys Thr Val Lys Thr Glu Pro Ser Glu Pro Lys Lys Lys Asn Lys
            100                 105                 110

Lys Lys Ala Ala Asp Lys Gln Lys Ala Gln Ala Asn Gly Gln Thr Val
        115                 120                 125

Ala Glu Pro Gln Glu Glu Ile Lys Val Thr Gly Glu Lys Lys Lys Ala
    130                 135                 140

Pro Ala Pro Thr Pro Thr Arg Ala Pro Ala Pro Ala Pro Thr Arg Ala
145                 150                 155                 160

Pro Ala Pro Ala Pro Thr Pro Ala Ser Ala Pro Ala Pro Val Pro Val
                165                 170                 175

Pro Ala Pro Lys Pro Lys Gln Lys Pro Ala Pro Thr Pro Ala Gln Pro
            180                 185                 190

Pro Ala Asp Thr Lys Thr Lys Lys Asn Lys Lys Lys Ala Lys Pro Glu
        195                 200                 205

Leu Lys Thr Ala Gln Asp Val Ser Ser Thr Asp Gly Lys Glu Pro Asp
    210                 215                 220

Glu Ala Gly Ala Trp Glu Thr Lys Val Ser Asn Arg Glu Lys Arg Gln
225                 230                 235                 240

Gln Arg Lys Lys Glu Lys Gly Pro Gly Glu Ser Ser Gly Ser Pro Glu
                245                 250                 255

Ser Gly Asp Arg Ala Ser Met Lys Val Glu Gln Pro Val Val Thr Ala
            260                 265                 270

Thr Ala Gly Asn Lys Lys Asn Lys Glu Ser Ser Arg Val Lys Ala Ser
        275                 280                 285

Lys Gly Asp Ala Ile Ile Ala Pro Val Thr Ser Ala Trp Asn Asp Val
    290                 295                 300

Asn Ser Val Asn Gly Gly Leu Thr Glu Val Pro Val Lys Gln Ala
305                 310                 315                 320

Ile Gln Ser Asn Ala Leu Asn Asn Asp Lys Trp Ser Ala Gly Lys Lys
                325                 330                 335

Thr Ser Gly His Lys Asn Arg Glu Asn Ser Thr Trp Lys Gln Glu Ser
            340                 345                 350

Glu Gly Pro Leu Thr Gly Leu Asp Gly Arg Ile Lys Ala Glu Pro Asn
        355                 360                 365

Gln Val Asn Leu Thr Met Leu Gly Leu Asn Pro Ser Gly Gly Glu Thr
    370                 375                 380
```

```
Gly Ser Lys Ser Ser Ile Glu Ile Gly Lys Trp Asp Lys Thr Pro Val
385                 390                 395                 400

Val Asp Ser Glu Trp Ser Ser Phe Asn Gly Leu Gly Ser Val Asp Pro
            405                 410                 415

Ser Ser Asp Trp Asn Ala Pro Ser Glu Leu Trp Asp Asn Phe Glu Ala
        420                 425                 430

Lys Val Asp Ala Ser Ala Leu Lys Glu Ile Pro Val Ser Lys Pro Leu
            435                 440                 445

Val Glu Ser Asn Asp Asp Lys Asp Lys Glu Asp Pro Ala Gly Gly Gly
        450                 455                 460

Lys Ser Lys Arg Arg Lys Lys Lys Arg Pro Glu Glu Glu Gly Ser
465                 470                 475                 480

Ala Val Glu Val Ile Pro Glu Val Ser Ala Pro Ala Glu Lys Ser Val
                485                 490                 495

Thr Val Lys Pro His Pro Pro His Val Pro Lys Asp Ala Gly Ser
                    500                 505                 510

Lys Gln Asn Ile Pro Pro Gln Ser Ser Gln Lys Ser Asp Gln Asn
                515                 520                 525

Trp Glu Pro Pro Lys Gln Val Gln Lys Lys Lys Val Arg Arg Glu Thr
                    530                 535                 540

<210> SEQ ID NO 16
<211> LENGTH: 2031
<212> TYPE: DNA
<213> ORGANISM: Homo sapiens

<400> SEQUENCE: 16
ttcctcgctt ccctcgacta ttccactgcg tctccgcgcc ccggcgtcat cctgcgagtc      60
cctctgacgg gagggaagat ggctgcacgg agctggcagg acgagctggc ccagcaggcc     120
gaggagggct cggcccggct gcgggaaatg ctctcggtcg gcctaggctt tctgcgcacc     180
gagctgggcc tcgacctggg gctggagccg aaacggtacc ccggctgggt gatcctggtg     240
ggcactggcg cgctcgggct gctgctgctg tttctgctgg gctacggctg ggccgcgget     300
tgcgccggcg cccgcaaaaa gcggaggagc ccgccccgca gcgggagga ggcggcggcc     360
gtgccggccg cggcccccga cgacctggcc ttgctgaaga tctccggag cgaggaacag     420
aagaagaaga accggaagaa actgtccgag aagcccaaac caaatgggcg gactgttgaa     480
gtggctgagg tgaagctgt tcgaacacct caaagtgtaa cagcaaagca gccaccagag     540
attgacaaga aaaatgaaaa gtcaaagaaa ataagaaga atcaaagtc agatgctaaa     600
gcagtgcaaa acagttcacg ccatgatgga aggaagttg atgaaggagc ctgggaaact     660
aaaattagtc acagagagaa acgacagcag cgtaaacgtg ataaggtgct gactgattct     720
ggttcattgg attcaactat ccctgggata gaaaatacca tcacagttac caccgagcaa     780
cttacaaccg catcatttcc tgttggttcc aagaagaata aggtgattc tcatctaaat     840
gttcaagtta gcaactttaa atctggaaaa ggagattcta cacttcaggt ttcttcagga     900
ttgaatgaaa acctcactgt caatggagga ggctggaatg aaagtctgt aaactctcc     960
tcacagatca gtgcaggtga ggagaagtgg aactccgttt cacctgcttc tgcaggaaag    1020
aggaaaactg agccatctgc ctggagtcaa gacactggag atgctaatac aaatggaaaa    1080
gactggggaa ggagttggag tgaccgttca atattttctg gcattgggtc tactgctgag    1140
ccagtttctc agtctaccac ttctgattat cagtgggatg ttagccgtaa tcaaccctat    1200
```

```
atcgatgatg aatggtctgg gttaaatggt ctgtcttctg ctgatcccaa ctctgattgg    1260
aatgcaccag cagaagagtg gggcaattgg gtagacgaag aaagagcttc acttctaaag    1320
tcccaggaac caattcctga tgatcaaaag gtctcagatg atgataaaga aaagggagag    1380
ggagctcttc caactgggaa atccaaaaag aaaaaaaaga aaagaagaa gcaaggtgaa    1440 gataactcta ctgcacagga cacagaagaa ttagaaaaag agattagaga agaccttcca    1500
gtgaatacct ctaaaacccg tccaaaacag gaaaaagctt tttccttgaa gaccataagc    1560
actagtgatc cagccgaagt actcgtcaaa aatagccagc ctatcaagac tcttccacct    1620
gctacttcta ccgagccatc tgtaatctta tcaaaaagtg attctgacaa gagctcttcc    1680
caagtgccgc caatactaca agagacagat aaatccaagt caaataccaa gcaaaatagt    1740
gtgcctcctt cacagaccaa gtctgaaact agctgggaat ctcccaaaca aataaaaaag    1800
aagaaaaaag ccagacgaga aacgtgaaat ttttttttcct gaattggaca tgtgtttgca    1860
aacacttgtc ttgaagatta tgctgtttat gcaataattt gtgaacatgt acagagtttt    1920
atataaattt aaaccaattt ttaaaacaaa actgcggaca ccaccataaa aatggaatca    1980
aaagaaagtt aatttatgaa attaagaggt cagcagaata tactcagtga t            2031
```

<210> SEQ ID NO 17
<211> LENGTH: 63
<212> TYPE: PRT
<213> ORGANISM: Homo sapiens

<400> SEQUENCE: 17

```
Gly Leu Asn Gly Leu Ser Ser Ala Asp Pro Asn Ser Asp Trp Asn Ala
 1               5                  10                  15

Pro Ala Glu Glu Trp Gly Asn Trp Val Asp Glu Glu Arg Ala Ser Leu
            20                  25                  30

Leu Lys Ser Gln Glu Pro Ile Pro Asp Asp Gln Lys Val Ser Asp Asp
        35                  40                  45

Asp Lys Glu Lys Gly Glu Gly Ala Leu Pro Thr Gly Lys Ser Lys
    50                  55                  60
```

<210> SEQ ID NO 18
<211> LENGTH: 581
<212> TYPE: PRT
<213> ORGANISM: Rattus norvegicus

<400> SEQUENCE: 18

```
Met Ala Ala Arg Ser Trp Gln Asp Glu Leu Ala Gln Gln Ala Glu Glu
 1               5                  10                  15

Gly Ser Ala Arg Leu Arg Glu Leu Leu Ser Val Gly Leu Gly Phe Leu
            20                  25                  30

Arg Thr Glu Leu Gly Leu Asp Leu Gly Leu Glu Pro Lys Arg Tyr Pro
        35                  40                  45

Ser Trp Val Ile Leu Val Gly Thr Gly Ala Leu Gly Leu Leu Leu Leu
    50                  55                  60

Phe Leu Leu Gly Tyr Gly Trp Ala Ala Ala Cys Ala Gly Ala Arg Lys
65                  70                  75                  80

Lys Arg Arg Ser Pro Pro Arg Lys Arg Glu Glu Val Thr Pro Pro Thr
                85                  90                  95

Pro Ala Pro Glu Asp Pro Ala Gln Leu Lys Asn Leu Arg Ser Glu Glu
            100                 105                 110

Gln Lys Lys Lys Asn Arg Lys Lys Leu Pro Glu Lys Pro Lys Pro Asn
        115                 120                 125
```

```
Gly Arg Thr Val Glu Ile Pro Glu Asp Glu Val Val Arg Thr Pro Arg
    130                 135                 140

Ser Ile Thr Ala Lys Gln Pro Pro Glu Thr Asp Lys Lys Asn Glu Lys
145                 150                 155                 160

Ser Lys Lys Asn Lys Lys Ser Lys Ser Asp Ala Lys Ala Val Gln
            165                 170                 175

Asn Ser Ser Arg His Asp Gly Lys Glu Val Asp Glu Gly Ala Trp Glu
                180                 185                 190

Thr Lys Ile Ser His Arg Glu Lys Arg Gln Gln Arg Lys Arg Asp Lys
            195                 200                 205

Val Leu Thr Asp Ser Gly Ser Leu Asp Ser Thr Ile Pro Gly Ile Glu
    210                 215                 220

Asn Thr Ile Thr Val Thr Thr Glu Gln Leu Thr Thr Ala Ser Phe Pro
225                 230                 235                 240

Val Gly Ser Lys Lys Asn Lys Gly Asp Ser His Leu Asn Val Gln Val
                245                 250                 255

Ser Asn Phe Lys Ser Gly Lys Gly Asp Ser Thr Leu Gln Val Ser Ser
                260                 265                 270

Gly Leu Asn Glu Asn Ile Thr Val Asn Gly Gly Trp Ser Glu Lys
    275                 280                 285

Ser Val Lys Leu Ser Ser Gln Leu Ser Ala Gly Glu Glu Lys Trp Asn
    290                 295                 300

Ser Val Pro Pro Ala Ser Ala Gly Lys Arg Lys Thr Glu Gln Ser Ala
305                 310                 315                 320

Trp Thr Gln Asp Pro Gly Asp Thr Asn Ala Asn Gly Lys Asp Trp Gly
                325                 330                 335

Arg Asn Trp Ser Asp Arg Ser Ile Phe Ser Gly Ile Gly Ser Thr Ala
                340                 345                 350

Glu Pro Val Ser Gln Ser Thr Thr Ser Asp Tyr Gln Trp Asp Gly Ser
                355                 360                 365

Arg Asn Gln Pro His Ile Asp Asp Glu Trp Ser Gly Leu Asn Gly Leu
    370                 375                 380

Ser Ser Ala Asp Pro Ser Ser Asp Trp Asn Ala Pro Ala Glu Glu Trp
385                 390                 395                 400

Gly Asn Trp Val Asp Glu Asp Arg Ala Ser Leu Leu Lys Ser Gln Glu
                405                 410                 415

Pro Ile Ser Asn Asp Gln Lys Asp Ser Asp Asp Lys Glu Lys Gly
                420                 425                 430

Glu Gly Ala Leu Pro Thr Gly Lys Ser Lys Lys Lys Lys Lys
    435                 440                 445

Lys Lys Gln Gly Glu Asp Asn Ser Ile Thr Gln Asp Thr Glu Asp Leu
    450                 455                 460

Glu Lys Asp Thr Arg Glu Glu Leu Pro Val Asn Thr Ser Lys Ala Arg
465                 470                 475                 480

Pro Lys Gln Glu Lys Ala Cys Ser Leu Lys Thr Met Ser Thr Ser Asp
                485                 490                 495

Pro Val Glu Val Leu Ile Lys Asn Ser Gln Pro Ile Lys Thr Leu Pro
                500                 505                 510

Pro Ala Ile Ser Ala Glu Pro Ser Val Thr Leu Ser Lys Gly Asp Ser
            515                 520                 525

Asp Lys Ser Ser Ser Gln Val Pro Pro Met Leu Gln Asp Thr Asp Lys
    530                 535                 540
```

```
Pro Lys Ser Asn Ala Lys Gln Asn Ser Val Pro Pro Ser Gln Thr Lys
545                 550                 555                 560

Ser Glu Thr Asn Trp Glu Ser Pro Lys Gln Ile Lys Lys Lys Lys
            565                 570                 575

Ala Arg Arg Glu Thr
                580

<210> SEQ ID NO 19
<211> LENGTH: 550
<212> TYPE: PRT
<213> ORGANISM: Mus musculus

<400> SEQUENCE: 19

Met Phe Thr Arg Lys His Leu Met Pro Lys Asp Leu Ile Leu Lys His
1               5                   10                  15

Leu Thr Phe Ala Asn Ser Leu Ser Ile Ile Ser Arg Gly Ile Pro Arg
                20                  25                  30

Ala Met Ser Asp Cys Gly Phe Lys Tyr Phe Leu Asp Asp Ile Gly Cys
            35                  40                  45

Lys Leu Ile Val Tyr Ile Cys Arg Ile Thr Arg Gly Met Ser Leu Tyr
    50                  55                  60

Ala Met Cys Leu Leu Ser Cys Phe Gln Ala Ile Thr Ile Asn Gln Ser
65                  70                  75                  80

Asn Ser Lys Cys Leu Thr Leu Lys His Arg Thr Thr Lys Tyr Ile Gly
                85                  90                  95

Ser Cys Cys Ser Val Ser Trp Leu Val Gln Leu Phe Leu Asn Ile Leu
            100                 105                 110

Thr Pro Thr Arg Val Ser Gly Pro Ile Tyr Asn Lys Asn Val Thr Asn
        115                 120                 125

Met Met Ser Tyr Gly Tyr Cys Ser Trp Ile Ala Ser Gly Asn Met Ala
130                 135                 140

Thr Ala Val Tyr Val Leu Leu Leu Cys Phe Ser Asp Ala Val Cys Leu
145                 150                 155                 160

Gly Leu Met Ala Cys Ser Ser Val Ser Met Val Ser Ile Leu Tyr Arg
                165                 170                 175

His Lys Arg Gln Val Lys His Ile His Ser Ala Gln His Leu Ile Lys
            180                 185                 190

Asp Ser Pro Glu Asp Arg Ala Thr Gln Thr Ile Leu Ile Leu Met Cys
        195                 200                 205

Thr Phe Val Leu Ser Tyr Ser Phe Ser Ser Ile Val Ile Phe Thr
210                 215                 220

Thr Tyr Ser Lys Tyr Pro Met Leu Trp Gly Val Thr Lys Ala Arg Asn
225                 230                 235                 240

Ser Asp Glu Met Trp Arg Ile Leu Ala Ile Ile Ser Asn Val Thr Met
                245                 250                 255

Val Ser Ile Pro Ile Ser Ser His Ile Asn His Asp Ser Met Tyr Tyr
            260                 265                 270

Glu Met Lys Asp Lys Asn Val Gln Leu Val Gly Ser Leu Cys Ser Ser
        275                 280                 285

Tyr Gly Tyr Ser Thr Ala Lys Gln Glu Val Ser Leu Glu Thr Leu Leu
    290                 295                 300

Val Ala Phe Thr Leu Phe Thr Val Pro His Tyr Ser Gly Lys Asn Val
305                 310                 315                 320

Gln Ala Gln Asn Lys Ala Gly Leu Thr Trp Lys Ala Thr Leu Val Pro
                325                 330                 335
```

```
Pro Met Gln Ile His Gln Lys Asn Val Pro Ala Pro Lys Ala Pro
        340                 345                 350

Ser Leu Leu Ser Ile Met Lys Ile Ser Val Leu Gly Glu Val Arg Ile
        355                 360                 365

His Gly Met Glu Thr Lys Leu Ser Lys Leu Val Thr Ser Glu Glu Leu
        370                 375                 380

Gly Gly Lys Ser Ser Gln Pro Pro Asp Arg Asn Ala Thr Leu Arg Lys
385                 390                 395                 400

Arg Arg Glu Asn Ala Asn Trp Thr Ile Leu Asn Glu Asn Lys Lys Lys
                405                 410                 415

Gln Lys Lys Arg Lys Lys Gln Gly Glu Asp Asn Tyr Phe Ile Gln
        420                 425                 430

Asp Thr Glu Glu Leu Glu Lys Asp Ile Arg Glu Ile Leu Val Thr
        435                 440                 445

Thr Cys Lys Ala Ile Pro Asn Trp Glu Asn Val Cys Ser Leu Lys Thr
450                 455                 460

Met Ser Thr Ile Asp Pro Thr Glu Val Asp Val Lys Asn Glu Gln Cys
465                 470                 475                 480

Ile Gln Thr Leu Leu Pro Thr Ile Ser Pro Glu Leu Phe Ser Thr Ala
                485                 490                 495

Thr Asp Ile Thr Arg Phe Thr Asp Lys His Lys Ser Asn Thr Glu Gln
        500                 505                 510

Asn Ser Val Pro Pro Ser Pro Leu Ser Gln Thr Arg Ser Ala Thr Asn
        515                 520                 525

Cys Lys Thr Pro Lys Gln Ile Lys Lys Lys Lys Ser Gln Thr Gly
        530                 535                 540

Asn Val Ile Phe Leu Ser
545                 550

<210> SEQ ID NO 20
<211> LENGTH: 277
<212> TYPE: PRT
<213> ORGANISM: Mus musculus

<400> SEQUENCE: 20

Met Leu Ala Gln Lys Gln Arg Asn Asn Ala Cys Phe Lys Cys Gly Ser
1               5                   10                  15

Leu Gly His Phe Lys Asn Asp Cys Pro Lys Asn Arg Gly Ala Glu Glu
            20                  25                  30

Ser Gly Gln Ala Ser His Ala Pro Gly Gly Leu Trp Ala Val Gly Val
        35                  40                  45

Cys Ser Phe Gln Lys Ile Leu Ser Ala Ser Asp Thr Ser Ser Met Ile
    50                  55                  60

Phe Gln Val Lys Ala Arg Ser Leu Ser Val Trp Met Ala Arg Ala Gly
65                  70                  75                  80

Leu Leu Ile Val Pro Ala Gln Ala Arg Gly Lys Gly Ala Ala Val Val
                85                  90                  95

Gln Gly Leu Arg His Ile Gly Glu Tyr Gln Lys Pro Arg Ala Lys Glu
            100                 105                 110

Gln Pro Lys Arg Leu Pro Glu Lys Pro Lys Gln Asn Arg Leu Leu Val
        115                 120                 125

Glu Leu Pro Glu Asp Glu Val Val Ser Arg Ser Ile Pro Ala Lys Gln
    130                 135                 140

Pro Pro Lys Arg Asp Thr Glu Asn Lys Lys Ser Lys Lys Asn Lys Lys
```

-continued

```
145                 150                 155                 160
Ser Ser Lys Ser Asp Ala Lys Ala Val Pro Asn Ser Leu Cys His Thr
            165                 170                 175

Lys Lys Gln Ser His Leu Leu Gly Leu Lys Thr Pro Val Met Glu Met
            180                 185                 190

Gln Met Ile Lys Thr Gly Glu Arg Thr Gly Val Ile Thr Gln Tyr Phe
        195                 200                 205

Leu Ala Phe Glu Ser Val Glu Pro Val Phe Gln Thr Thr Thr Ser Asp
        210                 215                 220

Tyr Gln Trp Asp Val Ser His Asn Gln Pro Cys Ile Asp Asp Glu Trp
225                 230                 235                 240

Ser Glu Val Asn Cys Gly Lys Gln Val Arg Pro Asn Gly Pro Ser Arg
            245                 250                 255

His Ser Gly Pro Leu Pro Gly Pro Val Asn Pro Thr Phe Thr Ala Phe
            260                 265                 270

Pro Glu His Ala Gln
            275
```